(12) United States Patent  (10) Patent No.: US 8,298,444 B2
Yamada et al.  (45) Date of Patent: Oct. 30, 2012

(54) OLIGOANILINE COMPOUND

(75) Inventors: Tomohisa Yamada, Funabashi (JP);
Takuji Yoshimoto, Funabashi (JP)

(73) Assignee: Nissan Chemical Industries, Ltd.,
Tokyo (JP)

( * ) Notice: Subject to any disclaimer, the term of this patent is extended or adjusted under 35 U.S.C. 154(b) by 411 days.

(21) Appl. No.: 12/595,479

(22) PCT Filed: Apr. 9, 2008

(86) PCT No.: PCT/JP2008/056974
§ 371 (c)(1),
(2), (4) Date: Dec. 7, 2009

(87) PCT Pub. No.: WO2008/129947
PCT Pub. Date: Oct. 30, 2008

(65) Prior Publication Data
US 2010/0230639 A1 Sep. 16, 2010

(30) Foreign Application Priority Data

Apr. 12, 2007 (JP) ................. 2007-104410
Aug. 27, 2007 (JP) ................. 2007-219311

(51) Int. Cl.
*H01B 1/00* (2006.01)
*C08G 73/00* (2006.01)
*H01L 29/08* (2006.01)

(52) U.S. Cl. ............... 252/500; 257/40; 528/422

(58) Field of Classification Search ............... 252/500; 257/40; 528/422
See application file for complete search history.

(56) References Cited

U.S. PATENT DOCUMENTS

| 5,317,169 | A | 5/1994 | Nakano | |
|---|---|---|---|---|
| 5,726,457 | A | 3/1998 | Nakano | |
| 6,017,665 | A * | 1/2000 | Grune et al. | 430/58.2 |
| 6,815,090 | B1 * | 11/2004 | Tagami et al. | 428/690 |
| 2003/0010959 | A1 | 1/2003 | Lee | |
| 2005/0208334 | A1 | 9/2005 | Lee | |
| 2008/0029742 | A1 * | 2/2008 | Yoshimoto et al. | 252/500 |

FOREIGN PATENT DOCUMENTS

| CN | 101088992 A | 12/2007 |
|---|---|---|
| JP | 3273087 A | 12/1991 |
| JP | H09-151371 | * 6/1997 |
| JP | 10-168446 A | 6/1998 |
| JP | H10-168446 | * 6/1998 |
| JP | 10-265773 A | 10/1998 |
| JP | H10-265773 | * 10/1998 |
| JP | 2002-151272 | * 5/2002 |

(Continued)

OTHER PUBLICATIONS

Van Slyke, et al.; Organic Electroluminescent Devices with Improved Stability; Appl. Phys. Lett.; Oct. 1996; pp. 2160-2162; 69 (15); United States.
Gustafsson, et al.; Flexible Light-Emitting Diodes Made from Soluble Conducting Polymers; Nature; Jun. 11, 1992; pp. 477-479; vol. 357; United Kingdom.

(Continued)

*Primary Examiner* — Mark Kopec
*Assistant Examiner* — Jaison Thomas
(74) *Attorney, Agent, or Firm* — Birch, Stewart, Kolasch & Birch, LLP

(57) ABSTRACT

Any of the oligoaniline compounds with a triphenylamine structure represented by the formula (1) exhibits satisfactory light emitting efficiency and brightness performance when used in either an OLED device or a PLED device and is further satisfactory in the solubility in organic solvents so as to be applicable to various coating methods.

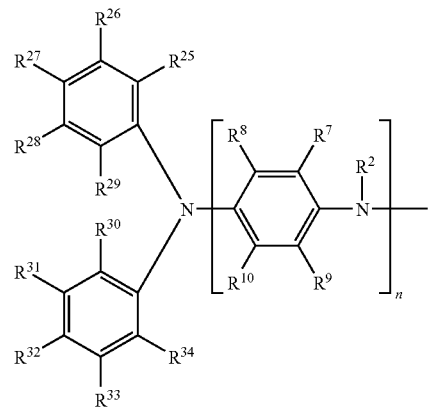

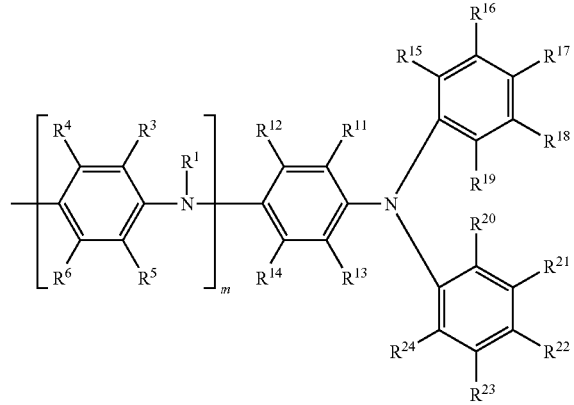

(each of $R^1$ and $R^2$ independently is a hydrogen atom, an optionally substituted monovalent hydrocarbon group, t-butoxycarbonyl, etc.; each of $R^3$ to $R^{34}$ independently is a hydrogen atom, hydroxyl, silanol, thiol, carboxyl, a phosphoric group, a phosphoric ester group, ester, thioester, amido, nitro, an optionally substituted monovalent hydrocarbon group, etc.; and each of m and n is an integer of 1 or greater provided that they satisfy the relationship m+n ≦ 20).

39 Claims, No Drawings

FOREIGN PATENT DOCUMENTS

| | | | |
|---|---|---|---|
| JP | 2002-151272 A | | 5/2002 |
| JP | 2003-045667 | * | 2/2003 |
| JP | 2003-45667 A | | 2/2003 |
| JP | 2005-108828 A | | 4/2005 |
| JP | 2005-276832 | * | 10/2005 |
| JP | 2005-276832 A | | 10/2005 |
| JP | 2007-005444 | * | 1/2007 |
| JP | 2007-5444 A | | 1/2007 |
| JP | H09-151371 A | | 7/2009 |
| WO | WO 2004-043117 A1 | | 5/2004 |
| WO | WO 2005-000832 A1 | | 1/2005 |
| WO | WO 2005-043962 A1 | | 5/2005 |
| WO | WO 2005-107335 A1 | | 11/2005 |
| WO | WO 2006-025342 A1 | | 3/2006 |

OTHER PUBLICATIONS

Bharathan, et al.; Polymer Electroluminescent Devices Processed by Inkjet Printing: I. Polymer Light-Emitting Logo; Applied Physics Letters; May 25, 1998; pp. 2660-2662; vol. 72; No. 21; United States.

Ochi, et al.; Preparation of Linear Oligoaniline Derivatives Using Titanium Alkoxide as a Condensing Agent; Bull. Chem. Soc. of Jpn.; Jun. 1994; pp. 1749-1752; vol. 67; Japan.

Koppang; Preparation of Poly (N-phenylimino-perfluorophenylene). Solvent Effects on Reactions Between Anilides and Hexafluorobenzene; Journal of Fluorine Chemistry; 1976; pp. 389-400; vol. 8; The Netherlands.

* cited by examiner

OLIGOANILINE COMPOUND

TECHNICAL FIELD

The present invention relates to an oligoaniline compound and, more particularly, to an oligoaniline compound having the triphenylamine structure, the use of this compound as a charge transport material, and a charge transport varnish containing this compound.

BACKGROUND ART

It has been reported that the low-molecular-weight organic electroluminescent (OLED for short hereinafter) device is provided with a copper phthalocyanine (CuPC) layer as the hole injection layer so as to improve the initial characteristics, such as reduced drive voltage and increased light-emitting efficiency, and to improve the life characteristics (Non-Patent Document 1: Applied Physics Letters, U.S., 1996, vol. 69, p. 2160-2162).

It has also been reported that the organic electroluminescence (PLED for short hereinafter) device with a polymeric luminescent material produces the same effect as the OLED device does if it is provided with the hole transport layer in the form of thin film of polyaniline-based material (Patent Document 1: JP-A 3-273087; Non-Patent Document 2: Nature, U.K., 1992, vol. 357, p. 477-479) or polythiophene-based material (Non-Patent Document 3: Applied Physics Letters, U.S., 1998, vol. 72, p. 2660-2662).

It has recently been found that a charge transport varnish in the form of homogeneous solution completely dissolved in an organic solvent can be produced from a highly soluble low-molecular-weight oligoaniline-based material or oligothiophene-based material. Reportedly, this varnish is made into the hole injection layer to be placed in the organic electroluminescence (organic EL for short hereinafter) device so that the underlying substrate becomes flat or the resulting EL device exhibits good characteristic properties (Patent Document 2: JP-A 2002-151272; Patent Document 3: WO 2005/043962 pamphlet).

The low-molecular-weight oligomer compound intrinsically has such a low viscosity that it gives rise to a solution of ordinary organic solvent which presents difficulties in forming a highly uniform film by coating (such as spin coating, ink jet coating, and spray coating) and baking under various conditions owing to its narrow process margin.

Nevertheless, it has become possible to form a highly uniform film by various coating methods as the result of using additional solvents for adjustment of viscosity, boiling point, and vapor pressure (Patent Document 4: WO 2004/043117 pamphlet; Patent Document 5: WO 2005/107335 pamphlet).

As mentioned above, it has recently become common practice to use a low-molecular-weight oligomer compound for the hole injection layer in the organic EL device.

However, the low-molecular-weight oligomer compound is still required to improve in solubility so that it easily adapts itself to various coating methods, such as spin coating, ink jet coating, and spray coating. It is also required to improve further in conductivity as well as in light emitting efficiency and luminance characteristics which are necessary for organic EL devices.

Particularly, improvement in light emitting efficiency and luminance characteristics is important to both OLED devices and PLED devices.

The characteristic properties required of the hole injection layer include ability to inject holes into the luminescent layer, ability to block electrons from the luminescent layer, and ability to prevent deactivation of excitons in the luminescent layer. These functions greatly affect the light emitting efficiency and luminance characteristics of the organic EL device mentioned above. Consequently, there is a demand for a low-molecular-weight oligomer compound for the hole injection layer that realizes outstanding functions.

Incidentally, it has been reported that the organic EL device has an extended life if it has a thin film formed from a composition of conductive polymer (such as polystyrenesulfonic acid and polyaniline) incorporated with a silane compound (see Patent Document 6). However, nothing has been reported about an instance in which a silane compound is added to the charge transport varnish containing a low-molecular-weight compound.

Patent Document 1: JP-A 3-273087

Patent Document 2: JP-A 2002-151272

Patent Document 3: WO 2005/043962 pamphlet

Patent Document 4: WO 2004/043117 pamphlet

Patent Document 5: WO 2005/107335 pamphlet

Patent Document 6: JP-A 2003-45667

Non-Patent Document 1: Applied Physics Letters, U.S., 1996, vol. 69, p. 2160-2162

Non-Patent Document 2: Nature, U.K., 1992, vol. 357, p. 477-479

Non-Patent Document 3: Applied Physics Letters, U.S., 1998, vol. 72, p. 2660-2662

DISCLOSURE OF THE INVENTION

Problems to be Solved by the Invention

The present invention has been completed in view of the foregoing. It is an object of the present invention to provide an oligoaniline compound which exhibits good light-emitting efficiency and luminance characteristics when applied to either OLED devices or PLED devices and which also has a good solubility in organic solvents that makes it applicable to various coating methods.

Means for Solving the Problem

As the result of intensive studies to achieve the above-mentioned object, the present inventors found that an oligoaniline compound having the triphenylamine structure at both ends of the molecular chain has a good solubility in organic solvents, exhibits a remarkable charge transport ability when used in combination with a charge accepting material, and high light-emitting efficiency and good luminance characteristics when used as the hole injection layer of the organic EL device. This finding led to the present invention.

That is, the present invention covers the following.
1. An oligoaniline compound represented by the formula (1).

[Chemical Formula 1]

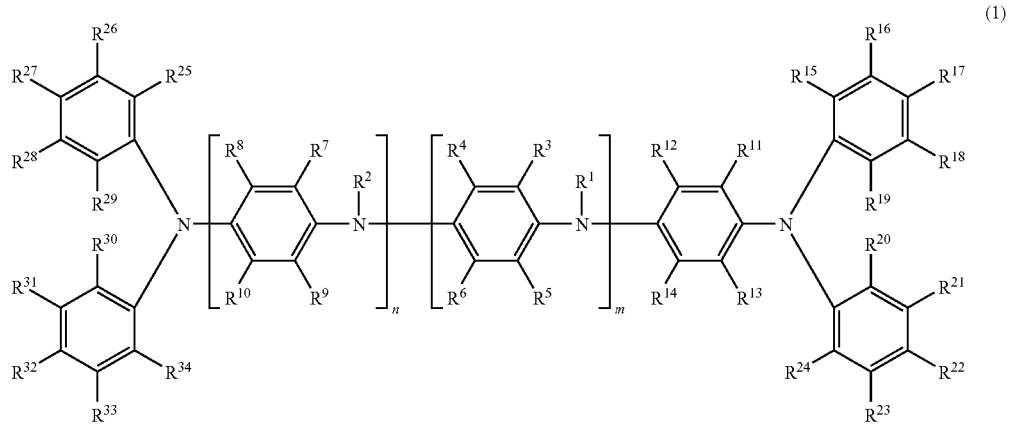

(where $R^1$ and $R^2$ each independently denote a hydrogen atom, substituted or unsubstituted monovalent hydrocarbon group, t-butoxycarbonyl group, or benzyloxycarbonyl group; $R^3$-$R^{34}$ each independently denote a hydrogen atom, hydroxyl group, silanol group, thiol group, carboxyl group, phosphoric acid group, phosphoric ester group, ester group, thioester group, amido group, nitro group, substituted or unsubstituted monovalent hydrocarbon group, organooxy group, organoamino group, organosilyl group, organothio group, acyl group, sulfonic group, or halogen atom; and m and n each denote an integer no smaller than 1 such that m+n≦20.)

2. The oligoaniline compound as defined in paragraph 1 above, wherein $R^1$ and $R^2$ each independently denote a hydrogen atom or t-butoxycarbonyl group; $R^3$-$R^{34}$ each independently denote a hydrogen atom, substituted or unsubstituted monovalent hydrocarbon group, organooxy group, organoamino group, or halogen atom; and m and n each denote an integer no smaller than 1 such that m+n≦10.

3. The oligoaniline compound as defined in paragraph 2 above, wherein $R^3$-$R^{34}$ each independently denote a hydrogen atom, substituted or unsubstituted monovalent hydrocarbon group, or halogen atom; and m and n each denote an integer no smaller than 1 such that m+n≦5.

4. The oligoaniline compound as defined in paragraph 2 above, wherein the monovalent hydrocarbon group denoted by any of $R^3$-$R^{34}$ is a phenyl group, biphenyl group, naphthyl group, or substituted or unsubstituted arylamine.

5. The oligoaniline compound as defined in paragraph 2 above, wherein the halogen atom is a fluorine atom.

6. A quinonediimine compound which is the oligoaniline compound as defined in paragraph 1 above in its oxidized form.

7. A charge transport varnish which contains either the oligoaniline compound as defined in any of paragraphs 1 to 5 above or the quinonediimine compound as defined in paragraph 6 above.

8. The charge transport varnish as defined in paragraph 7 above which further contains an electron accepting dopant substance or a hole accepting dopant substance.

9. The charge transport varnish as defined in paragraph 8 above, wherein the charge accepting dopant substance is an arylsulfonic acid derivative represented by the formula (2).

[Chemical Formula 2]

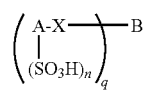

[where X denotes O, S, or NH; A denotes a naphthalene ring or anthracene ring which may have a substituent group other than X and $SO_3H$ groups as many as n; and B denotes a substituted or unsubstituted hydrocarbon group, 1,3,5-triazine group, or substituted or unsubstituted group represented by the formula (3) or (4)

[Chemical Formula 3]

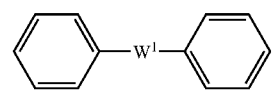

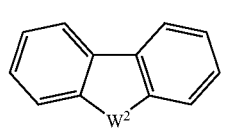

(where $W^1$ and $W^2$ each independently denote any of O, S, S(O) group, and $S(O_2)$ group, or any of substituted or unsubstituted N, Si, P, and P(O) group); n denotes the number of sulfonic acid groups connecting to A, which is an integer such that 1≦n≦4; and q denotes the number of B connecting to X, which is an integer that satisfies 1≦q.]

10. The charge transport varnish as defined in any of paragraphs 7 to 9 above, which further contains at least one species of silane compounds.

11. The charge transport varnish as defined in paragraph 10 above, which is dissolved in an organic solvent.

12. The charge transport varnish as defined in paragraph 11 above, whose organic solvent contains 0.0001 to 10 wt % of water.
13. The charge transport varnish as defined in any of paragraphs 10 to 12 above, in which the amount of the silane compound contained therein is 1 to 50 wt % for the total amount of solids thereof.
14. The charge transport varnish as defined in any of paragraphs 10 to 13 above, in which the silane compound is at least one species selected from dialkoxysilane compounds, trialkoxysilane compounds, tetraalkoxysilane compounds, and silicone compounds.
15. The charge transport varnish as defined in paragraph 14 above, in which the silane compound is a trialkoxysilane compound.
16. The charge transport varnish as defined in paragraph 15 above, in which the trialkoxysilane is one represented by the formula (27).

$$Y^1 Si(OY^2)_3 \quad (27)$$

(where $Y^1$ denotes a halogen atom, hydrogen atom, or any of $C_{1-12}$ alkyl group, $C_{2-12}$ alkenyl group, $C_{2-12}$ alkynyl group, aryl group, or heteroaryl group which may be substituted with Z and $Y^2$ denotes a $C_{1-12}$ alkyl group, with Z denoting a halogen atom, hydrogen atom, $C_{1-12}$ haloalkyl group, $C_{1-12}$ alkyl group, hydroxyl group, mercapto group, amino group, $C_{1-12}$ haloalkoxyl group, $C_{1-12}$ alkoxyl group, $C_{2-12}$ alkenyl group, $C_{2-12}$ haloalkenyl group, $C_{2-12}$ alkynyl group, $C_{2-12}$ haloalkynyl group, $C_{1-12}$ alkylthio group, $C_{1-12}$ monoalkylamino group, $C_{1-12}$ dialkylamino group, glycidoxy group, $C_{1-12}$ alkylcarbonyl group, $C_{2-12}$ alkenylcarbonyl group, $C_{2-12}$ alkynylcarbonyl group, $C_{1-12}$ alkylcarbonyloxy group, $C_{2-12}$ alkenylcarbonyloxy group, $C_{2-12}$ alkynylcarbonyloxy group, aryl group, halogenated aryl group, heteroaryl group, or halogenated heteroaryl group.)

17. The charge transport varnish as defined in paragraph 16 above, in which the Z denotes a halogen atom, hydrogen atom, $C_{1-12}$ haloalkyl group, $C_{1-12}$ alkyl group, $C_{2-12}$ alkenyl group, $C_{2-12}$ haloalkenyl group, $C_{2-12}$ alkynyl group, $C_{2-12}$ haloalkynyl group, aryl group, halogenated aryl group, heteroaryl group, or halogenated heteroaryl group.
18. The charge transport varnish as defined in paragraph 16 above, in which the $Y^1$ denotes a fluorine atom, hydrogen atom, or any of $C_{1-12}$ alkyl group, $C_{2-12}$ alkenyl group, $C_{2-12}$ alkynyl group, aryl group, and heteroaryl group which may be substituted with Z; and the Z denotes a halogen atom, hydrogen atom, $C_{1-12}$ haloalkyl group, $C_{1-12}$ alkyl group, $C_{2-12}$ alkenyl group, $C_{2-12}$ haloalkenyl group, $C_{2-12}$ alkynyl group, $C_{2-12}$ haloalkynyl group, aryl group, halogenated aryl group, heteroaryl group, or halogenated heteroaryl group.
19. The charge transport varnish as defined in paragraph 14 above, in which the silane compound is a dialkoxysilane compound.
20. The charge transport varnish as defined in paragraph 19 above, in which the dialkoxysilane compound is one represented by the formula (20).

$$Y^3 Y^4 Si(OY^5)_2 \quad (28)$$

(where $Y^3$ and $Y^4$ each independently denote a halogen atom or any of $C_{1-12}$ alkyl group, $C_{2-12}$ alkenyl group, $C_{2-12}$ alkynyl group, aryl group, and heteroaryl group which may be substituted with Z and $Y^5$ denotes $C_{1-12}$ alkyl group, with Z denoting a halogen atom, hydrogen atom, $C_{1-12}$ haloalkyl group, $C_{1-12}$ alkyl group, hydroxyl group, mercapto group, amino group, $C_{1-12}$ haloalkoxyl group, $C_{1-12}$ alkoxyl group, $C_{2-12}$ alkenyl group, $C_{2-12}$ haloalkenyl group, $C_{2-12}$ alkynyl group, $C_{2-12}$ haloalkynyl group, $C_{1-12}$ alkylthio group, $C_{1-12}$ monoalkylamino group, $C_{1-12}$ dialkylamino group, glycidoxy group, $C_{2-12}$ alkylcarbonyl group, $C_{2-12}$ alkenylcarbonyl group, $C_{2-12}$ alkynylcarbonyl group, $C_{1-12}$ alkylcarbonyloxy group, $C_{2-12}$ alkenylcarbonyloxy group, $C_{2-12}$ alkynylcarbonyloxy group, aryl group, halogenated aryl group, heteroaryl group, or halogenated heteroaryl group.)

21. The charge transport varnish as defined in paragraph 20 above, in which the Z denotes a halogen atom, hydrogen atom, $C_{1-12}$ haloalkyl group, $C_{1-12}$ alkyl group, $C_{2-12}$ alkenyl group, $C_{2-12}$ haloalkenyl group, $C_{2-12}$ alkynyl group, $C_{2-12}$ haloalkynyl group, aryl group, halogenated aryl group, heteroaryl group, or halogenated heteroaryl group.
22. The charge transport varnish as defined in paragraph 20 above, in which the $Y^3$ and $Y^4$ each independently denote a fluorine atom, hydrogen atom, or any of $C_{1-12}$ alkyl group, $C_{2-12}$ alkenyl group, $C_{2-12}$ alkynyl group, aryl group, and heteroaryl group which may be substituted with Z which denotes a halogen atom, hydrogen atom, $C_{1-12}$ haloalkyl group, $C_{1-12}$ alkyl group, $C_{2-12}$ alkenyl group, $C_{2-12}$ haloalkenyl group, $C_{2-12}$ alkynyl group, $C_{2-12}$ haloalkynyl group, aryl group, halogenated aryl group, heteroaryl group, or halogenated heteroaryl group.
23. The charge transport varnish as defined in paragraph 14 above, in which the silane compound is a tetraalkoxysilane compound.
24. The charge transport varnish as defined in paragraph 23 above, in which the tetraalkoxysilane compound is one represented by the formula (29).

$$Si(OY^6)_2 \quad (29)$$

(where $Y^6$ denotes a $C_{1-12}$ alkyl group.)

25. The charge transport varnish as defined in paragraph 24 above, in which the $Y^6$ denotes a methyl group, ethyl group, or propyl group.
26. The charge transport varnish as defined in paragraph 10 above, in which the silane compound is a combination of at least two species selected from dialkoxysilane compounds, trialkoxysilane compounds, tetraalkoxysilane compounds, and silicone compounds.
27. The charge transport varnish as defined in paragraph 10 above, in which the silane compound is a combination of at least two species selected from trialkoxysilane compounds, tetraalkoxysilane compounds, and dialkoxysilane compounds.
28. The charge transport varnish as defined in paragraph 10 above, in which the silane compound is a combination of at least two species selected from trialkoxysilane compounds.
29. The charge transport varnish as defined in paragraph 10 above, in which the silane compound is a combination of at least two species selected from tetraalkoxysilane compounds.
30. The charge transport varnish as defined in paragraph 10 above, in which the silane compound is a combination of at least two species selected from dialkoxysilane compounds.
31. The charge transport varnish as defined in paragraph 10 above, in which the silane compound is a combination of one or more species selected from trialkoxysilane compounds and one or more species selected from tetraalkoxysilane compounds.
32. The charge transport varnish as defined in paragraph 10 above, in which the silane compound is a combination of one or more species selected from trialkoxysilane compounds and one or more species selected from dialkoxysilane compounds.
33. The charge transport varnish as defined in paragraph 10 above, in which the silane compound is a combination of one or more species selected from trialkoxysilane compounds and one or more species selected from silicone compounds.

34. The charge transport varnish as defined in paragraph 10 above, in which the silane compound is a combination of one or more species selected from tetraalkoxysilane compounds and one or more species selected from dialkoxysilane compounds.
35. The charge transport varnish as defined in paragraph 10 above, in which the silane compound is a combination of one or more species selected from tetraalkoxysilane compounds and one or more species selected from silicone compounds.
36. The charge transport varnish as defined in paragraph 10 above, in which the silane compound is a combination of one or more species selected from dialkoxysilane compounds and one or more species selected from silicone compounds.
37. A charge transport thin film which contains the oligoaniline compound as defined in any of paragraphs 1 to 5 above or the quinonediimine compound as defined in paragraph 6 above.
38. A charge transport thin film which is formed from the charge transport varnish as defined in any of paragraphs 7 to 36 above.
39. An organic electroluminescence device having the charge transport thin film as defined in paragraph 37 or 38 above.

Advantageous Effects

The oligoaniline compound according to the present invention has the triphenylamine structure and exhibits good conductivity owing to its high hopping mobility. Therefore, it gives rise to a thin film which also exhibits good conductivity. This thin film contributes to improved characteristic properties of the organic EL device containing it.

According to the present invention, the oligoaniline compound having the triphenylamine structure may be used in combination with a silane compound to form a thin film for the organic EL device. This thin film not only greatly extends the life of the organic EL device but also improves the luminance of the organic EL device.

Meanwhile, conductive polymers and conjugated polymers exhibit a high conductivity because they permit charges to move in the direction of the main chain of each molecule. For this reason, it is common practice to increase the number of minimum repeating units, thereby extending the main chain, in order to improve conductivity. This procedure is not employed in the present invention for the oligoaniline compound having the triphenylamine structure. Instead improvement in conductivity is achieved by activating the charge hopping movement between adjacent molecules.

The oligoaniline compound according to the present invention gives rise to a thin film which is superior in flatness and charge transportability. Because of these characteristic properties, the thin film will find use as the hole transport layer of solar cells, the electrode of fuel cells, the protective film for capacitor electrodes, and antistatic film.

BEST MODE FOR CARRYING OUT THE INVENTION

The following is a detailed description of the present invention.

The oligoaniline compound is represented by the formula (1), in which $R^1$ and $R^2$ each independently denote a hydrogen atom, substituted or unsubstituted monovalent hydrocarbon group, t-butoxycarbonyl group, or benzyloxycarbonyl group.

The monovalent hydrocarbon group mentioned above is not specifically restricted in carbon number; however, it should preferably have a carbon number of 1 to 20, more preferably 1 to 8.

Examples of the substituted or unsubstituted monovalent hydrocarbon group include alkyl groups, such as methyl group, ethyl group, n-propyl group, i-propyl group, n-butyl group, i-butyl group, t-butyl group, n-hexyl group, n-octyl group, 2-ethylhexyl group, and decyl group; cycloalkyl groups, such as cyclopentyl group and cyclohexyl group; bicycloalkyl groups, such as bicyclohexyl group; alkenyl groups, such as vinyl group, 1-propenyl group, 2-propenyl group, isopropenyl group, 1-methyl-2-propenyl group, 1- or 2- or 3-butenyl group, and hexenyl group; aryl groups, such as phenyl group, xylyl group, tolyl group, biphenyl group, and naphthyl group; and aralkyl groups, such as benzyl group, phenylethyl group, and phenylcyclohexyl group. These monovalent hydrocarbon groups may have their hydrogen atoms partly or entirely substituted with halogen atoms, hydroxyl groups, alkoxyl groups, sulfonic groups, or the like.

Incidentally, "unsubstituted" means connection of hydrogen atoms. Also, the substituent groups may link with each other to form a cyclic structure.

Those which are independently denoted by the foregoing $R^1$ and $R^2$ particularly include a hydrogen atom, methyl group, ethyl group, or t-butoxycarbonyl group, of which a hydrogen atom or t-butoxycarbonyl group is preferable.

In other words, the preferred oligoaniline compound is one in which both $R^1$ and $R^2$ are hydrogen atoms or t-butoxycarbonyl groups, $R^1$ is a hydrogen atom and $R^2$ is a t-butoxycarbonyl group, or $R^1$ is a t-butoxycarbonyl group and $R^2$ is a hydrogen atom.

In the formula (1) above, $R^3$-$R^{34}$ each independently denote a hydrogen atom, hydroxyl group, amino group, silanol group, thiol group, carboxyl group, phosphoric acid group, phosphoric ester group, ester group, thioester group, amido group, nitro group, substituted or unsubstituted monovalent hydrocarbon group, organooxy group, organoamino group, organosilyl group, organothio group, acyl group, sulfonic group, halogen atom, or the like.

Examples of the substituted or unsubstituted monovalent hydrocarbon group are the same as those listed above.

Examples of the organooxy group include alkoxyl groups, alkenyloxy groups, aryloxy groups, and the like. These alkyl groups and alkenyl groups are also exemplified by the same substituent groups listed above.

Examples of the organoamino group include alkylamino groups, such as methylamino group, ethylamino group, propylamino group, butylamino group, pentylamino group, hexylamino group, heptylamino group, octylamino group, nonylamino group, decylamino group, and laurylamino group; dialkylamino groups, such as dimethylamino group, diethylamino group, dipropylamino group, dibutylamino group, dipentylamino group, dihexylamino group, diheptylamino group, dioctylamino group, dinonylamino group, and didecylamino group; dicycloalkylamino groups, such as dicyclohexylamino group; morpholino group; and arylamino groups, such as biphenylamino group.

Examples of the organosilyl group include trimethylsilyl group, triethylsilyl group, tripropylsilyl group, tributylsilyl group, tripentylsilyl group, trihexylsilyl group, pentyldimethylsilyl group, hexyldimethylsilyl group, octyldimethylsilyl group, and decyldimethylsilyl group.

Examples of the organothio group include alkylthio groups, such as methylthio group, ethylthio group, propylthio group, butylthio group, pentylthio group, hexylthio group, heptylthio group, octylthio group, nonylthio group, decylthio group, and laurylthio group.

Examples of the acyl group include formyl group, acetyl group, propionyl group, butylyl group, isobutylyl group, valeryl group, isovaleryl group, and benzoyl group.

The halogen atom is exemplified by chlorine, bromine, fluorine, and iodine atoms.

The phosphoric ester group is exemplified by —P(O)(OQ$^1$)(OQ$^2$).

The ester group is exemplified by —C(O)OQ$^1$ and —OC(O)Q$^1$.

The thioester group is exemplified by —C(S)OQ$^1$ and —OC(S)Q$^1$.

The amido group is exemplified by —C(O)NHQ$^1$, —NHC(O)Q$^1$, —C(O)NQ$^1$Q$^2$, and —NQ$^1$C(O)Q$^2$.

Here, the foregoing Q$^1$ and Q$^2$ each denote an alkyl group, alkenyl group, or aryl group; their examples are the same as those which have been listed for the foregoing monovalent hydrocarbon group.

The foregoing monovalent hydrocarbon group, organooxy group, organoamino group, organosilyl group, organothio group, acyl group, phosphoric ester group, ester group, thioester group, and amido group denoted by R$^3$-R$^{34}$ are not specifically restricted in carbon number. However, their carbon number is usually 1 to 20, preferably 1 to 8.

Preferable among these groups, which are denoted by R$^3$-R$^{34}$ mutually independently, are a hydrogen atom, substituted or unsubstituted monovalent hydrocarbon group, organooxy group, organoamino group, and halogen atom. Particularly preferable among them are a hydrogen atom, substituted or unsubstituted monovalent hydrocarbon group, and halogen atom.

Preferred monovalent hydrocarbon groups are phenyl groups, biphenyl groups, and naphthyl groups.

Preferred halogen atoms are fluorine atoms. Preferred organoamino groups are arylamino groups, especially biphenylamino groups.

In the formula (1) above, m and n each independently denote an integer no smaller than 1 such that m+n≦20, preferably m+n≦10, more preferably m+n≦5.

Meeting this condition makes the oligoaniline compound to have good charge transport characteristics and high solubility in various solvents.

The oligoaniline compound represented by the formula (1) should preferably have a degree of dispersion of 1 (which means the absence of molecular weight distribution) in view of its high solubility and uniform charge transport characteristics.

The lower limit of the molecular weight is 200, preferably 400, for low volatility and good charge transport characteristics. The upper limit is 5000, preferably 3000, for good solubility.

The oligoaniline compound represented by the formula (1) above may be produced by the following method, for example.

The oligoaniline compound (5) shown below has its halogen atoms (X) reacted by the amine compounds having the triphenylamine structure, which are represented by the formulas (6) and (7). Alternatively, the oligoaniline compound (5') shown below has its halogen atoms (X) reacted by the amine compounds having the diphenylamine structure, which are represented by the formulas (6') and (7'). The procedure of reaction is not specifically restricted; the ordinary nucleophilic substitution reaction may be employed.

[Chemical Formula 4]

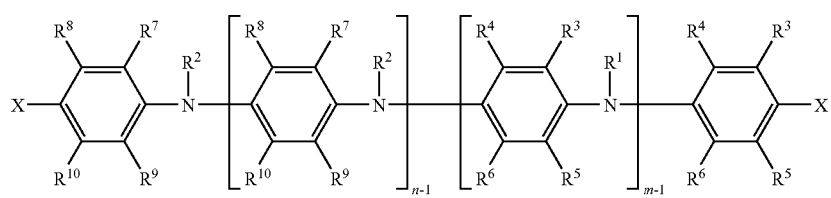

(5)

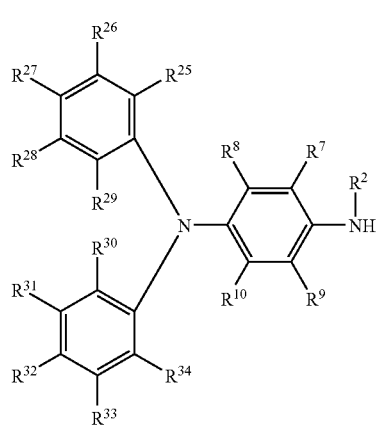

(6)

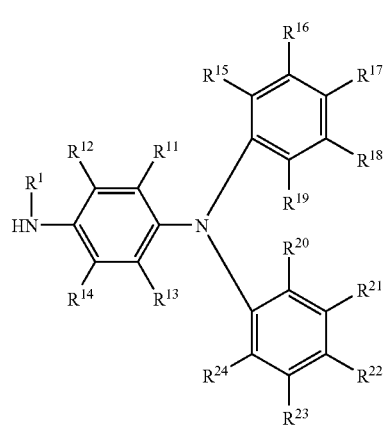

(7)

[Chemical Formula 5]

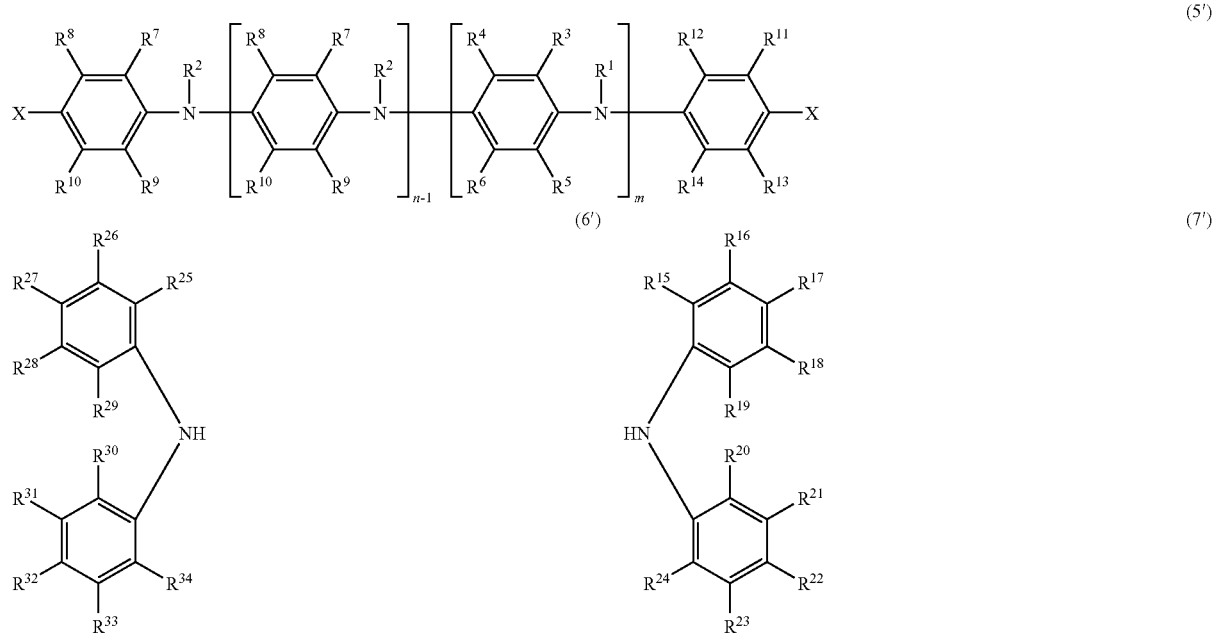

The oligoaniline compounds (5) and (5') may be ones whose amino groups are protected by the foregoing t-butoxycarbonyl group or benzyloxycarbonyl group, for example.

The amine compounds (6) and (6'), or (7) and (7'), should preferably be used in an amount (in mole) twice as much as the oligoaniline compound (5) or (5').

The reaction of the oligoaniline compound (5) with the amine compounds (6) and (6'), or (7) and (7'), may optionally be catalyzed. The catalyst includes, for example, palladium acetate (II), tris(dibenzylideneacetone) palladium (0), bis (dibenzylideneacetone) palladium (0), and (1,1'-bis-(diphenylphosphino)ferrocene) dichloropalladium. The ligand includes, for example, (tri-t-butylphosphine), (2,2'-bis (diphenylphosphino)-1,1'-binaphthyl), and (tri-o-toluoylphosphine). The base includes, for example, NaOtBu, $CsCO_3$, $K_2CO_3$, and NaOPh. The solvent includes, for example, toluene, xylene, THF, NMP, DMF, and 1,4-dioxane.

The reaction temperature should preferably be 0 to 160° C. The reaction time usually ranges from 0.1 to 100 hours. The reaction may be followed by removal of solvent by distillation, removal of inorganic salts by solid-liquid extraction or liquid-liquid extraction, and purification by recrystallization, silica gel chromatography, etc.

The oligoaniline compound having protected amino groups may have its protecting groups removed by treatment with a strong acid such as trifluoroacetic acid and hydrochloric acid.

Also, if the oligoaniline compound having protected amino groups is to be made into a charge transport varnish containing an acid dopant, it may be used as such for the charge transport material because the protecting groups drop off when the thin film is formed.

Especially, the oligoaniline compound having protected amino groups dissolves more readily in organic solvents than the one having no protected amino groups. Therefore, it is suitable as a highly soluble host.

The charge transport varnish according to the present invention contains as the charge transport material the oligoaniline compound represented by the formula (1) or the quinonediimine compound which is the oligoaniline compound in its oxidized form.

Here, the charge transport varnish is a product formed from the oligoaniline compound (as the charge transport material) according to the present invention, which is essential for the charge transport mechanism, by dissolution or dispersion in at least one species of solvents. It may also be formed from a charge transport organic material composed of the charge transport material and an electron or hole accepting dopant substance.

Incidentally, "charge transport" is synonymous with "conductivity," and it implies ability to transport holes, electrons, or both holes and electrons. The charge transport varnish according to the present invention may be one which is capable of transporting charges by itself or one which can be formed into a solid film capable of transporting charges.

The charge transport varnish according to the present invention may optionally be incorporated with a charge accepting dopant substance for its improvement in charge transport ability and others. The charge accepting dopant substance is an electron accepting dopant substance for the hole transport material or a hole accepting dopant substance for the electron transport material. Either of them should preferably excel in charge accepting ability. The charge accepting dopant substance is not specifically restricted in solubility so long as it is soluble in at least one species of solvents used for the varnish.

Typical examples of the electron accepting dopant substance include inorganic strong acids, such as hydrogen chloride, sulfuric acid, nitric acid, and phosphoric acid; Lewis acids, such as aluminum (III) chloride ($AlCl_3$), titanium (IV) tetrachloride ($TiCl_4$), boron tribromide ($BBr_3$), boron trifluoride-ether complex ($BF_3.OEt_2$), iron (III) chloride ($FeCl_3$), copper (II) chloride ($CuCl_2$), antimony (V) pentachloride (V) ($SbCl_5$), arsenic (V) pentafluoride ($AsF_5$), phosphorus pentafluoride ($PF_5$), and tris(4-bromophenyl)aluminum hexachloroantimonate (TBPAH); organic strong acids, such as benzenesulfonic acid, tosylic acid, camphorsulfonic acid, hydroxybenzenesulfonic acid, 5-sulfosalycylic acid, dodecylbenzenesulfonic acid, polystyrenesulfonic acid, 1,4-benzooxydisulfonic acid derivative (disclosed in WO 2005/000832 pamphlet), arylsulfonic acid derivative (disclosed in WO 2006/025342 pamphlet), and dinonylnaphthalenesulfonic acid derivative (disclosed in JP-A 2005-108828); and organic or inorganic oxidizing agents, such as 7,7,8,8-tetracyanoquinodimethane (TCNQ), 2,3-dichloro-5,6-dicyano-1,4-benzoquinone (DDQ), and iodine. They are not limitative.

Particularly desirable electron accepting dopant substances include such organic strong acids as 5-sulfosalicylic acid, dodecylbenzenesulfonic acid, polystyrenesulfonic acid, 1,4-benzodioxydisulfonic acid derivative (disclosed in WO 2005/000832 pamphlet), and dinonylnaphthalenesulfonic acid derivative (disclosed in JP-A 2005-108828).

Other desirable ones are those sulfonic acid derivatives represented by the formula (2).

[Chemical Formula 6]

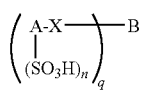

(2)

[where X denotes O, S, or NH; A denotes a naphthalene or anthracene ring which may have a substituent group other than X and $(SO_3H)_n$; B denotes a substituted or unsubstituted hydrocarbon group, 1,3,5-triazine group, or any substituted or unsubstituted group represented by the formula (3) or (4) below

[Chemical Formula 7]

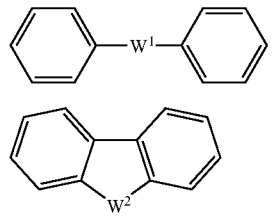

(3)

(4)

(where $W^1$ and $W^2$ each independently denote O, S, S(O) group, $S(O_2)$ group, or N, Si, P, or P(O) group with or without substituent group); n denotes the number of sulfonic acids connecting to A, the number being an integer that satisfies $1 \leq n \leq 4$; and q denotes the number of connections for X and B, the number being an integer that satisfies $1 \leq q$.]

B should preferably be a divalent or multivalent substituted or unsubstituted hydrocarbon group containing at least one aromatic ring, a divalent or trivalent 1,3,5-triazine group, or a substituted or unsubstituted divalent diphenylsulfone group. Particularly desirable ones include a divalent or trivalent substituted or unsubstituted benzyl group, a divalent substituted or unsubstituted p-xylylene group, a divalent or trivalent substituted or unsubstituted naphthyl group, a divalent or trivalent 1,3,5-triazine group, a divalent substituted or unsubstituted diphenylsulfone group, a di- to tetravalent perfluorobiphenyl group, a divalent substituted or unsubstituted 2,2-bis((hydroxypropoxy)phenyl)propyl group, and a substituted or unsubstituted polyvinylbenzyl group, which are selected to improve durability and charge transport ability.

The charge accepting dopant substance and the charge transport material should be mixed together in an adequate ratio which depends on the molecular structure of the charge accepting dopant, the molecular structure of the charge transport material, the molecular weight of the charge accepting dopant, the molecular weight of the charge transport material, and the intended conductivity of the conductive film. A desirable ratio is such that the molar ratio of NH (in the charge transport material) to $SO_3H$ (in the charge accepting dopant) is 1:0.01-20, preferably 1:0.05-10.

Especially in the case where the charge transport material and the charge accepting dopant according to the present invention are combined with the naphthalenedisulfonic acid oligomer (NSO-2) represented by the formula (26), which is a compound disclosed in WO 2006/025342 pamphlet, the adequate mixing molar ratio of the former to the latter should be 1:0.01-10.0, more preferably 1:0.05-4.0. The adequate mixing ratio is necessary for good transparency and EL characteristics. (The host in a decreased amount improves in transparency, and the host undergoes absorption in the visible region and easily brings about energy transfer from excitons.)

[Chemical Formula 8]

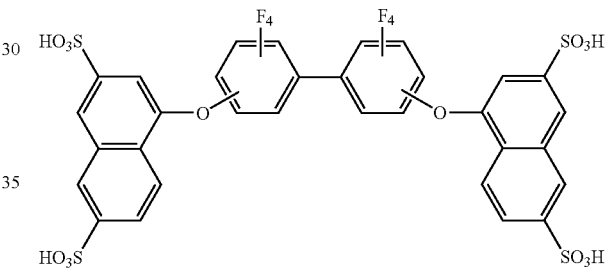

(26)

Typical examples of the hole accepting dopant include alkali metals (Li, Na, K, Cs) and metal complexes, such as lithium quinolinolato (Liq) and lithium acetylacetonate (Li (acac)). They are not limitative.

Also, the charge transport varnish according to the present invention may be incorporated with a silane compound se that the resulting EL device works at a low voltage and has an extended life and improved luminance characteristics.

This silane compound may be at least one species selected from dialkoxysilane compounds, trialkoxysilane compounds, tetraalkoxysilane compounds, and silicone compounds. It should preferably be one which dissolves in at least one species of solvents used for the charge tranport varnish.

The amount of the silane compound should be about 1 to 50 wt %, preferably 1 to 40 wt %, and more preferably 3 to 35 wt %, for the total amount of solids in the charge transport varnish. The silane compound in an excess amount would prevent the injection of current into the device.

The trialkoxysilane compounds include, for example, those which are represented by the formula (27).

$$Y^1Si(OY^2)_3 \quad (27)$$

(where $Y^1$ denotes a halogen atom, hydrogen atom, or $C_{1-12}$ alkyl group, $C_{2-12}$ alkenyl group, $C_{2-12}$ alkynyl group, aryl group, or heteroaryl group, which may be substituted with Z; $Y^2$ denotes a $C_{1-12}$ alkyl group; and Z denotes a halogen atom, hydrogen atom, $C_{1-12}$ haloalkyl group, $C_{1-12}$ alkyl group, hydroxyl group, mercapto group, amino group, $C_{1-12}$ haloalkoxy group, $C_{1-12}$ alkoxy group, $C_{2-12}$ alkenyl group, $C_{2-12}$ haloalkenyl group, $C_{2-12}$ alkynyl group, $C_{2-12}$ haloalkynyl group, $C_{1-12}$ alkylthio group, $C_{1-12}$ monoalkylamino group, $C_{1-12}$ dialkylamino group, glycidoxy group, $C_{1-12}$ alkylcarbonyl group, $C_{2-12}$ alkenylcarbonyl group, $C_{2-12}$ alkynylcarbonyl group, $C_{1-12}$ alkylcarbonyloxy group, $C_{2-12}$ alkenylcarbonyloxy group, $C_{2-12}$ alkynylcarbonyloxy group, aryl group, halogenated aryl group, heteroaryl group, or halogenated heteroaryl group.)

The dialkoxysilane compounds include, for example, those which are represented by the formula (28).

$$Y^3Y^4Si(OY^5)_2 \qquad (28)$$

(where $Y^3$ and $Y^4$ each independently denote a halogen atom, or a $C_{1-12}$ alkyl group, $C_{2-12}$ alkenyl group, $C_{2-12}$ alkynyl group, aryl group, or heteroaryl group, which may be substituted with Z; $Y^5$ denotes a $C_{1-12}$ alkyl group; and Z denotes a halogen atom, hydrogen atom, $C_{1-12}$ haloalkyl group, $C_{1-12}$ alkyl group, hydroxyl group, mercapto group, amino group, $C_{1-12}$ haloalkoxy group, $C_{1-12}$ alkoxy group, $C_{2-12}$ alkenyl group, $C_{2-12}$ haloalkenyl group, $C_{2-12}$ alkynyl group, $C_{2-12}$ haloalkynyl group, $C_{1-12}$ alkylthio group, $C_{1-12}$ monoalkylamino group, $C_{1-12}$ dialkylamino group, glycidoxy group, $C_{1-12}$ alkylcarbonyl group, $C_{2-12}$ alkenylcarbonyl group, $C_{2-12}$ alkynylcarbonyl group, $C_{1-12}$ alkylcarbonyloxy group, $C_{2-12}$ alkenylcarbonyloxy group, $C_{2-12}$ alkynylcarbonyloxy group, aryl group, halogenated aryl group, heteroaryl group, or halogenated heteroaryl group.)

The tetraalkoxysilane compounds include, for example, those which are represented by the formula (29).

$$Si(OY^6)_2 \qquad (29)$$

(where $Y^6$ denotes a $C_{1-12}$ alkyl group.)

The halogen atoms denoted by $Y^1$, $Y^3$, and $Y^4$ may be the same ones as listed for the formula (1); preferable among them are fluorine atoms.

The $C_{1-12}$ alkyl group which may be substituted with Z may be linear, branched, or cyclic. Its typical examples include the alkyl group, cycloalkyl group, and bicycloalkyl group listed as the monovalent hydrocarbon group for the formula (1). They also include s-butyl, n-pentyl, n-heptyl, n-nonyl, n-decyl, n-undecyl, n-dodecyl, c-propyl, c-butyl, c-pentyl, and c-hexyl groups.

The $C_{2-12}$ alkenyl group which may be substituted with Z includes, for example, those alkenyl groups listed as the monovalent hydrocarbon group for the formula (1).

The $C_{2-12}$ alkynyl group which may be substituted with Z includes, for example, an ethynyl group, 1-propynyl group, 2-propynyl group, 2-methyl-1-propynyl group, 1-methyl-2-propynyl, and 1-, 2-, or 3-butynyl group.

The aryl group which may be substituted with Z includes, for example, those aryl groups listed as the monovalent hydrocarbon group for the formula (1).

The heteroaryl group which may be substituted with Z includes, for example, a thiophen-2-yl group, furan-2-yl group, pyrrol-2-yl group, imidazol-2-yl group, pyridin-2-yl group, and pyrimidin-2-yl group.

Preferable among these groups as $Y^1$, $Y^3$, and $Y^4$ are a fluorine atom, a hydrogen atom, or a $C_{1-12}$ alkyl group, $C_{2-12}$ alkenyl group, $C_{2-12}$ alkynyl group, aryl group, or heteroaryl group which may be substituted with Z, in view of the extended life and improved luminance of the organic EL device.

Typical examples of the $C_{1-12}$ alkyl group, $C_{2-12}$ alkenyl group $C_{2-12}$ alkynyl group, aryl group, heteroaryl group, and halogen atom denoted by Z include the same ones as mentioned above.

Typical examples of the $C_{1-12}$ haloalkyl group include a trifluoromethyl group, 2,2,2-trifluoroethyl group, 1,1,2,2,2-pentafluoroethyl group, 3,3,3-trifluoropropyl group, 2,2,3,3,3-pentafluoropropyl group, perfluoropropyl group, heptafluoroisopropyl group, perfluorobutyl group, perfluoropentyl group, perfluorohexyl group, perfluoroheptyl group, perfluorooctyl group, perfluorononyl group, perfluorodecyl group, perfluoroundecyl group, perfluorododecyl group, and heptadecafluoro-1,1,2,2-tetrahydrodecyl group.

Typical examples of the $C_{1-12}$ haloalkoxyl group include a trifluoromethoxy group, 2,2,2-trifluoroethoxy group, 1,1,2,2,2-pentafluoroethoxy group, 3,3,3-trifluoropropoxy group, 2,2,3,3,3-pentafluoropropoxy group, perfluoropropoxy group, heptafluoroisopropoxy group, perfluorobutoxy group, perfluoropentyloxy group, perfluorohexyloxy group, perfluoroheptyloxy group, perfluorooctyloxy group, perfluorononyloxy group, perfluorodecyloxy group, perfluoroundecyloxy group, perfluorododecyloxy group, and heptadecafluoro-1,1,2,2-tetrahydrodecyloxy group.

Typical examples of the $C_{1-12}$ alkoxyl group include a methoxy group, ethoxy group, n-propoxy group, i-propoxy group, n-butoxy group, s-butoxy group, t-butoxy group, and n-pentoxy group.

Typical examples of the $C_{2-12}$ haloalkenyl group include a fluorovinyl group, difluorovinyl group, 3,3,3-trifluoro-1-propenyl group, 3,3,3-trifluoro-2-propenyl group, and 2-propenyl group.

Typical examples of the $C_{2-12}$ haloalkynyl group include a 3,3,3-trifluoro-1-propynyl group and 3,3,3-trifluoro-2-propynyl group.

Typical examples of the $C_{1-12}$ alkylthio group include those organothio groups which are listed for the formula (1).

Typical examples of the $C_{1-12}$ monoalkylamino group and dialkylamino group include those organoamino groups which are listed for the formula (1).

Typical examples of the $C_{1-12}$ alkylcarbonyl group include a methylcarbonyl group, ethylcarbonyl group, n-propylcarbonyl group, i-propylcarbonyl group, n-butylcarbonyl group, s-butylcarbonyl group, t-butylcarbonyl group, and n-pentylcarbonyl group.

Typical examples of the $C_{1-12}$ alkylcarbonyloxy group include a methylcarbonyloxy group, ethylcarbonyloxy group, n-propylcarbonyloxy group, i-propylcarbonyloxy group, n-butylcarbonyloxy group, s-butylcarbonyloxy group, t-butylcarbonyloxy group, and n-pentylcarbonyloxy group.

Typical examples of the $C_{2-12}$ alkenylcarbonyl group include a vinylcarbonyl group, 1-propenylcarbonyl group, 2-propenylcarbonyl group, 2-methyl-1-propenylcarbonyl group, and 1-methyl-2-propenylcarbonyl group.

Typical examples of the $C_{2-12}$ alkynylcarbonyl group include an ethynylcarbonyl group, 1-propynylcarbonyl group, 2-propynylcarbonyl group, 2-methyl-1-propynylcarbonyl group, and 1-methyl-2-propynylcarbonyl group.

Typical examples of the $C_{1-12}$ alkenylcarbonyloxy group include a vinylcarbonyloxy group, 1-propenylcarbonyloxy group, 2-propenylcarbonyloxy group, 2-methyl-1-propenylcarbonyloxy group, and 1-methyl-2-propenylcarbonyloxy group.

Typical examples of the $C_{1-12}$ alkynylcarbonyloxy group include an ethynylcarbonyloxy group, 1-propynylcarbonyloxy group, 2-propynylcarbonyloxy group, 2-methyl-1-propynyl-carbonyloxy group, and 1-methyl-2-propynylcarbonyloxy group.

Typical examples of the halogenated aryl group include a 1-fluorophenyl group, 2-fluorophenyl group, 3-fluorophenyl group, 4-fluorophehyl group, 5-fluorophenyl group, and pentafluorophenyl group.

Typical examples of the halogenated heteroaryl group include a 3-fluorothiophen-2-yl group, 4-fluorothiophen-2-yl group, and 5-fluorothiophen-2-yl group.

Preferable among these examples as Z are a halogen atom, hydrogen atom, $C_{1-12}$ haloalkyl group, $C_{1-12}$ alkyl group, $C_{2-12}$ alkenyl group, $C_{1-12}$ haloalkenyl group, $C_{2-12}$ alkynyl group, $C_{2-12}$ haloalkynyl group, aryl group, halogenated aryl group, heteroaryl group, and halogenated heteroaryl group, which are desirable for the extended life and improved luminance characteristics of the organic EL device.

The thin film formed from the varnish of the present invention permits fluorine atoms or a silane compound with fluorine-containing substituent groups to migrate to the surface thereof and to exist more in the vicinity of the surface thereof. Consequently, incorporating the varnish with a fluorine-containing silane compound makes it easy to adjust the surface energy of the thin film.

Therefore, the above-mentioned trialkoxysilane should preferably be one in which $Y^1$ is a fluorine atom or a fluorine-containing substituent group. Also, the above-mentioned dialkoxysilane should preferably be one in which at least either of $Y^3$ and $Y^4$ is a fluorine atom or a fluorine-containing substituent group.

The $C_{1-12}$ alkyl groups denoted by $Y^2$, $Y^5$, and $Y^6$ should preferably be $C_{1-5}$ alkyl groups, particularly methyl group, ethyl group and n-propyl group, which contribute to the extended life and improved luminance characteristics of the organic EL device.

Typical examples of the trialkoxysilane compound include methyltrimethoxysilane, methyltriethoxysilane, ethyltrimethoxysilane, ethyltriethoxysilane, propyltrimethoxysilane, propyltriethoxysilane, butyltrimethoxysilane, butyltriethoxysilane, pentyltrimethoxysilane, pentyltriethoxysilane, heptyltimethoxysilane, heptyltiethoxysilane, octyltrimethoxysilane, octyltriethoxysilane, dodecyltrimethoxysilane, dodecyltriethoxysilane, hexadecyltrimethoxysilane, hexadecyltriethoxysilane, octadecyltrimethoxysilane, octadecyltriethoxysilane, phenyltrimethoxysilane, phenyltriethoxysilane, vinyltrimethoxysilane, vinyltriethoxysilane, γ-aminopropyltrimethoxysilane, γ-aminopropyltriethoxysilane, γ-glycidoxypropyltrimethoxysilane, γ-glycidoxypropyltriethoxysilane, γ-methacryloxypropyltrimethoxysilane, γ-methacryloxypropyltriethoxysilane, triethoxy(4-(trifluoromethyl)phenyl)silane, dodecyltriethoxysilane, 3,3,3-trifluoropropyltrimethoxysilane, (triethoxysilyl)cyclohexane, perfluorooctylethyltriethoxysilane, triethoxyfluorosilane, tridecafluoro-1,1,2,2-tetrahydrooctyltriethoxysilane, pentafluorophenylpropyltrimethoxysilane, 3-(heptafluoroisopropoxy)propyltriethoxysilane, heptadecafluoro-1,1,2,2-tetrahydrodecyltriethoxysilane, triethoxy-2-thienylsilane, and 3-(triethoxysilyl)furan. They may be used alone or in combination with one another.

Preferred typical examples of the trialkoxysilane compound include methyltrimethoxysilane, methyltriethoxysilane, ethyltrimethoxysilane, ethyltriethoxysilane, propyltrimethoxysilane, propyltriethoxysilane, butyltrimethoxysilane, butyltriethoxysilane, phenyltrimethoxysilane, phenyltriethoxysilane, vinyltrimethoxysilane, vinyltriethoxysilane, γ-glycidoxypropyltrimethoxysilane, γ-glycidoxypropyltriethoxysilane, triethoxy(4-(trifluoromethyl)phenyl)silane, 3,3,3-trifluoropropyltrimethoxysilane, (triethoxysilyl)cyclohexane, perfluorooctylethyltriethoxysilane, triethoxyfluorosilane, tridecafluoro-1,1,2,2-tetrahydrooctyltriethoxysilane, pentafluorophenylpropyltrimethoxysilane, 3-(heptafluoroisopropoxy)propyltriethoxysilane, heptadecafluoro-1,1,2,2-tetrahydrodecyltriethoxysilane, triethoxy-2-thienylsilane, and 3-(triethoxysilyl)furan.

More preferred typical examples of the trialkoxysilane compound include methyltrimethoxysilane, methyltriethoxysilane, ethyltrimethoxysilane, ethyltriethoxysilane, propyltrimethoxysilane, propyltriethoxysilane, butyltrimethoxysilane, butyltriethoxysilane, phenyltrimethoxysilane, phenyltriethoxysilane, vinyltrimethoxysilane, vinyltriethoxysilane, triethoxy(4-(trifluoromethyl)phenyl)silane, 3,3,3-trifluoropropyltrimethoxysilane, (triethoxysilyl)cyclohexane, perfluorooctylethyltriethoxysilane, triethoxyfluorosilane, tridecafluoro-1,1,2,2-tetrahydrooctyltriethoxysilane, pentafluorophenylpropyltrimethoxysilane, 3-(heptafluoroisopropoxy)propyltriethoxysilane, heptadecafluoro-1,1,2,2-tetrahydrodecyltriethoxysilane, triethoxy-2-thienylsilane, and 3-(triethoxysilyl)furan.

Typical examples of the dialkoxysilane include methylhydrogendimethoxysilane, methylhydrogendiethoxysilane, dimethyldimethoxysilane, dimethyldiethoxysilane, methylethyldimethoxysilane, diethyldimethoxysilane, diethyldiethoxysilane, methylpropyldimethoxysilane, methylpropyldiethoxysilane, diisopropyldimethoxysilane, phenylmethyldimethoxysilane, vinylmethyldimethoxysilane, γ-glycidoxypropylmethyldimethoxysilane, γ-glycidoxypropylmethyldiethoxysilane, β-(3,4-epoxycyclohexyl)ethylmethyldimethoxysilane, γ-methacryloxypropylmethyldimethoxysilane, γ-methacryloxypropylmethyldiethoxysilane, γ-mercaptopropylmethyldimethoxysilane, γ-aminopropylmethyldiethoxysilane, N-(2-aminoethyl)aminopropylmethyldimethoxysilane, and 3,3,3-trifluoropropylmethyldimethoxysilane. They may be used alone or in combination with one another.

Preferred dialkoxysilane compounds include those, such as 3,3,3-trifluoropropylmethyldimethoxysilane, which contains fluorine atoms.

Typical examples of the tetralkoxysilane include tetraethoxysilane, tetramethoxysilane, and tetrapropoxysilane. They may be used alone or in combination with one another.

Typical examples of the silicone include dimethylsilicone oil, methylphenylsilicone oil, methylhydrogensilicone oil, alkyl-modified silicone oil, fluorine-modified silicone oil, polyether-modified silicone oil, alcohol-modified silicone oil, amino-modified silicone oil, epoxy-modified silicone oil, phenol-modified silicone oil, carboxy-modified silicone oil, mercapto-modified silicone, and methacrylate-modified silicone. They may be used alone or in combination with one another.

The charge transport varnish according to the present invention should preferably be incorporated with at least two species of the above-mentioned silane compounds, so that it gives rise to a highly flat thin film.

Preferred combinations of trialkoxysilane compounds are listed below.

(1) Methyltrimethoxysilane and phenyltrimethoxysilane, methyltrimethoxysilane and phenyltriethoxysilane, methyltrimethoxysilane and vinyltrimethoxysilane, methyltrimethoxysilane and vinyltriethoxysilane, methyltrimethoxysilane and γ-glycidoxypropyltrimethoxysilane, methyltrimethoxysilane and γ-glycidoxypropyltriethoxysilane, methyltrimethoxysilane and (triethoxysilyl)cyclohexane, methyltrimethoxysilane and p-tolyltrimethoxysilane, methyltrimethoxysilane and p-methoxyphenyltrimethoxysilane, methyltrimethoxysilane and triethoxy-2-thienylsilane, and methyltrimethoxysilane and 3-(triethoxysilyl)furan.

(2) Methyltriethoxysilane and phenyltrimethoxysilane, methyltriethoxysilane and phenyltriethoxysilane, methyltriethoxysilane and vinyltrimethoxysilane, methyltriethoxysilane and vinyltriethoxysilane, methyltriethoxysilane and γ-glycidoxypropyltrimethoxysilane, methyltriethoxysilane and γ-glycidoxypropyltriethoxysilane, methyltriethoxysilane and (triethoxysilyl)cyclohexane, methyltriethoxysilane and p-tolyltrimethoxysilane, methyltriethoxysilane and p-methoxyphenyltrimethoxysilane, methyltriethoxysilane and triethoxy-2-thienylsilane, and methyltriethoxysilane and 3-(triethoxysilyl)furan.

(3) Ethyltrimethoxysilane and phenyltrimethoxysilane, ethyltrimethoxysilane and phenyltriethoxysilane, ethyltrimethoxysilane and vinyltrimethoxysilane, ethyltrimethoxysilane and vinyltriethoxysilane, ethyltrimethoxysilane and γ-glycidoxypropyltrimethoxysilane, ethyltrimethoxysilane and γ-glycidoxypropyltriethoxysilane, ethyltrimethoxysilane and (triethoxysilyl)cyclohexane, ethyltrimethoxysilane and p-tolyltrimethoxysilane, ethyltrimethoxysilane and p-methoxyphenyltrimethoxysilane, ethyltrimethoxysilane and triethoxy-2-thienylsilane, and ethyltrimethoxysilane and 3-(triethoxysilyl)furan.

(4) Ethyltriethoxysilane and phenyltrimethoxysilane, ethyltriethoxysilane and phenyltriethoxysilane, ethyltriethoxysilane and vinyltrimethoxysilane, ethyltriethoxysilane and vinyltriethoxysilane, ethyltriethoxysilane and γ-glycidoxypropyltrimethoxysilane, ethyltriethoxysilane and γ-glycidoxypropyltriethoxysilane, ethyltriethoxysilane and (triethoxysilyl)cyclohexane, ethyltriethoxysilane and p-tolyltrimethoxysilane, ethyltriethoxysilane and p-methoxyphenyltrimethoxysilane, ethyltriethoxysilane and triethoxy-2-thienylsilane, and ethyltriethoxysilane and 3-(triethoxysilyl)furan.

(5) Propyltrimethoxysilane and phenyltrimethoxysilane, propyltrimethoxysilane and phenyltriethoxysilane, propyltrimethoxysilane and vinyltrimethoxysilane, propyltrimethoxysilane and vinyltriethoxysilane, propyltrimethoxysilane and γ-glycidoxypropyltrimethoxysilane, propyltrimethoxysilane and γ-glycidoxypropyltriethoxysilane, propyltrimethoxysilane and (triethoxysilyl)cyclohexane, propyltrimethoxysilane and p-tolyltrimethoxysilane, propyltrimethoxysilane and p-methoxyphenyltrimethoxysilane, propyltrimethoxysilane and triethoxy-2-thienylsilane, and propyltrimethoxysilane and 3-(triethoxysilyl)furan.

(6) Propyltriethoxysilane and phenyltrimethoxysilane, propyltriethoxysilane and phenyltriethoxysilane, propyltriethoxysilane and vinyltrimethoxysilane, propyltriethoxysilane and vinyltriethoxysilane, propyltriethoxysilane and γ-glycidoxypropyltrimethoxysilane, propyltriethoxysilane and γ-glycidoxypropyltriethoxysilane, propyltriethoxysilane and (triethoxysilyl)cyclohexane, propyltriethoxysilane and p-tolyltrimethoxysilane, propyltriethoxysilane and p-methoxyphenyltrimethoxysilane, propyltriethoxysilane and triethoxy-2-thienylsilane, and propyltriethoxysilane and 3-(triethoxysilyl)furan.

(7) Butyltrimethoxysilane and phenyltrimethoxysilane, butyltrimethoxysilane and phenyltriethoxysilane, butyltrimethoxysilane and vinyltrimethoxysilane, butyltrimethoxysilane and vinyltriethoxysilane, butyltrimethoxysilane and γ-glycidoxypropyltrimethoxysilane, butyltrimethoxysilane and γ-glycidoxypropyltriethoxysilane, butyltrimethoxysilane and (triethoxysilyl)cyclohexane, butyltrimethoxysilane and p-tolyltrimethoxysilane, butyltrimethoxysilane and p-methoxyphenyltrimethoxysilane, butyltrimethoxysilane and triethoxy-2-thienylsilane, and butyltrimethoxysilane and 3-(triethoxysilyl)furan.

(8) Butyltriethoxysilane and phenyltrimethoxysilane, butyltriethoxysilane and phenyltriethoxysilane, butyltriethoxysilane and vinyltrimethoxysilane, butyltriethoxysilane and vinyltriethoxysilane, butyltriethoxysilane and γ-glycidoxypropyltrimethoxysilane, butyltriethoxysilane and γ-glycidoxypropyltriethoxysilane, butyltriethoxysilane and (triethoxysilyl)cyclohexane, butyltriethoxysilane and p-tolyltrimethoxysilane, butyltriethoxysilane and p-methoxyphenyltrimethoxysilane, butyltriethoxysilane and triethoxy-2-thienylsilane, and butyltriethoxysilane and 3-(triethoxysilyl)furan.

(9) Triethoxy(4-(trifluoromethyl)phenyl)silane and phenyltrimethoxysilane, triethoxy(4-trifluoromethyl)phenyl)silane and phenyltriethoxysilane, triethoxy(4-(trifluoromethyl)phenyl)silane and vinyltrimethoxysilane, triethoxy(4-(trifluoromethyl)phenyl)silane and vinyltriethoxysilane, triethoxy(4-(trifluoromethyl)phenyl)silane and γ-glycidoxypropyltrimethoxysilane, triethoxy(4-(trifluoromethyl)phenyl)silane and γ-glycidoxypropyltriethoxysilane, triethoxy(4-(trifluoromethyl)phenyl)silane and (triethoxysilyl)cyclohexane, triethoxy(4-(trifluoromethyl)phenyl)silane and p-tolyltrimethoxysilane, triethoxy(4-(trifluoromethyl)phenyl)silane and p-methoxyphenyltrimethoxysilane, triethoxy(4-(trifluoromethyl)phenyl)silane and triethoxy-2-thienylsilane, and triethoxy(4-(trifluoromethyl)phenyl)silane and 3-(triethoxysilyl)furan.

(10) Butyltriethoxysilane and phenyltrimethoxysilane, butyltriethoxysilane and phenyltriethoxysilane, butyltriethoxysilane and vinyltrimethoxysilane, butyltriethoxysilane and vinyltriethoxysilane, butyltriethoxysilane and γ-glycidoxypropyltrimethoxysilane, butyltriethoxysilane and γ-glycidoxypropyltriethoxysilane, butyltriethoxysilane and (triethoxysilyl)cyclohexane, butyltriethoxysilane and p-tolyltrimethoxysilane, butyltriethoxysilane and p-methoxyphenyltrimethoxysilane, butyltriethoxysilane and triethoxy-2-thienylsilane, and butyltriethoxysilane and 3-(triethoxysilyl)furan.

(11) 3,3,3-trifluoropropyltrimethoxysilane and phenyltrimethoxysilane, 3,3,3-trifluoropropyltrimethoxysilane and phenyltriethoxysilane, 3,3,3-trifluoropropyltrimethoxysilane and vinyltrimethoxysilane, 3,3,3-trifluoropropyltrimethoxysilane and vinyltriethoxysilane, 3,3,3-trifluoropropyltrimethoxysilane and γ-glycidoxypropyltrimethoxysilane, 3,3,3-trifluoropropyltrimethoxysilane and γ-glycidoxypropyltriethoxysilane, 3,3,3-trifluoropropyltrimethoxysilane and (triethoxysilyl)cyclohexane, 3,3,3-trifluoropropyltrimethoxysilane and p-tolyltrimethoxysilane, 3,3,3-trifluoropropyltrimethoxysilane and p-methoxyphenyltrimethoxysilane, 3,3,3-trifluoropropyltrimethoxysilane and triethoxy-2-thienylsilane, and 3,3,3-trifluoropropyltrimethoxysilane and 3-(triethoxysilyl)furan.

(12) Perfluorooctylethyltriethoxysilane and phenyltrimethoxysilane, perfluorooctylethyltriethoxysilane and phenyltriethoxysilane, perfluorooctylethyltriethoxysilane and vinyltrimethoxysilane, perfluorooctylethyltriethoxysilane and vinyltriethoxysilane, perfluorooctylethyltriethoxysilane and γ-glycidoxypropyltrimethoxysilane, perfluorooctylethyltriethoxysilane and γ-glycidoxypropyltriethoxysilane, perfluorooctylethyltriethoxysilane and (triethoxysilyl)cyclohexane, perfluorooctylethyltriethoxysilane and p-tolyltrimethoxysilane, perfluorooctylethyltriethoxysilane and p-methoxyphenyltrimethoxysilane, perfluorooctylethyltriethoxysilane and triethoxy-2-thienylsilane, and perfluorooctylethyltriethoxysilane and 3-(triethoxysilyl)furan.

(13) Triethoxyfluorosilane and phenyltrimethoxysilane, triethoxyfluorosilane and phenyltriethoxysilane, triethoxyfluorosilane and vinyltrimethoxysilane, triethoxyfluorosilane and vinyltriethoxysilane, triethoxyfluorosilane and γ-glycidoxypropyltrimethoxysilane, triethoxyfluorosilane and γ-glycidoxypropyltriethoxysilane, triethoxyfluorosilane and (triethoxysilyl)cyclohexane, triethoxyfluorosilane and p-tolyltrimethoxysilane, triethoxyfluorosilane and p-methoxyphenyltrimethoxysilane, triethoxyfluorosilane and triethoxy-2-thienylsilane, and triethoxyfluorosilane and 3-(triethoxysilyl)furan.
(14) Tridecafluoro-1,1,2,2-tetrahydrooctyltriethoxysilane and phenyltrimethoxysilane, tridecafluoro-1,1,2,2-tetrahydrooctyltriethoxysilane and phenyltriethoxysilane, tridecafluoro-1,1,2,2-tetrahydrooctyltriethoxysilane and vinyltrimethoxysilane, tridecafluoro-1,1,2,2-tetrahydrooctyltriethoxysilane and vinyltriethoxysilane, tridecafluoro-1,1,2,2-tetrahydrooctyltriethoxysilane and γ-glycidoxypropyltrimethoxysilane, tridecafluoro-1,1,2,2-tetrahydrooctyltriethoxysilane and γ-glycidoxypropyltriethoxysilane, tridecafluoro-1,1,2,2-tetrahydrooctyltriethoxysilane and (triethoxysilyl)cyclohexane, tridecafluoro-1,1,2,2-tetrahydrooctyltriethoxysilane and p-tolyltrimethoxysilane, tridecafluoro-1,1,2,2-tetrahydrooctyltriethoxysilane and p-methoxyphenyltrimethoxysilane, tridecafluoro-1,1,2,2-tetrahydrooctyltriethoxysilane and triethoxy-2-thienylsilane, and tridecafluoro-1,1,2,2-tetrahydrooctyltriethoxysilane and 3-(triethoxysilyl)furan.
(15) 3-(heptafluoroisopropoxy)propyltriethoxysilane and phenyltrimethoxysilane, 3-(heptafluoroisopropoxy)propyltriethoxysilane and phenyltriethoxysilane, 3-(heptafluoroisopropoxy)propyltriethoxysilane and vinyltrimethoxysilane, 3-(heptafluoroisopropoxy)propyltriethoxysilane and vinyltriethoxysilane, 3-(heptafluoroisopropoxy)propyltriethoxysilane and γ-glycidoxypropyltrimethoxysilane, 3-(heptafluoroisopropoxy)propyltriethoxysilane and γ-glycidoxypropyltriethoxysilane, 3-(heptafluoroisopropoxy)propyltriethoxysilane and (triethoxysilyl)cyclohexane, 3-(heptafluoroisopropoxy)propyltriethoxysilane and p-tolyltrimethoxysilane, 3-(heptafluoroisopropoxy)propyltriethoxysilane and p-methoxyphenyltrimethoxysilane, 3-(heptafluoroisopropoxy)propyltriethoxysilane and triethoxy-2-thienylsilane, and 3-(heptafluoroisopropoxy)propyltriethoxysilane and 3-(triethoxysilyl)furan.
(16) Heptadecafluoro-1,1,2,2-tetrahydrodecyltriethoxysilane and phenyltrimethoxysilane, heptadecafluoro-1,1,2,2-tetrahydrodecyltriethoxysilane and phenyltriethoxysilane, heptadecafluoro-1,1,2,2-tetrahydrodecyltriethoxysilane and vinyltrimethoxysilane, heptadecafluoro-1,1,2,2-tetrahydrodecyltriethoxysilane and vinyltriethoxysilane, heptadecafluoro-1,1,2,2-tetrahydrodecyltriethoxysilane and γ-glycidoxypropyltrimethoxysilane, heptadecafluoro-1,1,2,2-tetrahydrodecyltriethoxysilane and γ-glycidoxypropyltriethoxysilane, heptadecafluoro-1,1,2,2-tetrahydrodecyltriethoxysilane and (triethoxysilyl)cyclohexane, heptadecafluoro-1,1,2,2-tetrahydrodecyltriethoxysilane and p-tolyltrimethoxysilane, heptadecafluoro-1,1,2,2-tetrahydrodecyltriethoxysilane and p-methoxyphenyltrimethoxysilane, heptadecafluoro-1,1,2,2-tetrahydrodecyltriethoxysilane and triethoxy-2-thienylsilane, and heptadecafluoro-1,1,2,2-tetrahydrodecyltriethoxysilane and 3-(triethoxysilyl)furan.
(17) Triethoxy-2-thienylsilane and phenyltrimethoxysilane, triethoxy-2-thienylsilane and phenyltriethoxysilane, triethoxy-2-thienylsilane and vinyltrimethoxysilane, triethoxy-2-thienylsilane and vinyltriethoxysilane, triethoxy-2-thienylsilane and γ-glycidoxypropyltrimethoxysilane, triethoxy-2-thienylsilane and γ-glycidoxypropyltriethoxysilane, triethoxy-2-thienylsilane and (triethoxysilyl)cyclohexane, triethoxy-2-thienylsilane and p-tolyltrimethoxysilane, triethoxy-2-thienylsilane and p-methoxyphenyltrimethoxysilane, and triethoxy-2-thienylsilane and 3-(triethoxysilyl)furan.
(18) 3-(triethoxysilyl)furan and phenyltrimethoxysilane, 3-(triethoxysilyl)furan and phenyltriethoxysilane, 3-(triethoxysilyl)furan and vinyltrimethoxysilane, 3-(triethoxysilyl)furan and vinyltriethoxysilane, 3-(triethoxysilyl)furan and γ-glycidoxypropyltrimethoxysilane, 3-(triethoxysilyl)furan and γ-glycidoxypropyltriethoxysilane, 3-(triethoxysilyl)furan and (triethoxysilyl)cyclohexane, 3-(triethoxysilyl)furan and p-tolyltrimethoxysilane, 3-(triethoxysilyl)furan and p-methoxyphenyltrimethoxysilane, and 3-(triethoxysilyl)furan and triethoxy-2-thienylsilane.
(19) Phenyltrimethoxysilane and phenyltriethoxysilane, phenyltrimethoxysilane and vinyltrimethoxysilane, phenyltrimethoxysilane and vinyltriethoxysilane, phenyltrimethoxysilane and γ-glycidoxypropyltrimethoxysilane, phenyltrimethoxysilane and γ-glycidoxypropyltriethoxysilane; phenyltrimethoxysilane and (triethoxysilyl)cyclohexane, phenyltrimethoxysilane and p-tolyltrimethoxysilane, phenyltrimethoxysilane and p-methoxyphenyltrimethoxysilane, phenyltrimethoxysilane and triethoxy-2-thienylsilane, and phenyltrimethoxysilane and 3-(triethoxysilyl)furan.
(20) Phenyltriethoxysilane and phenyltrimethoxysilane, phenyltriethoxysilane and vinyltrimethoxysilane, phenyltriethoxysilane and vinyltriethoxysilane, phenyltriethoxysilane and γ-glycidoxypropyltrimethoxysilane, phenyltriethoxysilane and γ-glycidoxypropyltriethoxysilane, phenyltriethoxysilane and (triethoxysilyl)cyclohexane, phenyltriethoxysilane and p-tolyltrimethoxysilane, phenyltriethoxysilane and p-methoxyphenyltrimethoxysilane, phenyltriethoxysilane and triethoxy-2-thienylsilane, and phenyltriethoxysilane and 3-(triethoxysilyl)furan.
(21) Vinyltrimethoxysilane and phenyltrimethoxysilane, vinyltrimethoxysilane and phenyltriethoxysilane, vinyltrimethoxysilane and vinyltriethoxysilane, vinyltrimethoxysilane and γ-glycidoxypropyltrimethoxysilane, vinyltrimethoxysilane and γ-glycidoxypropyltriethoxysilane, vinyltrimethoxysilane and (triethoxysilyl)cyclohexane, vinyltrimethoxysilane and p-tolyltrimethoxysilane, vinyltrimethoxysilane and p-methoxyphenyltrimethoxysilane, vinyltrimethoxysilane and triethoxy-2-thienylsilane, and vinyltrimethoxysilane and 3-(triethoxysilyl)furan.
(22) Vinyltriethoxysilane and phenyltrimethoxysilane, vinyltriethoxysilane and phenyltriethoxysilane, vinyltriethoxysilane and vinyltrimethoxysilane, vinyltriethoxysilane and γ-glycidoxypropyltrimethoxysilane, vinyltriethoxysilane and γ-glycidoxypropyltriethoxysilane, vinyltriethoxysilane and (triethoxysilyl)cyclohexane, vinyltriethoxysilane and p-tolyltrimethoxysilane, vinyltriethoxysilane and p-methoxyphenyltrimethoxysilane, vinyltriethoxysilane and triethoxy-2-thienylsilane, and vinyltriethoxysilane and 3-(triethoxysilyl)furan.
(23) γ-glycidoxypropyltrimethoxysilane and phenyltrimethoxysilane, γ-glycidoxypropyltrimethoxysilane and phenyltriethoxysilane, γ-glycidoxypropyltrimethoxysilane and vinyltrimethoxysilane, γ-glycidoxypropyltrimethoxysilane and vinyltriethoxysilane, γ-glycidoxypropyltrimethoxysilane and γ-glycidoxypropyltrimethoxysilane, γ-glycidoxypropyltrimethoxysilane and (triethoxysilyl)cyclohexane, γ-glycidoxypropyltrimethoxysilane and p-tolyltrimethoxysilane, γ-glycidoxypropyltrimethoxysilane and p-methoxyphenyltrimethoxysilane, γ-glycidoxypropyltrimethoxysilane and triethoxy-2-thienylsilane, and 3-(triethoxysilyl)furan.

(24) γ-glycidoxypropyltriethoxysilane and phenyltrimethoxysilane, γ-glycidoxypropyltriethoxysilane and phenyltriethoxysilane, γ-glycidoxypropyltriethoxysilane and vinyltrimethoxysilane, γ-glycidoxypropyltriethoxysilane and vinyltriethoxysilane, γ-glycidoxypropyltriethoxysilane and γ-glycidoxypropyltrimethoxysilane, γ-glycidoxypropyltriethoxysilane and (triethoxysilyl)cyclohexane, γ-glycidoxypropyltriethoxysilane and p-tolyltrimethoxysilane, γ-glycidoxypropyltriethoxysilane and p-methoxyphenyltrimethoxysilane, γ-glycidoxypropyltriethoxysilane and triethoxy-2-thienylsilane, and γ-glycidoxypropyltriethoxysilane and 3-(triethoxysilyl)furan.

(25) (Triethoxysilyl)cyclohexane and phenyltrimethoxysilane, (triethoxysilyl)cyclohexane and phenyltriethoxysilane, (triethoxysilyl)cyclohexane and vinyltrimethoxysilane, (triethoxysilyl)cyclohexane and vinyltriethoxysilane, (triethoxysilyl)cyclohexane and γ-glycidoxypropyltrimethoxysilane, (triethoxysilyl)cyclohexane and γ-glycidoxypropyltriethoxysilane, (triethoxysilyl)cyclohexane and p-tolyltrimethoxysilane, (triethoxysilyl)cyclohexane and p-methoxyphenyltrimethoxysilane, (triethoxysilyl)cyclohexane and triethoxy-2-thienylsilane, and (triethoxysilyl)cyclohexane and 3-(triethoxysilyl)furan.

(26) p-tolyltrimethoxysilane and phenyltrimethoxysilane, p-tolyltrimethoxysilane and phenyltriethoxysilane, p-tolyltrimethoxysilane and vinyltrimethoxysilane, p-tolyltrimethoxysilane and vinyltriethoxysilane, p-tolyltrimethoxysilane and γ-glycidoxypropyltrimethoxysilane, p-tolyltrimethoxysilane and γ-glycidoxypropyltriethoxysilane, p-tolyltrimethoxysilane and (triethoxysilyl)cyclohexane, p-tolyltrimethoxysilane and p-methoxyphenyltrimethoxysilane, p-tolyltrimethoxysilane and triethoxy-2-thienylsilane, and p-tolyltrimethoxysilane and 3-(triethoxysilyl)furan.

(27) p-methoxyphenyltrimethoxysilane and phenyltrimethoxysilane, p-methoxyphenyltrimethoxysilane and phenyltriethoxysilane, p-methoxyphenyltrimethoxysilane and vinyltrimethoxysilane, p-methoxyphenyltrimethoxysilane and vinyltriethoxysilane, p-methoxyphenyltrimethoxysilane and γ-glycidoxypropyltrimethoxysilane, p-methoxyphenyltrimethoxysilane and γ-glycidoxypropyltriethoxysilane, p-methoxyphenyltrimethoxysilane and (triethoxysilyl)cyclohexane, p-methoxyphenyltrimethoxysilane and p-tolylmethoxysilane, p-methoxyphenyltrimethoxysilane and triethoxy-2-thienylsilane, and p-methoxyphenyltrimethoxysilane and 3-(triethoxysilyl)furan.

More preferred combinations of compounds are listed below.

(28) Methyltrimethoxysilane and phenyltrimethoxysilane, methyltrimethoxysilane and phenyltriethoxysilane, methyltrimethoxysilane and vinyltrimethoxysilane, methyltrimethoxysilane and vinyltriethoxysilane, methyltrimethoxysilane and (triethoxysilyl)cyclohexane, methyltrimethoxysilane and p-tolyltrimethoxysilane, methyltrimethoxysilane and p-methoxyphenyltrimethoxysilane, methyltrimethoxysilane and triethoxy-2-thienylsilane, and methyltrimethoxysilane and 3-(triethoxysilyl)furan.

(29) Methyltriethoxysilane and phenyltrimethoxysilane, methyltriethoxysilane and phenyltriethoxysilane, methyltriethoxysilane and vinyltrimethoxysilane, methyltriethoxysilane and vinyltriethoxysilane, methyltriethoxysilane and (triethoxysilyl)cyclohexane, methyltriethoxysilane and p-tolyltrimethoxysilane, methyltriethoxysilane and p-methoxyphenyltrimethoxysilane, methyltriethoxysilane and triethoxy-2-thienylsilane, and methyltriethoxysilane and 3-(triethoxysilyl)furan.

(30) Ethyltrimethoxysilane and phenyltrimethoxysilane, ethyltrimethoxysilane and phenyltriethoxysilane, ethyltrimethoxysilane and vinyltrimethoxysilane, ethyltrimethoxysilane and vinyltriethoxysilane, ethyltrimethoxysilane and (triethoxysilyl)cyclohexane, ethyltrimethoxysilane and p-tolyltrimethoxysilane, ethyltrimethoxysilane and p-methoxyphenyltrimethoxysilane, ethyltrimethoxysilane and triethoxy-2-thienylsilane, and ethyltrimethoxysilane and 3-(triethoxysilyl)furan.

(31) Ethyltriethoxysilane and phenyltrimethoxysilane, ethyltriethoxysilane and phenyltriethoxysilane, ethyltriethoxysilane and vinyltrimethoxysilane, ethyltriethoxysilane and vinyltriethoxysilane, ethyltriethoxysilane and (triethoxysilyl)cyclohexane, ethyltriethoxysilane and p-tolyltrimethoxysilane, ethyltriethoxysilane and p-methoxyphenyltrimethoxysilane, ethyltriethoxysilane and triethoxy-2-thienylsilane, and ethyltriethoxysilane and 3-(triethoxysilyl)furan.

(32) Propyltrimethoxysilane and phenyltrimethoxysilane, propyltrimethoxysilane and phenyltriethoxysilane, propyltrimethoxysilane and vinyltrimethoxysilane, propyltrimethoxysilane and vinyltriethoxysilane, propyltrimethoxysilane and (triethoxysilyl)cyclohexane, propyltrimethoxysilane and p-tolyltrimethoxysilane, propyltrimethoxysilane and p-methoxyphenyltrimethoxysilane, propyltrimethoxysilane and triethoxy-2-thienylsilane, and propyltrimethoxysilane and 3-(triethoxysilyl)furan.

(33) Propyltriethoxysilane and phenyltrimethoxysilane, propyltriethoxysilane and phenyltriethoxysilane, propyltriethoxysilane and vinyltrimethoxysilane, propyltriethoxysilane and vinyltriethoxysilane, propyltriethoxysilane and (triethoxysilyl)cyclohexane, propyltriethoxysilane and p-tolyltrimethoxysilane, propyltriethoxysilane and p-methoxyphenyltrimethoxysilane, propyltriethoxysilane and triethoxy-2-thienylsilane, and propyltriethoxysilane and 3-(triethoxysilyl)furan.

(34) Butyltrimethoxysilane and phenyltrimethoxysilane, butyltrimethoxysilane and phenyltriethoxysilane, butyltrimethoxysilane and vinyltrimethoxysilane, butyltrimethoxysilane and vinyltriethoxysilane, butyltrimethoxysilane and (triethoxysilyl)cyclohexane, butyltrimethoxysilane and p-tolyltrimethoxysilane, butyltrimethoxysilane and p-methoxyphenyltrimethoxysilane, butyltrimethoxysilane and triethoxy-2-thienylsilane, and butyltrimethoxysilane and 3-(triethoxysilyl)furan.

(35) Butyltriethoxysilane and phenyltrimethoxysilane, butyltriethoxysilane and phenyltriethoxysilane, butyltriethoxysilane and vinyltrimethoxysilane, butyltriethoxysilane and vinyltriethoxysilane, butyltriethoxysilane and (triethoxysilyl)cyclohexane, butyltriethoxysilane and p-tolyltrimethoxysilane, butyltriethoxysilane and p-methoxyphenyltrimethoxysilane, butyltriethoxysilane and triethoxy-2-thienylsilane, and butyltriethoxysilane and 3-(triethoxysilyi)furan.

(36) Triethoxy(4-(trifluoromethyl)phenyl)silane and phenyltrimethoxysilane, triethoxy(4-(trifluoromethyl)phenyl)silane and phenyltriethoxysilane, triethoxy(4-(trifluoromethyl)phenyl)silane and vinyltrimethoxysilane, triethoxy(4-(trifluoromethyl)phenyl)silane and vinyltriethoxysilane, triethoxy(4-(trifluoromethyl)phenyl)silane and (triethoxysilyl)cyclohexane, triethoxy(4-(trifluoromethyl)phenyl)silane and p-tolyltrimethoxysilane, triethoxy(4-(trifluoromethyl)phenyl)silane and p-methoxyphenyltrimethoxysilane, triethoxy(4-(trifluoromethyl)phenyl)silane and triethoxy-2-thienylsilane, and triethoxy(4-(trifluoromethyl)phenyl)silane and 3-(triethoxysilyl)furan.

(37) Butyltriethoxysilane and phenyltrimethoxysilane, butyltriethoxysilane and phenyltriethoxysilane, butyltriethoxysilane and vinyltrimethoxysilane, butyltriethoxysilane and vinyltriethoxysilane, butyltriethoxysilane and (triethoxysilyl)cyclohexane, butyltriethoxysilane and p-tolyltrimethoxysilane, butyltriethoxysilane and p-methoxyphenyltrimethoxysilane, butyltriethoxysilane and triethoxy-2-thienylsilane, and butyltriethoxysilane and 3-(triethoxysilyl)furan.

(38) 3,3,3-trifluoropropyltrimethoxysilane and phenyltrimethoxysilane, 3,3,3-trifluoropropyltrimethoxysilane and phenyltriethoxysilane, 3,3,3-trifluoropropyltrimethoxysilane and vinyltrimethoxysilane, 3,3,3-trifluoropropyltrimethoxysilane and vinyltriethoxysilane, 3,3,3-trifluoropropyltrimethoxysilane and (triethoxysilyl)cyclohexane, 3,3,3-trifluoropropyltrimethoxysilane and p-tolyltrimethoxysilane, 3,3,3-trifluoropropyltrimethoxysilane and p-methoxyphenyltrimethoxysilane, 3,3,3-trifluoropropyltrimethoxysilane and triethoxy-2-thienylsilane, and 3,3,3-trifluoropropyltrimethoxysilane and 3-(triethoxysilyl)furan.

(39) Perfluorooctylethyltriethoxysilane and phenyltrimethoxysilane, perfluorooctylethyltriethoxysilane and phenyltriethoxysilane, perfluorooctylethyltriethoxysilane and vinyltrimethoxysilane, perfluorooctylethyltriethoxysilane and vinyltriethoxysilane, perfluorooctylethyltriethoxysilane and (triethoxysilyl)cyclohexane, perfluorooctylethyltriethoxysilane and p-tolyltrimethoxysilane, perfluorooctylethyltriethoxysilane and p-methoxyphenyltrimethoxysilane, perfluorooctylethyltriethoxysilane and triethoxy-2-thienylsilane, and perfluorooctylethyltriethoxysilane and 3-(triethoxysilyl)furan.

(40) Triethoxyfluorosilane and phenyltrimethoxysilane, triethoxyfluorosilane and phenyltriethoxysilane, triethoxyfluorosilane and vinyltrimethoxysilane, triethoxyfluorosilane and vinyltriethoxysilane, triethoxyfluorosilane and (triethoxysilyl)cyclohexane, triethoxyfluorosilane and p-tolyltrimethoxysilane, triethoxyfluorosilane and p-methoxyphenyltrimethoxysilane, triethoxyfluorosilane and triethoxy-2-thienylsilane, and triethoxyfluorosilane and 3-(triethoxysilyl)furan.

(41) Tridecafluoro-1,1,2,2-tetrahydrooctyltriethoxysilane and phenyltrimethoxysilane, tridecafluoro-1,1,2,2-tetrahydrooctyltriethoxysilane and phenyltriethoxysilane, tridecafluoro-1,1,2,2-tetrahydrooctyltriethoxysilane and vinyltrimethoxysilane, tridecafluoro-1,1,2,2-tetrahydrooctyltriethoxysilane and vinyltriethoxysilane, tridecafluoro-1,1,2,2-tetrahydrooctyltriethoxysilane and (triethoxysilyl)cyclohexane, tridecafluoro-1,1,2,2-tetrahydrooctyltriethoxysilane and p-tolyltrimethoxysilane, tridecafluoro-1,1,2,2-tetrahydrooctyltriethoxysilane and p-methoxyphenyltrimethoxysilane, tridecafluoro-1,1,2,2-tetrahydrooctyltriethoxysilane and triethoxy-2-thienylsilane, and tridecafluoro-1,1,2,2-tetrahydrooctyltriethoxysilane and 3-(triethoxysilyl)furan.

(42) 3-(heptafluoroisopropoxy)propyltriethoxysilane and phenyltrimethoxysilane, 3-(heptafluoroisopropoxy)propyltriethoxysilane and phenyltriethoxysilane, 3-(heptafluoroisopropoxy)propyltriethoxysilane and vinyltrimethoxysilane, 3-(heptafluoroisopropoxy)propyltriethoxysilane and vinyltriethoxysilane, 3-(heptafluoroisopropoxy)propyltriethoxysilane and (triethoxysilyl)cyclohexane, 3-(heptafluoroisopropoxy)propyltriethoxysilane and p-tolyltrimethoxysilane, 3-(heptafluoroisopropoxy)propyltriethoxysilane and p-methoxyphenyltrimethoxysilane, 3-(heptafluoroisopropoxy)propyltriethoxysilane and triethoxy-2-thienylsilane, and 3-(heptafluoroisopropoxy)propyltriethoxysilane and 3-(triethoxysilyl)furan.

(43) Heptadecafluoro-1,1,2,2-tetrahydrodecyltriethoxysilane and phenyltrimethoxysilane, heptadecafluoro-1,1,2,2-tetrahydrodecyltriethoxysilane and phenyltriethoxysilane, heptadecafluoro-1,1,2,2-tetrahydrodecyltriethoxysilane and vinyltrimethoxysilane, heptadecafluoro-1,1,2,2-tetrahydrodecyltriethoxysilane and vinyltriethoxysilane, heptadecafluoro-1,1,2,2-tetrahydrodecyltriethoxysilane and (triethoxysilyl)cyclohexane, heptadecafluoro-1,1,2,2-tetrahydrodecyltriethoxysilane and p-tolyltrimethoxysilane, heptadecafluoro-1,1,2,2-tetrahydrodecyltriethoxysilane and p-methoxyphenyltrimethoxysilane, heptadecafluoro-1,1,2,2-tetrahydrodecyltriethoxysilane and triethoxy-2-thienylsilane, and 3-(triethoxysilyl)furan.

(44) Triethoxy-2-thienylsilane and phenyltrimethoxysilane, triethoxy-2-thienylsilane and phenyltriethoxysilane, triethoxy-2-thienylsilane and vinyltrimethoxysilane, triethoxy-2-thienylsilane and vinyltriethoxysilane, triethoxy-2-thienylsilane and (triethoxysilyl)cyclohexane, triethoxy-2-thienylsilane and p-tolyltrimethoxysilane, triethoxy-2-thienylsilane and p-methoxyphenyltrimethoxysilane, and triethoxy-2-thienylsilane and 3-(triethoxysilyl)furan.

(45) 3-(triethoxysilyl)furan and phenyltrimethoxysilane, 3-(triethoxysilyl)furan and phenyltriethoxysilane, 3-(triethoxysilyl)furan and vinyltrimethoxysilane, 3-(triethoxysilyl)furan and vinyltriethoxysilane, 3-(triethoxysilyl)furan and (triethoxysilyl)cyclohexane, 3-(triethoxysilyl)furan and p-tolyltrimethoxysilane, 3-(triethoxysilyl)furan and p-methoxyphenyltrimethoxysilane, and 3-(triethoxysilyl)furan and triethoxy-2-thienylsilane.

(46) Phenyltrimethoxysilane and phenyltriethoxysilane, phenyltrimethoxysilane and vinyltrimethoxysilane, phenyltrimethoxysilane and vinyltriethoxysilane, phenyltrimethoxysilane and (triethoxysilyl)cyclohexane, phenyltrimethoxysilane and p-tolyltrimethoxysilane, phenyltrimethoxysilane and p-methoxyphenyltrimethoxysilane, phenyltrimethoxysilane and triethoxy-2-thienylsilane, and phenyltrimethoxysilane and 3-(triethoxysilyl)furan.

(47) Phenyltriethoxysilane and phenyltrimethoxysilane, phenyltriethoxysilane and vinyltrimethoxysilane, phenyltriethoxysilane and vinyltriethoxysilane, phenyltriethoxysilane and (triethoxysilyl)cyclohexane, phenyltriethoxysilane and p-tolyltrimethoxysilane, phenyltriethoxysilane and p-methoxyphenyltrimethoxysilane, phenyltriethoxysilane and triethoxy-2-thienylsilane, and phenyltriethoxysilane and 3-(triethoxysilyl)furan.

(48) Vinyltrimethoxysilane and phenyltrimethoxysilane, vinyltrimethoxysilane and phenyltriethoxysilane, vinyltrimethoxysilane and vinyltriethoxysilane, vinyltrimethoxysilane and (triethoxysilyl)cyclohexane, vinyltrimethoxysilane and p-tolyltrimethoxysilane, vinyltrimethoxysilane and p-methoxyphenyltrimethoxysilane, vinyltrimethoxysilane and triethoxy-2-thienylsilane, and vinyltrimethoxysilane and 3-(triethoxysilyl)furan.

(49) Vinyltriethoxysilane and phenyltrimethoxysilane, vinyltriethoxysilane and phenyltriethoxysilane, vinyltriethoxysilane and vinyltrimethoxysilane, vinyltriethoxysilane and (triethoxysilyl)cyclohexane, vinyltriethoxysilane and p-tolyltrimethoxysilane, vinyltriethoxysilane and p-methoxyphenyltrimethoxysilane, vinyltriethoxysilane and triethoxy-2-thienylsilane, and vinyltriethoxysilane and 3-(triethoxysilyl)furan.

(50) (Triethoxysilyl)cyclohexane and phenyltrimethoxysilane, (triethoxysilyl)cyclohexane and phenyltriethoxysilane, (triethoxysilyl)cyclohexane and vinyltrimethoxysilane, (triethoxysilyl)cyclohexane and vinyltriethoxysilane, (triethoxysilyl)cyclohexane and p-tolyltrimethoxysilane, (triethoxysilyl)cyclohexane and p-methoxyphenyltrimethoxysilane, (triethoxysilyl)cyclohexane and triethoxy-2-thienylsilane, and (triethoxysilyl)cyclohexane and 3-(triethoxysilyl)furan.

(51) p-tolyltrimethoxysilane and phenyltrimethoxysilane, p-tolyltrimethoxysilane and phenyltriethoxysilane, p-tolyltrimethoxysilane and vinyltrimethoxysilane, p-tolyltrimethoxysilane and vinyltriethoxysilane, p-tolyltrimethoxysilane and (triethoxysilyl)cyclohexane, p-tolyltrimethoxysilane and p-methoxyphenyltrimethoxysilane, p-tolyltrimethoxysilane and triethoxy-2-thienylsilane, and p-tolyltrimethoxysilane and 3-(triethoxysilyl)furan.

(52) p-methoxyphenyltrimethoxysilane and phenyltrimethoxysilane, p-methoxyphenyltrimethoxysilane and phenyltriethoxysilane, p-methoxyphenyltrimethoxysilane and vinyltrimethoxysilane, p-methoxyphenyltrimethoxysilane and vinyltriethoxysilane, p-methoxyphenyltrimethoxysilane and (triethoxysilyl)cyclohexane, p-methoxyphenyltrimethoxysilane and p-tolylmethoxysilane, p-methoxyphenyltrimethoxysilane and triethoxy-2-thienylsilane, and p-methoxyphenyltrimethoxysilane and 3-(triethoxysilyl)furan.

Preferred combinations of at least one trialkoxysilane compound and at least one tetraalkoxysilane compound are listed below.

(1) Methyltrimethoxysilane and tetramethoxysilane, methyltrimethoxysilane and tetraethoxysilane, and methyltrimethoxysilane and tetrapropoxysilane.

(2) Methyltriethoxysilane and tetramethoxysilane, methyltriethoxysilane and tetraethoxysilane, and methyltriethoxysilane and tetrapropoxysilane.

(3) Ethyltrimethoxysilane and tetramethoxysilane, ethyltrimethoxysilane and tetraethoxysilane, and ethyltrimethoxysilane and tetrapropoxysilane.

(4) Ethyltriethoxysilane and tetramethoxysilane, ethyltriethoxysilane and tetraethoxysilane, and ethyltriethoxysilane and tetrapropoxysilane.

(5) Propyltrimethoxysilane and tetramethoxysilane, propyltrimethoxysilane and tetraethoxysilane, and propyltrimethoxysilane and tetrapropoxysilane.

(6) Propyltriethoxysilane and tetramethoxysilane, propyltriethoxysilane and tetraethoxysilane, and propyltriethoxysilane and tetrapropoxysilane.

(7) Butyltrimethoxysilane and tetramethoxysilane, butyltrimethoxysilane and tetraethoxysilane, and butyltrimethoxysilane and tetrapropoxysilane.

(8) Butyltriethoxysilane and tetramethoxysilane, butyltriethoxysilane and tetraethoxysilane, and butyltriethoxysilane and tetrapropoxysilane.

(9) Phenyltrimethoxysilane and tetramethoxysilane, phenyltrimethoxysilane and tetraethoxysilane, and phenyltrimethoxysilane and tetrapropoxysilane.

(10) Phenyltriethoxysilane and tetramethoxysilane, phenyltriethoxysilane and tetraethoxysilane, and phenyltriethoxysilane and tetrapropoxysilane.

(11) p-tolyltrimethoxysilane and tetramethoxysilane, p-tolyltrimethoxysilane and tetraethoxysilane, and p-tolyltrimethoxysilane and tetrapropoxysilane.

(12) p-methoxyphenyltrimethoxysilane and tetramethoxysilane, p-methoxyphenyltrimethoxysilane and tetraethoxysilane, and p-methoxyphenyltrimethoxysilane and tetrapropoxysilane.

(13) Vinyltrimethoxysilane and tetramethoxysilane, vinyltrimethoxysilane and tetraethoxysilane, and vinyltrimethoxysilane and tetrapropoxysilane.

(14) Vinyltriethoxysilane and tetramethoxysilane, vinyltriethoxysilane and tetraethoxysilane, and vinyltriethoxysilane and tetrapropoxysilane.

(15) γ-glycidoxypropyltrimethoxysilane and tetramethoxysilane, γ-glycidoxypropyltrimethoxysilane and tetraethoxysilane, and γ-glycidoxypropyltrimethoxysilane and tetrapropoxysilane.

(16) γ-glycidoxypropyltriethoxysilane and tetramethoxysilane, γ-glycidoxypropyltriethoxysilane and tetraethoxysilane, and γ-glycidoxypropyltriethoxysilane and tetrapropoxysilane.

(17) Triethoxy(4-(trifluoromethyl)phenyl)silane and tetramethoxysilane, triethoxy(4-(trifluoromethyl)phenyl)silane and tetraethoxysilane, and triethoxy(4-(trifluoromethyl)phenyl)silane and tetrapropoxysilane.

(18) (Triethoxysilyl)cyclohexane and tetramethoxysilane, (triethoxysilyl)cyclohexane and tetraethoxysilane, and (triethocysilyl)cyclohexane and tetrapropoxysilane.

(19) 3,3,3-trifluoropropyltrimethoxysilane and tetramethoxysilane, 3,3,3-trifluoropropyltrimethoxysilane and tetraethoxysilane, and 3,3,3-trifluoropropyltrimethoxysilane and tetrapropoxysilane.

(20) Perfluorooctylethyltriethoxysilane and tetramethoxysilane, perfluorooctylethyltriethoxysilane and tetraethoxysilane, and perfluorooctylethyltriethoxysilane and tetrapropoxysilane.

(21) Triethoxyfluorosilane and tetramethoxysilane, triethoxyfluorosilane and tetraethoxysilane, and triethoxyfluorosilane and tetrapropoxysilane

(22) Tridecafluoro-1,1,2,2-tetrahydrooctyltriethoxysilane and tetramethoxysilane, tridecafluoro-1,1,2,2-tetrahydrooctyltriethoxysilane and tetraethoxysilane, and tridecafluoro-1,1,2,2-tetrahydrooctyltriethoxysilane and tetrapropoxysilane.

(23) Pentafluorophenylpropyltrimethoxysilane and tetramethoxysilane, pentafluorophenylpropyltrimethoxysilane and tetraethoxysilane, and pentafluorophenylpropyltrimethoxysilane and tetrapropoxysilane.

(24) 3-(heptafluoroisopropoxy)propyltriethoxysilane and tetramethoxysilane, 3-(heptafluoroisopropoxy)propyltriethoxysilane and tetraethoxysilane, and 3-(heptafluoroisopropoxy)propyltriethoxysilane and tetrapropoxysilane.

(25) Heptadecafluoro-1,1,2,2-tetrahydrodecyltriethoxysilane and tetramethoxysilane, heptadecafluoro-1,1,2,2-tetrahydrodecyltriethoxysilane and tetraethoxysilane, and heptadecafluoro-1,1,2,2-tetrahydrodecyltriethoxysilane and tetrapropoxysilane.

(26) Triethoxy-2-thienylsilane and tetramethoxysilane, triethoxy-2-thienylsilane and tetraethoxysilane, and triethoxy-2-thienylsilane and tetrapropoxysilane.

(27) 3-(triethoxysilyl)furan and tetramethoxysilane, 3-(triethoxysilyl)furan and tetraethoxysilane, 3-(triethoxysilyl)furan and tetrapropoxysilane.

More preferred combinations are listed below.

(28) Methyltrimethoxysilane and tetramethoxysilane, methyltrimethoxysilane and tetraethoxysilane, and methyltrimethoxysilane and tetrapropoxysilane.

(29) Methyltriethoxysilane and tetramethoxysilane, methyltriethoxysilane and tetraethoxysilane, and methyltriethoxysilane and tetrapropoxysilane.

(30) Ethyltrimethoxysilane and tetramethoxysilane, ethyltrimethoxysilane and tetraethoxysilane, and ethyltrimethoxysilane and tetrapropoxysilane.
(31) Ethyltriethoxysilane and tetramethoxysilane, ethyltriethoxysilane and tetraethoxysilane, and ethyltriethoxysilane and tetrapropoxysilane.
(32) Propyltrimethoxysilane and tetramethoxysilane, propyltrimethoxysilane and tetraethoxysilane, and propyltrimethoxysilane and tetrapropoxysilane.
(33) Propyltriethoxysilane and tetramethoxysilane, propyltriethoxysilane and tetraethoxysilane, and propyltriethoxysilane and tetrapropoxysilane.
(34) Butyltrimethoxysilane and tetramethoxysilane, butyltrimethoxysilane and tetraethoxysilane, and butyltrimethoxysilane and tetrapropoxysilane.
(35) Butyltriethoxysilane and tetramethoxysilane, butyltriethoxysilane and tetraethoxysilane, and butyltriethoxysilane and tetrapropoxysilane.
(36) Phenyltrimethoxysilane and tetramethoxysilane, phenyltrimethoxysilane and tetraethoxysilane, and phenyltrimethoxysilane and tetrapropoxysilane.
(37) Phenyltriethoxysilane and tetramethoxysilane, phenyltriethoxysilane and tetraethoxysilane, and phenyltriethoxysilane and tetrapropoxysilane.
(38) p-tolyltrimethoxysilane and tetramethoxysilane, p-tolyltrimethoxysilane and tetraethoxysilane, and p-tolyltrimethoxysilane and tetrapropoxysilane.
(39) p-methoxyphenyltrimethoxysilane and tetramethoxysilane, p-methoxyphenyltrimethoxysilane and tetraethoxysilane, and p-methoxyphenyltrimethoxysilane and tetrapropoxysilane.
(40) Vinyltrimethoxysilane and tetramethoxysilane, vinyltrimethoxysilane and tetraethoxysilane, and vinyltrimethoxysilane and tetrapropoxysilane.
(41) Vinyltriethoxysilane and tetramethoxysilane, vinyltriethoxysilane and tetraethoxysilane, and vinyltriethoxysilane and tetrapropoxysilane.
(42) Triethoxy(4-(trifluoromethyl)phenyl)silane and tetramethoxysilane, triethoxy(4-(trifluoromethyl)phenyl)silane and tetraethoxysilane, and triethoxy(4-(trifluoromethyl)phenyl)silane and tetrapropoxysilane.
(43) (Triethoxysilyl)cyclohexane and tetramethoxysilane, (triethoxysilyl)cyclohexane and tetraethoxysilane, and (triethocysilyl)cyclohexane and tetrapropoxysilane.
(44) 3,3,3-trifluoropropyltrimethoxysilane and tetramethoxysilane, 3,3,3-trifluoropropyltrimethoxysilane and tetraethoxysilane, and 3,3,3-trifluoropropyltrimethoxysilane and tetrapropoxysilane.
(45) Perfluorooctylethyltriethoxysilane and tetramethoxysilane, perfluorooctylethyltriethoxysilane and tetraethoxysilane, and perfluorooctylethylriethoxysilane and tetrapropoxysilane.
(46) Triethoxyfluorosilane and tetramethoxysilane, triethoxyfluorosilane and tetraethoxysilane, and triethoxyfluorosilane and tetrapropoxysilane.
(47) Tridecafluoro-1,1,2,2-tetrahydrooctyltriethoxysilane and tetramethoxysilane, tridecafluoro-1,1,2,2-tetrahydrooctyltriethoxysilane and tetraethoxysilane, and tridecafluoro-1,1,2,2-tetrahydrooctyltriethoxysilane and tetrapropoxysilane.
(48) Pentafluorophenylpropyltrimethoxysilane and tetramethoxysilane, pentafluorophenylpropyltrimethoxysilane and tetraethoxysilane, and pentafluorophenylpropyltrimethoxysilane and tetrapropoxysilane.
(49) 3-(heptafluoroisopropoxy)propyltriethoxysilane and tetramethoxysilane, 3-(heptafluoroisopropoxy)propyltriethoxysilane and tetraethoxysilane, and 3-(heptafluoroisopropoxy)propyltriethoxysilane and tetrapropoxysilane.
(50) Heptadecafluoro-1,1,2,2-tetrahydrodecyltriethoxysilane and tetramethoxysilane, heptadecafluoro-1,1,2,2-tetrahydrodecyltriethoxysilane and tetraethoxysilane, and heptadecafluoro-1,1,2,2-tetrahydrodecyltriethoxysilane and tetrapropoxysilane.
(51) Triethoxy-2-thienylsilane and tetramethoxysilane, triethoxy-2-thienylsilane and tetraethoxysilane, and triethoxy-2-thienylsilane and tetrapropoxysilane.
(52) 3-(triethoxysilyl)furan and tetramethoxysilane, 3-(triethoxysilyl)furan and tetraethoxysilane, 3-(triethoxysilyl)furan and tetrapropoxysilane.

Preferred combinations of two species of dialkoxysilane compounds are listed below.

(1) Methylhydrogendimethoxysilane and methylhydrogendiethoxysilane, methylhydrogendimethoxysilane and dimethyldimethoxysilane, methylhydrogendimethoxysilane and dimethyldiethoxysilane, methylhydrogendimethoxysilane and methylethyldimethoxysilane, methylhydrogendimethoxysilane and diethyldimethoxysilane, methylhydrogendimethoxysilane and diethyldiethoxysilane, methylhydrogendimethoxysilane and methylpropyldimethoxysilane, methylhydrogendimethoxysilane and methylpropyldiethoxysilane, methylhydrogendimethoxysilane and diisopropyldimethoxysilane, methylhydrogendimethoxysilane and phenylmethyldimethoxysilane, methylhydrogendimethoxysilane and vinylmethyldimethoxysilane, methylhydrogendimethoxysilane and γ-glycidoxypropylmethyldimethoxysilane, methylhydrogendimethoxysilane and γ-glycidoxypropylmethyldiethoxysilane, methylhydrogendimethoxysilane and β-(3,4-epoxycyclohexyl)ethylmethyldimethoxysilane, methylhydrogendimethoxysilane and γ-methacryloxypropylmethyldimethoxysilane, methylhydrogendimethoxysilane and γ-methacryloxypropylmethyldiethoxysilane, methylhydrogendimethoxysilane and γ-mercaptopropyldimethoxysilane, methylhydrogendimethoxysilane and γ-aminopropylmethyldiethoxysilane, methylhydrogendimethoxysilane and N-(2-aminoethyl)aminopropylmethyldimethoxysilane, and methylhydrogendimethoxysilane and 3,3,3-trifluoropropylmethyldimethoxysilane.

(2) Methylhydrogendiethoxysilane and dimethyldimethoxysilane, methylhydrogendiethoxysilane and dimethyldiethoxysilane, methylhydrogendiethoxysilane and methylethyldimethoxysilane, methylhydrogendiethoxysilane and diethyldimethoxysilane, methylhydrogendiethoxysilane and diethyldiethoxysilane, methylhydrogendiethoxysilane and methylpropyldimethoxysilane, methylhydrogendiethoxysilane and methylpropyldiethoxysilane, methylhydrogendiethoxysilane and diisopropyldimethoxysilane, methylhydrogendiethoxysilane and phenylmethyldimethoxysilane, methylhydrogendiethoxysilane and vinylmethyldimethoxysilane, methylhydrogendiethoxysilane and γ-glycidoxypropylmethyldimethoxysilane, methylhydrogendiethoxysilane and γ-glycidoxypropylmethyldiethoxysilane, methylhydrogendiethoxysilane and β-(3,4-epoxycyclohexyl)ethylmethyldimethoxysilane, methylhydrogendiethoxysilane and γ-methacryloxypropylmethyldimethoxysilane, methylhydrogendiethoxysilane and γ-methacryloxypropylmethyldiethoxysilane, methylhydrogendiethoxysilane and γ-mercaptopropylmethyldimethoxysilane, methylhydrogendiethoxysilane and γ-aminopropylmethyldiethoxysilane, methylhydrogendiethoxysilane and N-(2-aminoethyl)aminopropylmethyldimethoxysilane, and methylhydrogendiethoxysilane and 3,3,3-trifluoropropylmethyldimethoxysilane.

(3) Dimethyldimethoxysilane and dimethyldiethoxysilane, dimethyldimethoxysilane and methylethyldimethoxysilane, dimethyldimethoxysilane and diethyldimethoxysilane, dimethyldimethoxysilane and diethyldiethoxysilane, dimethyldimethoxysilane and methylpropyldimethoxysilane, dimethyldimethoxysilane and methylpropyldiethoxysilane, dimethyldimethoxysilane and diisopropyldimethoxysilane, dimethyldimethoxysilane and phenylmethyldimethoxysilane, dimethyldimethoxysilane and vinylmethyldimethoxysilane, dimethyldimethoxysilane and γ-glycidoxypropylmethyldimethoxysilane, dimethyldimethoxysilane and γ-glycidoxypropylmethyldiethoxysilane, dimethyldimethoxysilane and β-(3,4-epoxycyclohexyl)ethylmethyldimethoxysilane, dimethyldimethoxysilane and γ-methacryloxypropylmethyldimethoxysilane, dimethyldimethoxysilane and γ-methacryloxypropylmethyldiethoxysilane, dimethyldimethoxysilane and γ-mercaptopropylmethyldimethoxysilane, dimethyldimethoxysilane and γ-aminopropylmethyldiethoxysilane, dimethyldimethoxysilane and N-(2-aminoethyl)aminopropylmethyldimethoxysilane, and dimethyldimethoxysilane and 3,3,3-trifluoropropylmethyldimethoxysilane.

(4) Dimethyldiethoxysilane and methylethyldimethoxysilane, dimethyldiethoxysilane and diethyldimethoxysilane, dimethyldiethoxysilane and diethyldiethoxysilane, dimethyldiethoxysilane and methylpropyldimethoxysilane, dimethyldiethoxysilane and methylpropyldiethoxysilane, dimethyldiethoxysilane and diisopropyldimethoxysilane, dimethyldiethoxysilane and phenylmethyldimethoxysilane, dimethyldiethoxysilane and vinylmethyldimethoxysilane, dimethyldiethoxysilane and γ-glycidoxypropylmethyldimethoxysilane, dimethyldiethoxysilane and γ-glycidoxypropylmethydiethoxysilane, dimethyldiethoxysilane and β-(3,4-epoxycyclohexyl)ethylmethyldimethoxysilane, dimethyldiethoxysilane and γ-methacryloxypropylmethyldimethoxysilane, dimethyldiethoxysilane and γ-methacryloxypropylmethyldiethoxysilane, dimethyldiethoxysilane and γ-mercaptopropyldimethoxysilane, dimethyldiethoxysilane and γ-aminopropylmethyldiethoxysilane, dimethyldiethoxysilane and N-(2-aminoethyl)aminopropylmethyldimethoxysilane, and dimethyldiethoxysilane and 3,3,3-trifluoropropylmethyldimethoxysilane.

(5) Methylethyldimethoxysilane and diethyldimethoxysilane, methylethyldimethoxysilane and diethyldiethoxysilane, methylethyldimethoxysilane and methylpropyldimethoxysilane, methylethyldimethoxysilane and methylpropyldiethoxysilane, methylethyldimethoxysilane and diisopropyldimethoxysilane, methylethyldimethoxysilane and phenylmethyldimethoxysilane, methylethyldimethoxysilane and vinylmethyldimethoxysilane, methylethyldimethoxysilane and γ-glycidoxypropylmethyldimethoxysilane, methylethyldimethoxysilane and γ-glycidoxypropylmethyldiethoxysilane, methylethyldimethoxysilane and β-(3,4-epoxycyclohexyl)ethylmethyldimethoxysilane, methylethyldimethoxysilane and γ-methacryloxypropylmethyldimethoxysilane, methylethyldimethoxysilane and γ-methacryloxypropylmethyldiethoxysilane, methylethyldimethoxysilane and γ-mercaptopropylmethyldimethoxysilane, methylethyldimethoxysilane and γ-aminopropylmethyldiethoxysilane, methylethyldimethoxysilane and N-(2-aminoethyl)aminopropylmethyldimethoxysilane, and methylethyldimethoxysilane and 3,3,3-trifluoropropylmethyldimethoxysilane.

(6) Diethyldimethoxysilane and diethyldiethoxysilane, diethyldimethoxysilane and methylpropyldimethoxysilane, diethyldimethoxysilane and methylpropyldiethoxysilane, diethyldimethoxysilane and diisopropyldimethoxysilane, diethyldimethoxysilane and phenylmethyldimethoxysilane, diethyldimethoxysilane and vinylmethyldimethoxysilane, diethyldimethoxysilane and γ-glycidoxypropylmethyldimethoxysilane, diethyldimethoxysilane and γ-glycidoxypropylmethyldiethoxysilane, diethyldimethoxysilane and β-(3,4-epoxycyclohexyl)ethylmethyldimethoxysilane, diethyldimethoxysilane and γ-methacryloxypropylmethyldimethoxysilane, diethyldimethoxysilane and γ-methacryloxypropylmethyldiethoxysilane, diethyldimethoxysilane and γ-mercaptopropylmethyldimethoxysilane, diethyldimethoxysilane and γ-aminopropylmethyldiethoxysilane, diethyldimethoxysilane and N-(2-aminoethyl)aminopropylmethyldimethoxysilane, and diethyldimethoxysilane and 3,3,3-trifluoropropylmethyldimethoxysilane.

(7) Diethyldiethoxysilane and methylpropyldimethoxysilane, diethyldiethoxysilane and methylpropyldiethoxysilane, diethyldiethoxysilane and diisopropyldimethoxysilane, diethyldiethoxysilane and phenylmethyldimethoxysilane, diethyldiethoxysilane and vinylmethyldimethoxysilane, diethyldiethoxysilane and γ-glycidoxypropylmethyldimethoxysilane, diethyldiethoxysilane and γ-glycidoxypropylmethyldiethoxysilane, diethyldiethoxysilane and β-(3,4-epoxycyclohexyl)ethylmethyldimethoxysilane, diethyldiethoxysilane and γ-methacryloxypropylmethyldimethoxysilane, diethyldiethoxysilane and γ-methacryloxypropylmethyldiethoxysilane, diethyldiethoxysilane and γ-mercaptopropylmethyldimethoxysilane, diethyldiethoxysilane and γ-aminopropylmethyldiethoxysilane, diethyldiethoxysilane and N-(2-aminoethyl)aminopropylmethyldimethoxysilane, and diethyldiethoxysilane and 3,3,3-trifluoropropylmethyldimethoxysilane.

(8) Methylpropyldimethoxysilane and methylpropyldiethoxysilane, methylpropyldimethoxysilane and diisopropyldimethoxysilane, methylpropyldimethoxysilane and phenylmethyldimethoxysilane, methylpropyldimethoxysilane and vinylmethyldimethoxysilane, methylpropyldimethoxysilane and γ-glycidoxypropylmethyldimethoxysilane, methylpropyldimethoxysilane and γ-glycidoxypropylmethyldiethoxysilane, methylpropyldimethoxysilane and β-(3,4-epoxycyclohexyl)ethylmethyldimethoxysilane, methylpropyldimethoxysilane and γ-methacryloxypropylmethyldimethoxysilane, methylpropyldimethoxysilane and γ-methacryloxypropylmethyldiethoxysilane, methylpropyldimethoxysilane and γ-mercaptopropylmethyldimethoxysilane, methylpropyldimethoxysilane and γ-aminopropylmethyldiethoxysilane, methylpropyldimethoxysilane and N-(2-aminoethyl)aminopropylmethyldimethoxysilane, and methylpropyldimethoxysilane and 3,3,3-trifluoropropylmethyldimethoxysilane.

(9) Methylpropyldiethoxysilane and diisopropyldimethoxysilane, methylpropyldiethoxysilane and phenylmethyldimethoxysilane, methylpropyldiethoxysilane and vinylmethyldimethoxysilane, methylpropyldiethoxysilane and γ-glycidoxypropylmethyldimethoxysilane, methylpropyldiethoxysilane and γ-glycidoxypropylmethyldiethoxysilane, methylpropyldiethoxysilane and β-(3,4-epoxycyclohexyl)ethylmethyldimethoxysilane, methylpropyldiethoxysilane and γ-methacryloxypropylmethyldimethoxysilane, methylpropyldiethoxysilane and γ-methacryloxypropylmethyldiethoxysilane, methylpropyldiethoxysilane and γ-mercaptopropylmethyldimethoxysilane, methylpropyldiethoxysilane and γ-aminopropylmethyldiethoxysilane, methylpropyldiethoxysilane and N-(2-aminoethyl)aminopropylmethyldimethoxysilane, and methylpropyldiethoxysilane and 3,3,3-trifluoropropylmethyldimethoxysilane.

(10) Diisopropyldimethoxysilane and phenylmethyldimethoxysilane, diisopropyldimethoxysilane and vinylmethyldimethoxysilane, diisopropyldimethoxysilane and γ-glycidoxypropylmethyldimethoxysilane, diisopropyldimethoxysilane and γ-glycidoxypropylmethyldiethoxysilane, diisopropyldimethoxysilane and β-(3,4-epoxycyclohexyl)ethylmethyldimethoxysilane, diisopropyldimethoxysilane and γ-methacryloxypropylmethyldimethoxysilane, diisopropyldimethoxysilane and γ-methacryloxypropylmethyldiethoxysilane, diisopropyldimethoxysilane and γ-mercaptopropylmethyldimethoxysilane, diisopropyldimethoxysilane and γ-aminopropylmethyldiethoxysilane, diisopropyldimethoxysilane and N-(2-aminoethyl)aminopropylmethyldimethoxysilane, and diisopropyldimethoxysilane and 3,3,3-trifluoropropylmethyldimethoxysilane.

(11) Phenylmethyldimethoxysilane and vinylmethyldimethoxysilane, phenylmethyldimethoxysilane and γ-glycidoxypropylmethyldimethoxysilane, phenylmethyldimethoxysilane and γ-glycidoxypropylmethyldiethoxysilane, phenylmethyldimethoxysilane and β-(3,4-epoxycyclohexyl)ethylmethyldimethoxysilane, phenylmethyldimethoxysilane and γ-methacryloxypropylmethyldimethoxysilane, phenylmethyldimethoxysilane and γ-methacryloxypropylmethyldiethoxysilane, phenylmethyldimethoxysilane and γ-mercaptopropylmethyldimethoxysilane, phenylmethyldimethoxysilane and γ-aminopropylmethyldiethoxysilane, phenylmethyldimethoxysilane and N-(2-aminoethyl)aminopropylmethyldimethoxysilane, and phenylmethyldimethoxysilane and 3,3,3-trifluoropropylmethyldimethoxysilane.

(12) Vinylmethyldimethoxysilane and γ-glycidoxypropylmethyldimethoxysilane, vinylmethyldimethoxysilane and γ-glycidoxypropylmethyldiethoxysilane, vinylmethyldimethoxysilane and β-(3,4-epoxycyclohexyl)ethylmethyldimethoxysilane, vinylmethyldimethoxysilane and γ-methacryloxypropylmethyldimethoxysilane, vinylmethyldimethoxysilane and γ-methacryloxypropylmethyldiethoxysilane, vinylmethyldimethoxysilane and γ-mercaptopropylmethyldimethoxysilane, vinylmethyldimethoxysilane and γ-aminopropylmethyldiethoxysilane, vinylmethyldimethoxysilane and N-(2-aminoethyl)aminopropylmethyldimethoxysilane, and vinylmethyldimethoxysilane and 3,3,3-trifluoropropylmethyldimethoxysilane.

(13) γ-glycidoxypropylmethyldimethoxysilane and γ-glycidoxypropylmethyldiethoxysilane, γ-glycidoxypropylmethyldiethoxysilane and β-(3,4-epoxycyclohexyl)ethylmethyldimethoxysilane, γ-glycidoxypropylmethyldimethoxysilane and γ-methacryloxypropylmethyldimethoxysilane, γ-glycidoxypropylmethyldimethoxysilane and γ-methacryloxypropylmethyldiethoxysilane, γ-glycidoxypropylmethyldimethoxysilane and γ-mercaptopropylmethyldimethoxysilane, γ-glycidoxypropylmethyldimethoxysilane and γ-aminopropylmethyldiethoxysilane, γ-glycidoxypropylmethyldimethoxysilane and N-(2-aminoethyl)aminopropylmethyldimethoxysilane, and γ-glycidoxypropylmethyldimethoxysilane and 3,3,3-trifluoropropylmethyldimethoxysilane.

(14) γ-glycidoxypropylmethyldiethoxysilane and β-(3,4-epoxycyclohexyl)ethylmethyldimethoxysilane, γ-glycidoxypropylmethyldiethoxysilane and γ-methacryloxypropylmethyldimethoxysilane, γ-glycidoxypropylmethyldiethoxysilane and γ-methacryloxypropylmethyldiethoxysilane, γ-glycidoxypropylmethyldiethoxysilane and γ-mercaptopropylmethyldimethoxysilane, γ-glycidoxypropylmethyldiethoxysilane and γ-aminopropylmethyldiethoxysilane, γ-glycidoxypropylmethyldiethoxysilane and N-(2-aminoethyl)aminopropylmethyldimethoxysilane, and γ-glycidoxypropylmethyldiethoxysilane and 3,3,3-trifluoropropylmethyldimethoxysilane.

(15) β-(3,4-epoxycyclohexyl)ethylmethyldimethoxysilane and γ-methacryloxypropylmethyldimethoxysilane, β-(3,4-epoxycyclohexyl)ethylmethyldimethoxysilane and γ-methacryloxypropylmethyldiethoxysilane, β-(3,4-epoxycyclohexyl)ethylmethyldimethoxysilane and γ-mercaptopropylmethyldimethoxysilane, β-(3,4-epoxycyclohexyl)ethylmethyldimethoxysilane and γ-aminopropylmethyldiethoxysilane, β-(3,4-epoxycyclohexyl)ethylmethyldimethoxysilane and N-(2-aminoethyl)aminopropylmethyldimethoxysilane, and β-(3,4-epoxycyclohexyl)ethylmethyldimethoxysilane and 3,3,3-trifluoropropylmethyldimethoxysilane.

(16) γ-methacryloxypropylmethyldimethoxysilane and γ-methacryloxypropylmethyldiethoxysilane, γ-methacryloxypropylmethyldimethoxysilane and γ-mercaptopropylmethyldimethoxysilane, γ-methacryloxypropylmethyldimethoxysilane and γ-aminopropylmethyldiethoxysilane, γ-methacryloxypropylmethyldimethoxysilane and N-(2-aminoethyl)aminopropylmethyldimethoxysilane, and γ-methacryloxypropylmethyldimethoxysilane and 3,3,3-trifluoropropylmethyldimethoxysilane.

(17) γ-methacryloxypropylmethyldiethoxysilane and γ-mercaptopropylmethyldimethoxysilane, γ-methacryloxypropylmethyldiethoxysilane and γ-aminopropylmethyldiethoxysilane, γ-methacryloxypropylmethyldiethoxysilane and N-(2-aminoethyl)aminopropylmethyldimethoxysilane, and γ-methacryloxypropylmethyldiethoxysilane and 3,3,3-trifluoropropylmethyldimethoxysilane.

(18) γ-mercaptopropylmethyldimethoxysilane and γ-aminopropylmethyldiethoxysilane, γ-mercaptopropylmethyldimethoxysilane and N-(2-aminoethyl)aminopropylmethyldimethoxysilane, and γ-mercaptopropyldimethoxysilane and 3,3,3-trifluoropropylmethyldimethoxysilane.

(19) γ-aminopropylmethyldiethoxysilane and N-(2-aminoethyl)aminopropylmethyldimethoxysilane, and γ-aminopropylmethyldiethoxysilane and 3,3,3-trifluoropropylmethyldimethoxysilane.

(20) N-(2-aminoethyl)aminopropylmethyldimethoxysilane and 3,3,3-trifluoropropylmethyldimethoxysilane.

Preferred combinations of at least one dialkoxysilane compound and at least one trialkoxysilane compound are listed below.

(1) Methylhydrogendimethoxysilane and methyltrimethoxysilane, methylhydrogendimethoxysilane and methyltriethoxysilane, methylhydrogendimethoxysilane and ethyltrimethoxysilane, methylhydrogendimethoxysilane and ethyltriethoxysilane, methylhydrogendimethoxysilane and propyltrimethoxysilane, methylhydrogendimethoxysilane and propyltriethoxysilane, methylhydrogendimethoxysilane and butyltrimethoxysilane, methylhydrogendimethoxysilane and butyltriethoxysilane, methylhydrogendimethoxysilane and pentyltrimethoxysilane, methylhydrogendimethoxysilane and pentyltriethoxysilane, methylhydrogendimethoxysilane and heptyltrimethoxysilane, methylhydrogendimethoxysilane and heptyltriethoxysilane, methylhydrogendimethoxysilane and octyltrimethoxysilane, methylhydrogendimethoxysilane and octyltriethoxysilane, methylhydrogendimethoxysilane and dodecyltrimethoxysilane, methylhydrogendimethoxysilane and dodecyltriethoxysilane, methylhydrogendimethoxysilane and hexadecyltrimethoxysilane, methylhydrogendimethoxysilane and hexadecyltriethoxysilane, methylhydrogendimethoxysilane and octadecyltrimethoxysilane, methylhydrogendimethoxysilane and octadecyltriethoxysilane, methylhydrogendimethoxysilane and phenyltrimethoxysilane, methylhydrogendimethoxysilane and phenyltriethoxysilane, methylhydrogendimethoxysilane and vinyltrimethoxysilane, methylhydrogendimethoxysilane and vinyltriethoxysilane, methylhydrogendimethoxysilane and γ-aminopropyltrimethoxysilane, methylhydrogendimethoxysilane and γ-aminopropyltriethoxysilane, methylhydrogendimethoxysilane and γ-glycidoxypropyltrimethoxysilane, methylhydrogendimethoxysilane and γ-glycidoxypropyltriethoxysilane, methylhydrogendimethoxysilane and γ-methacryloxypropyltrimethoxysilane, methylhydrogendimethoxysilane and γ-methacryloxypropyltriethoxysilane, methylhydrogendimethoxysilane and triethoxy(4-(trifluoromethyl)phenyl)silane, methylhydrogendimethoxysilane and dodecyltriethoxysilane, methylhydrogendimethoxysilane and 3,3,3-trifluoropropyltrimethoxysilane, methylhydrogendimethoxysilane and (triethoxysilyl)cyclohexane, methylhydrogendimethoxysilane and perfluorooctylethyltriethoxysilane, methylhydrogendimethoxysilane and triethoxyfluorosilane, methylhydrogendimethoxysilane and tridecafluoro-1,1,2,2-tetrahydrooctyltriethoxysilane, methylhydrogendimethoxysilane and pentafluorophenylpropyltrimethoxysilane, methylhydrogendimethoxysilane and 3-(heptafluoroisopropoxy)propyltriethoxysilane, methylhydrogendimethoxysilane and heptadecafluoro-1,1,2,2-tetrahydrodecyltriethoxysilane, methylhydrogendimethoxysilane and triethoxy-2-thienylsilane, and methylhydrogendimethoxysilane and 3-(triethoxysilyl)furan.

(2) Methylhydrogendiethoxysilane and methyltrimethoxysilane, methylhydrogendiethoxysilane and methyltriethoxysilane, methylhydrogendiethoxysilane and ethyltrimethoxysilane, methylhydrogendiethoxysilane and ethyltriethoxysilane, methylhydrogendiethoxysilane and propyltrimethoxysilane, methylhydrogendiethoxysilane and propyltriethoxysilane, methylhydrogendiethoxysilane and butyltrimethoxysilane, methylhydrogendiethoxysilane and butyltriethoxysilane, methylhydrogendiethoxysilane and pentyltrimethoxysilane, methylhydrogendiethoxysilane and pentyltriethoxysilane, methylhydrogendiethoxysilane and heptyltrimethoxysilane, methylhydrogendiethoxysilane and heptyltriethoxysilane, methylhydrogendiethoxysilane and octyltrimethoxysilane, methylhydrogendiethoxysilane and octyltriethoxysilane, methylhydrogendiethoxysilane and dodecyltrimethoxysilane, methylhydrogendiethoxysilane and dodecyltriethoxysilane, methylhydrogendiethoxysilane and hexadecyltrimethoxysilane, methylhydrogendiethoxysilane and hexadecyltriethoxysilane, methylhydrogendiethoxysilane and octadecyltrimethoxysilane, methylhydrogendiethoxysilane and octadecyltriethoxysilane, methylhydrogendiethoxysilane and phenyltrimethoxysilane, methylhydrogendiethoxysilane and phenyltriethoxysilane, methylhydrogendiethoxysilane and vinyltrimethoxysilane, methylhydrogendiethoxysilane and vinyltriethoxysilane, methylhydrogendiethoxysilane and γ-aminopropyltrimethoxysilane, methylhydrogendiethoxysilane and γ-aminopropyltriethoxysilane, methylhydrogendiethoxysilane and γ-glycidoxypropyltrimethoxysilane, methylhydrogendiethoxysilane and γ-glycidoxypropyltriethoxysilane, methylhydrogendiethoxysilane and γ-methacryloxypropyltrimethoxysilane, methylhydrogendiethoxysilane and γ-methacryloxypropyltriethoxysilane, methylhydrogendiethoxysilane and triethoxy(4-(trifluoromethyl)phenyl)silane, methylhydrogendiethoxysilane and dodecyltriethoxysilane, methylhydrogendiethoxysilane and 3,3,3-trifluoropropyltrimethoxysilane, methylhydrogendiethoxysilane and (triethoxysilyl)cyclohexane, methylhydrogendiethoxysilane and perfluorooctylethyltriethoxysilane, methylhydrogendiethoxysilane and triethoxyfluorosilane, methylhydrogendiethoxysilane and tridecafluoro-1,1,2,2-tetrahydrooctyltriethoxysilane, methylhydrogendiethoxysilane and pentafluorophenylpropyltrimethoxysilane, methylhydrogendiethoxysilane and 3-(heptafluoroisopropoxy)propyltriethoxysilane, methylhydrogendiethoxysilane and heptadecafluoro-1,1,2,2-tetrahydrodecyltriethoxysilane, methylhydrogendiethoxysilane and triethoxy-2-thienylsilane, and 3-(triethoxysilyl)furan.

(3) Dimethyldimethoxysilane and methyltrimethoxysilane, dimethyldimethoxysilane and methyltriethoxysilane, dimethyldimethoxysilane and ethyltrimethoxysilane, dimethyldimethoxysilane and ethyltriethoxysilane, dimethyldimethoxysilane and propyltrimethoxysilane, dimethyldimethoxysilane and propyltriethoxysilane, dimethyldimethoxysilane and butyltrimethoxysilane, dimethyldimethoxysilane and butyltriethoxysilane, dimethyldimethoxysilane and pentyltrimethoxysilane, dimethyldimethoxysilane and pentyltriethoxysilane, dimethyldimethoxysilane and heptyltrimethoxysilane, dimethyldimethoxysilane and heptyltriethoxysilane, dimethyldimethoxysilane and octyltrimethoxysilane, dimethyldimethoxysilane and octyltriethoxysilane, dimethyldimethoxysilane and dodecyltrimethoxysilane, dimethyldimethoxysilane and dodecyltriethoxysilane, dimethyldimethoxysilane and hexadecyltrimethoxysilane, dimethyldimethoxysilane and hexadecyltriethoxysilane, dimethyldimethoxysilane and octadecyltrimethoxysilane, dimethyldimethoxysilane and octadecyltriethoxysilane, dimethyldimethoxysilane and phenyltrimethoxysilane, dimethyldimethoxysilane and phenyltriethoxysilane, dimethyldimethoxysilane and vinyltrimethoxysilane, dimethyldimethoxysilane and vinyltriethoxysilane, dimethyldimethoxysilane and γ-aminopropyltrimethoxysilane, dimethyldimethoxysilane and γ-aminopropyltriethoxysilane, dimethyldimethoxysilane and γ-glycidoxypropyltrimethoxysilane, dimethyldimethoxysilane and γ-glycidoxypropyltriethoxysilane, dimethyldimethoxysilane and γ-methacryloxypropyltrimethoxysilane, dimethyldimethoxysilane and γ-methacryloxypropyltriethoxysilane, dimethyldimethoxysilane and triethoxy(4-(trifluoromethyl)phenyl)silane, dimethyldimethoxysilane and dodecyltriethoxysilane, dimethyldimethoxysilane and 3,3,3-trifluoropropyltrimethoxysilane, dimethyldimethoxysilane and (triethoxysilyl)cyclohexane, dimethyldimethoxysilane and perfluorooctylethyltriethoxysilane, dimethyldimethoxysilane and triethoxyfluorosilane, dimethyldimethoxysilane and tridecafluoro-1,1,2,2-tetrahydrooctyltriethoxysilane, dimethyldimethoxysilane and pentafluorophenylpropyltrimethoxysilane, dimethyldimethoxysilane and 3-(heptafluoroisopropoxy)propyltriethoxysilane, dimethyldimethoxysilane and heptadecafluoro-1,1,2,2-tetrahydrodecyltriethoxysilane, dimethyldimethoxysilane and triethoxy-2-thienylsilane, and dimethyldimethoxysilane and 3-(triethoxysilyl)furan.

(4) Dimethyldiethoxysilane and methyltrimethoxysilane, dimethyldiethoxysilane and methyltriethoxysilane, dimethyldiethoxysilane and ethyltrimethoxysilane, dimethyldiethoxysilane and ethyltriethoxysilane, dimethyldiethoxysilane and propyltrimethoxysilane, dimethyldiethoxysilane and propyltriethoxysilane, dimethyldiethoxysilane and butyltrimethoxysilane, dimethyldiethoxysilane and butyltriethoxysilane, dimethyldiethoxysilane and pentyltrimethoxysilane, dimethyldiethoxysilane and pentyltriethoxysilane, dimethyldiethoxysilane and heptyltrimethoxysilane, dimethyldiethoxysilane and heptyltriethoxysilane, dimethyldiethoxysilane and octyltrimethoxysilane, dimethyldiethoxysilane and octyltriethoxysilane, dimethyldiethoxysilane and dodecyltrimethoxysilane, dimethyldiethoxysilane and dodecyltriethoxysilane, dimethyldiethoxysilane and hexadecyltrimethoxysilane, dimethyldiethoxysilane and hexadecyltriethoxysilane, dimethyldiethoxysilane and octadecyltrimethoxysilane, dimethyldiethoxysilane and octadecyltriethoxysilane, dimethyldiethoxysilane and phenyltrimethoxysilane, dimethyldiethoxysilane and phenyltriethoxysilane, dimethyldiethoxysilane and vinyltrimethoxysilane, dimethyldiethoxysilane and vinyltriethoxysilane, dimethyldiethoxysilane and γ-aminopropyltrimethoxysilane, dimethyldiethoxysilane and γ-aminopropyltriethoxysilane, dimethyldiethoxysilane and γ-glycidoxypropyltrimethoxysilane, dimethyldiethoxysilane and γ-glycidoxypropyltriethoxysilane, dimethyldiethoxysilane and γ-methacryloxypropyltrimethoxysilane, dimethyldiethoxysilane and γ-methacryloxypropyltriethoxysilane, dimethyldiethoxysilane and triethoxy(4-(trifluoromethyl)phenyl)silane, dimethyldiethoxysilane and dodecyltriethoxysilane, dimethyldiethoxysilane and 3,3,3-trifluoropropyltrimethoxysilane, dimethyldiethoxysilane and (triethoxysilyl)cyclohexane, dimethyldiethoxysilane and perfluorooctylethyltriethoxysilane, dimethyldiethoxysilane and triethoxyfluorosilane, dimethyldiethoxysilane and tridecafluoro-1,1,2,2-tetrahydrooctyltriethoxysilane, dimethyldiethoxysilane and pentafluorophenylpropyltrimethoxysilane, dimethyldiethoxysilane and 3-(heptafluoroisopropoxy)propyltriethoxysilane, dimethyldiethoxysilane and heptadecafluoro-1,1,2,2-tetrahydrodecyltriethoxysilane, dimethyldiethoxysilane and triethoxy-2-thienylsilane, and 3-(triethoxysilyl)furan.

(5) Methylethyldimethoxysilane and methyltrimethoxysilane, methylethyldimethoxysilane and methyltriethoxysilane, methylethyldimethoxysilane and ethyltrimethoxysilane, methylethyldimethoxysilane and ethyltriethoxysilane, methylethyldimethoxysilane and propyltrimethoxysilane, methylethyldimethoxysilane and propyltriethoxysilane, methylethyldimethoxysilane and butyltrimethoxysilane, methylethyldimethoxysilane and butyltriethoxysilane, methylethyldimethoxysilane and pentyltrimethoxysilane, methylethyldimethoxysilane and pentyltriethoxysilane, methylethyldimethoxysilane and heptyltrimethoxysilane, methylethyldimethoxysilane and heptyltriethoxysilane, methylethyldimethoxysilane and octyltrimethoxysilane, methylethyldimethoxysilane and octyltriethoxysilane, methylethyldimethoxysilane and dodecyltrimethoxysilane, methylethyldimethoxysilane and dodecyltriethoxysilane, methylethyldimethoxysilane and hexadecyltrimethoxysilane, methylethyldimethoxysilane and hexadecyltriethoxysilane, methylethyldimethoxysilane and octadecyltrimethoxysilane, methylethyldimethoxysilane and octadecyltriethoxysilane, methylethyldimethoxysilane and phenyltrimethoxysilane, methylethyldimethoxysilane and phenyltriethoxysilane, methylethyldimethoxysilane and vinyltrimethoxysilane, methylethyldimethoxysilane and vinyltriethoxysilane, methylethyldimethoxysilane and γ-aminopropyltrimethoxysilane, methylethyldimethoxysilane and γ-aminopropyltriethoxysilane, methylethyldimethoxysilane and γ-glycidoxypropyltrimethoxysilane, methylethyldimethoxysilane and γ-glycidoxypropyltriethoxysilane, methylethyldimethoxysilane and γ-methacryloxypropyltrimethoxysilane, methylethyldimethoxysilane and γ-methacryloxypropyltriethoxysilane, methylethyldimethoxysilane and triethoxy(4-(trifluoromethyl)phenyl)silane, methylethyldimethoxysilane and dodecyltriethoxysilane, methylethyldimethoxysilane and 3,3,3-trifluoropropyltrimethoxysilane, methylethyldimethoxysilane and (triethoxysilyl)cyclohexane, methylethyldimethoxysilane and perfluorooctylethyltriethoxysilane, methylethyldimethoxysilane and triethoxyfluorosilane, methylethyldimethoxysilane and tridecafluoro-1,1,2,2-tetrahydrooctyltriethoxysilane, methylethyldimethoxysilane and pentafluorophenylpropyltrimethoxysilane, methylethyldimethoxysilane and 3-(heptafluoroisopropoxy)propyltriethoxysilane, methylethyldimethoxysilane and heptadecafluoro-1,1,2,2-tetrahydrodecyltriethoxysilane, methylethyldimethoxysilane and triethoxy-2-thienylsilane, and methylethyldimethoxysilane and 3-(triethoxysilyl)furan.

(6) Diethyldimethoxysilane and methyltrimethoxysilane, diethyldimethoxysilane and methyltriethoxysilane, diethyldimethoxysilane and ethyltrimethoxysilane, diethyldimethoxysilane and ethyltriethoxysilane, diethyldimethoxysilane and propyltrimethoxysilane, diethyldimethoxysilane and propyltriethoxysilane, diethyldimethoxysilane and butyltrimethoxysilane, diethyldimethoxysilane and butyltriethoxysilane, diethyldimethoxysilane and pentyltrimethoxysilane, diethyldimethoxysilane and pentyltriethoxysilane, diethyldimethoxysilane and heptyltrimethoxysilane, diethyldimethoxysilane and heptyltriethoxysilane, diethyldimethoxysilane and octyltrimethoxysilane, diethyldimethoxysilane and octyltriethoxysilane, diethyldimethoxysilane and dodecyltrimethoxysilane, diethyldimethoxysilane and dodecyltriethoxysilane, diethyldimethoxysilane and hexadecyltrimethoxysilane, diethyldimethoxysilane and hexadecyltriethoxysilane, diethyldimethoxysilane and octadecyltrimethoxysilane, diethyldimethoxysilane and octadecyltriethoxysilane, diethyldimethoxysilane and phenyltrimethoxysilane, diethyldimethoxysilane and phenyltriethoxysilane, diethyldimethoxysilane and vinyltrimethoxysilane, diethyldimethoxysilane and vinyltriethoxysilane, diethyldimethoxysilane and γ-aminopropyltrimethoxysilane, diethyldimethoxysilane and γ-aminopropyltriethoxysilane, diethyldimethoxysilane and γ-glycidoxypropyltrimethoxysilane, diethyldimethoxysilane and γ-glycidoxypropyltriethoxysilane, diethyldimethoxysilane and γ-methacryloxypropyltrimethoxysilane, diethyldimethoxysilane and γ-methacryloxypropyltriethoxysilane, diethyldimethoxysilane and triethoxy(4-(trifluoromethyl)phenyl)silane, diethyldimethoxysilane and dodecyltriethoxysilane, diethyldimethoxysilane and 3,3,3- trifluoropropyltrimethoxysilane, diethyldimethoxysilane and (triethoxysilyl)cyclohexane, diethyldimethoxysilane and perfluorooctylethyltriethoxysilane, diethyldimethoxysilane and triethoxyfluorosilane, diethyldimethoxysilane and tridecafluoro-1,1,2,2-tetrahydrooctyltriethoxysilane, diethyldimethoxysilane and pentafluorophenylpropyltrimethoxysilane, diethyldimethoxysilane and 3-(heptafluoroisopropoxy)propyltriethoxysilane, diethyldimethoxysilane and heptadecafluoro-1,1,2,2-tetrahydrodecyltriethoxysilane, diethyldimethoxysilane and triethoxy-2-thienylsilane, and 3-(triethoxysilyl)furan.

(7) Diethyldiethoxysilane and methyltrimethoxysilane, diethyldiethoxysilane and methyltriethoxysilane, diethyldiethoxysilane and ethyltrimethoxysilane, diethyldiethoxysilane and ethyltriethoxysilane, diethyldiethoxysilane and propyltrimethoxysilane, diethyldiethoxysilane and propyltriethoxysilane, diethyldiethoxysilane and butyltrimethoxysilane, diethyldiethoxysilane and butyltriethoxysilane, diethyldiethoxysilane and pentyltrimethoxysilane, diethyldiethoxysilane and pentyltriethoxysilane, diethyldiethoxysilane and heptyltrimethoxysilane, diethyldiethoxysilane and heptyltriethoxysilane, diethyldiethoxysilane and octyltrimethoxysilane, diethyldiethoxysilane and octyitriethoxysilane, diethyldiethoxysilane and dodecyltrimethoxysilane, diethyldiethoxysilane and dodecyltriethoxysilane, diethyldiethoxysilane and hexadecyltrimethoxysilane, diethyldiethoxysilane and hexadecyltriethoxysilane, diethyldiethoxysilane and octadecyltrimethoxysilane, diethyldiethoxysilane and octadecyltriethoxysilane, diethyldiethoxysilane and phenyltrimethoxysilane, diethyldiethoxysilane and phenyltriethoxysilane, diethyldiethoxysilane and vinyltrimethoxysilane, diethyldiethoxysilane and vinyltriethoxysilane, diethyldiethoxysilane and γ-aminopropyltrimethoxysilane, diethyldiethoxysilane and γ-aminopropyltriethoxysilane, diethyldiethoxysilane and γ-glycidoxypropyltrimethoxysilane, diethyldiethoxysilane and γ-glycidoxypropyltriethoxysilane, diethyldiethoxysilane and γ-methacryloxypropyltrimethoxysilane, diethyldiethoxysilane and γ-methacryloxypropyltriethoxysilane, diethyldiethoxysilane and triethoxy(4-(trifluoromethyl)phenyl)silane, diethyldiethoxysilane and dodecyltriethoxysilane, diethyldiethoxysilane and 3,3,3-trifluoropropyltrimethoxysilane, diethyldiethoxysilane and (triethoxysilyl)cyclohexane, diethyldiethoxysilane and perfluorooctylethyltriethoxysilane, diethyldiethoxysilane and triethoxyfluorosilane, diethyldiethoxysilane and tridecafluoro-1,1,2,2-tetrahydrooctyltriethoxysilane, diethyldiethoxysilane and pentafluorophenylpropyltrimethoxysilane, diethyldiethoxysilane and 3-(heptafluoroisopropoxy)propyltriethoxysilane, diethyldiethoxysilane and heptadecafluoro-1,1,2,2-tetrahydrodecyltriethoxysilane, diethyldiethoxysilane and triethoxy-2-thienylsilane, and 3-(triethoxysilyl)furan.

(8) Methylpropyldimethoxysilane and methyltrimethoxysilane, methylpropyldimethoxysilane and methyltriethoxysilane, methylpropyldimethoxysilane and ethyltrimethoxysilane, methylpropyldimethoxysilane and ethyltriethoxysilane, methylpropyldimethoxysilane and propyltrimethoxysilane, methylpropyldimethoxysilane and propyltriethoxysilane, methylpropyldimethoxysilane and butyltrimethoxysilane, methylpropyldimethoxysilane and butyltriethoxysilane, methylpropyldimethoxysilane and pentyltrimethoxysilane, methylpropyldimethoxysilane and pentyltriethoxysilane, methylpropyldimethoxysilane and heptyltrimethoxysilane, methylpropyldimethoxysilane and heptyltriethoxysilane, methylpropyldimethoxysilane and octyltrimethoxysilane, methylpropyldimethoxysilane and octyltriethoxysilane, methylpropyldimethoxysilane and dodecyltrimethoxysilane, methylpropyldimethoxysilane and dodecyltriethoxysilane, methylpropyldimethoxysilane and hexadecyltrimethoxysilane, methylpropyldimethoxysilane and hexadecyltriethoxysilane, methylpropyldimethoxysilane and octadecyltrimethoxysilane, methylpropyldimethoxysilane and octadecyltriethoxysilane, methylpropyldimethoxysilane and phenyltrimethoxysilane, methylpropyldimethoxysilane and phenyltriethoxysilane, methylpropyldimethoxysilane and vinyltrimethoxysilane, methylpropyldimethoxysilane and vinyltriethoxysilane, methylpropyldimethoxysilane and γ-aminopropyltrimethoxysilane, methylpropyldimethoxysilane and γ-aminopropyltriethoxysilane, methylpropyldimethoxysilane and γ-glycidoxypropyltrimethoxysilane, methylpropyldimethoxysilane and γ-glycidoxypropyltriethoxysilane, methylpropyldimethoxysilane and γ-methacryloxypropyltrimethoxysilane, methylpropyldimethoxysilane and γ-methacryloxypropyltriethoxysilane, methylpropyldimethoxysilane and triethoxy(4-(trifluoromethyl)phenyl)silane, methylpropyldimethoxysilane and dodecyltriethoxysilane, methylpropyldimethoxysilane and 3,3,3-trifluoropropyltrimethoxysilane, methylpropyldimethoxysilane and (triethoxysilyl)cyclohexane, methylpropyldimethoxysilane and perfluorooctylethyltriethoxysilane, methylpropyldimethoxysilane and triethoxyfluorosilane, methylpropyldimethoxysilane and tridecafluoro-1,1,2,2-tetrahydrooctyltriethoxysilane, methylpropyldimethoxysilane and pentafluorophenylpropyltrimethoxysilane, methylpropyldimethoxysilane and 3-(heptafluoroisopropoxy)propyltriethoxysilane, methylpropyldimethoxysilane and heptadecafluoro-1,1,2,2-tetrahydrodecyltriethoxysilane, methylpropyldimethoxysilane and triethoxy-2-thienylsilane, and methylpropyldimethoxysilane and 3-(triethoxysilyl)furan.

(9) Methylpropyldiethoxysilane and methyltrimethoxysilane, methylpropyldiethoxysilane and methyltriethoxysilane, methylpropyldiethoxysilane and ethyltrimethoxysilane, methylpropyldiethoxysilane and ethyltriethoxysilane, methylpropyldiethoxysilane and propyltrimethoxysilane, methylpropyldiethoxysilane and propyltriethoxysilane, methylpropyldiethoxysilane and butyltrimethoxysilane, methylpropyldiethoxysilane and butyltriethoxysilane, methylpropyldiethoxysilane and pentyltrimethoxysilane, methylpropyldiethoxysilane and pentyltriethoxysilane, methylpropyldiethoxysilane and heptyltrimethoxysilane, methylpropyldiethoxysilane and heptyltriethoxysilane, methylpropyldiethoxysilane and octyltrimethoxysilane, methylpropyldiethoxysilane and octyltriethoxysilane, methylpropyldiethoxysilane and dodecyltrimethoxysilane, methylpropyldiethoxysilane and dodecyltriethoxysilane, methylpropyldiethoxysilane and hexadecyltrimethoxysilane, methylpropyldiethoxysilane and hexadecyltriethoxysilane, methylpropyldiethoxysilane and octadecyltrimethoxysilane, methylpropyldiethoxysilane and octadecyltriethoxysilane, methylpropyldiethoxysilane and phenyltrimethoxysilane, methylpropyldiethoxysilane and phenyltriethoxysilane, methylpropyldiethoxysilane and vinyltrimethoxysilane, methylpropyldiethoxysilane and vinyltriethoxysilane, methylpropyldiethoxysilane and γ-aminopropyltrimethoxysilane, methylpropyldiethoxysilane and γ-aminopropyltriethoxysilane, methylpropyldiethoxysilane and γ-glycidoxypropyltrimethoxysilane, methylpropyldiethoxysilane and γ-glycidoxypropyltriethoxysilane, methylpropyldiethoxysilane and γ-methacryloxypropyltrimethoxysilane, methylpropyldiethoxysilane and γ-methacryloxypropyltriethoxysilane, methylpropyldiethoxysilane and triethoxy(4-(trifluoromethyl)phenyl)silane, methylpropyldiethoxysilane and dodecyltriethoxysilane, methylpropyldiethoxysilane and 3,3,3-trifluoropropyltrimethoxysilane, methylpropyldiethoxysilane and (triethoxysilyl)cyclohexane, methylpropyldiethoxysilane and perfluorooctylethyltriethoxysilane, methylpropyldiethoxysilane and triethoxyfluorosilane, methylpropyldiethoxysilane and tridecafluoro-1,1,2,2-tetrahydrooctyltriethoxysilane, methylpropyldiethoxysilane and pentafluorophenylpropyltrimethoxysilane, methylpropyldiethoxysilane and 3-(heptafluoroisopropoxy)propyltriethoxysilane, methylpropyldiethoxysilane and heptadecafluoro-1,1,2,2-tetrahydrodecyltriethoxysilane, methylpropyldiethoxysilane and triethoxy-2-thienylsilane, and methylpropyldiethoxysilane and 3-(triethoxysilyl)furan.

(10) Diisopropyldimethoxysilane and methyltrimethoxysilane, diisopropyldimethoxysilane and methyltriethoxysilane, diisopropyldimethoxysilane and ethyltrimethoxysilane, diisopropyldimethoxysilane and ethyltriethoxysilane, diisopropyldimethoxysilane and propyltrimethoxysilane, diisopropyldimethoxysilane and propyltriethoxysilane, diisopropyldimethoxysilane and butyltrimethoxysilane, diisopropyldimethoxysilane and butyltriethoxysilane, diisopropyldimethoxysilane and pentyltrimethoxysilane, diisopropyldimethoxysilane and pentyltriethoxysilane, diisopropyldimethoxysilane and heptyltrimethoxysilane, diisopropyldimethoxysilane and heptyltriethoxysilane, diisopropyldimethoxysilane and octyltrimethoxysilane, diisopropyldimethoxysilane and octyltriethoxysilane, diisopropyldimethoxysilane and dodecyltrimethoxysilane, diisopropyldimethoxysilane and dodecyltriethoxysilane, diisopropyldimethoxysilane and hexadecyltrimethoxysilane, diisopropyldimethoxysilane and hexadecyltriethoxysilane, diisopropyldimethoxysilane and octadecyltrimethoxysilane, diisopropyldimethoxysilane and octadecyltriethoxysilane, diisopropyldimethoxysilane and phenyltrimethoxysilane, diisopropyldimethoxysilane and phenyltriethoxysilane, diisopropyldimethoxysilane and vinyltrimethoxysilane, diisopropyldimethoxysilane and vinyltriethoxysilane, diisopropyldimethoxysilane and γ-aminopropyltrimethoxysilane, diisopropyldimethoxysilane and γ-aminopropyltriethoxysilane, diisopropyldimethoxysilane and γ-glycidoxypropyltrimethoxysilane, diisopropyldimethoxysilane and γ-glycidoxypropyltriethoxysilane, diisopropyldimethoxysilane and γ-methacryloxypropyltrimethoxysilane, diisopropyldimethoxysilane and γ-methacryloxypropyltriethoxysilane, diisopropyldimethoxysilane and triethoxy(4-(trifluoromethyl)phenyl)silane, diisopropyldimethoxysilane and dodecyltriethoxysilane, diisopropyldimethoxysilane and 3,3,3-trifluoropropyltrimethoxysilane, diisopropyldimethoxysilane and (triethoxysilyl)cyclohexane, diisopropyldimethoxysilane and perfluorooctylethyltriethoxysilane, diisopropyldimethoxysilane and triethoxyfluorosilane, diisopropyldimethoxysilane and tridecafluoro-1,1,2,2-tetrahydrooctyltriethoxysilane, diisopropyldimethoxysilane and pentafluorophenylpropyltrimethoxysilane, diisopropyldimethoxysilane and 3-(heptafluoroisopropoxy)propyltriethoxysilane, diisopropyldimethoxysilane and heptadecafluoro-1,1,2,2-tetrahydrodecyltriethoxysilane, diisopropyldimethoxysilane and triethoxy-2-thienylsilane, and diisopropyldimethoxysilane and 3-(triethoxysilyl)furan.

(11) Phenylmethyldimethoxysilane and methyltrimethoxysilane, phenylmethyldimethoxysilane and methyltriethoxysilane, phenylmethyldimethoxysilane and ethyltrimethoxysilane, phenylmethyldimethoxysilane and ethyltriethoxysilane, phenylmethyldimethoxysilane and propyltrimethoxysilane, phenylmethyldimethoxysilane and propyltriethoxysilane, phenylmethyldimethoxysilane and butyltrimethoxysilane, phenylmethyldimethoxysilane and butyltriethoxysilane, phenylmethyldimethoxysilane and pentyltrimethoxysilane, phenylmethyldimethoxysilane and pentyltriethoxysilane, phenylmethyldimethoxysilane and heptyltrimethoxysilane, phenylmethyldimethoxysilane and heptyltriethoxysilane, phenylmethyldimethoxysilane and octyltrimethoxysilane, phenylmethyldimethoxysilane and octyltriethoxysilane, phenylmethyldimethoxysilane and dodecyltrimethoxysilane, phenylmethyldimethoxysilane and dodecyltriethoxysilane, phenylmethyldimethoxysilane and hexadecyltrimethoxysilane, phenylmethyldimethoxysilane and hexadecyltriethoxysilane, phenylmethyldimethoxysilane and octadecyltrimethoxysilane, phenylmethyldimethoxysilane and octadecyltriethoxysilane, phenylmethyldimethoxysilane and phenyltrimethoxysilane, phenylmethyldimethoxysilane and phenyltriethoxysilane, phenylmethyldimethoxysilane and vinyltrimethoxysilane, phenylmethyldimethoxysilane and vinyltriethoxysilane, phenylmethyldimethoxysilane and γ-aminopropyltrimethoxysilane, phenylmethyldimethoxysilane and γ-aminopropyltriethoxysilane, phenylmethyldimethoxysilane and γ-glycidoxypropyltrimethoxysilane, phenylmethyldimethoxysilane and γ-glycidoxypropyltriethoxysilane, phenylmethyldimethoxysilane and γ-methacryloxypropyltrimethoxysilane, phenylmethyldimethoxysilane and γ-methacryloxypropyltriethoxysilane, phenylmethyldimethoxysilane and triethoxy(4-(trifluoromethyl)phenyl)silane, phenylmethyldimethoxysilane and dodecyltriethoxysilane, phenylmethyldimethoxysilane and 3,3,3-trifluoropropyltrimethoxysilane, phenylmethyldimethoxysilane and (triethoxysilyl)cyclohexane, phenylmethyldimethoxysilane and perfluorooctylethyltriethoxysilane, phenylmethyldimethoxysilane and triethoxyfluorosilane, phenylmethyldimethoxysilane and tridecafluoro-1,1,2,2-tetrahydrooctyltriethoxysilane, phenylmethyldimethoxysilane and pentafluorophenylpropyltrimethoxysilane, phenylmethyldimethoxysilane and 3-(heptafluoroisopropoxy)propyltriethoxysilane, phenylmethyldimethoxysilane and heptadecafluoro-1,1,2,2-tetrahydrodecyltriethoxysilane, phenylmethyldimethoxysilane and triethoxy-2-thienylsilane, and phenylmethyldimethoxysilane and 3-(triethoxysilyl)furan.

(12) Vinylmethyldimethoxysilane and methyltrimethoxysilane, vinylmethyldimethoxysilane and methyltriethoxysilane, vinylmethyldimethoxysilane and ethyltrimethoxysilane, vinylmethyldimethoxysilane and ethyltriethoxysilane, vinylmethyldimethoxysilane and propyltrimethoxysilane, vinylmethyldimethoxysilane and propyltriethoxysilane, vinylmethyldimethoxysilane and butyltrimethoxysilane, vinylmethyldimethoxysilane and butyltriethoxysilane, vinylmethyldimethoxysilane and pentyltrimethoxysilane, vinylmethyldimethoxysilane and pentyltriethoxysilane, vinylmethyldimethoxysilane and heptyltrimethoxysilane, vinylmethyldimethoxysilane and heptyltriethoxysilane, vinylmethyldimethoxysilane and octyltrimethoxysilane, vinylmethyldimethoxysilane and octyltriethoxysilane, vinylmethyldimethoxysilane and dodecyltrimethoxysilane, vinylmethyldimethoxysilane and dodecyltriethoxysilane, vinylmethyldimethoxysilane and hexadecyltrimethoxysilane, vinylmethyldimethoxysilane and hexadecyltriethoxysilane, vinylmethyldimethoxysilane and octadecyltrimethoxysilane, vinylmethyldimethoxysilane and octadecyltriethoxysilane, vinylmethyldimethoxysilane and phenyltrimethoxysilane, vinylmethyldimethoxysilane and phenyltriethoxysilane, vinylmethyldimethoxysilane and vinyltrimethoxysilane, vinylmethyldimethoxysilane and vinyltriethoxysilane, vinylmethyldimethoxysilane and γ-aminopropyltrimethoxysilane, vinylmethyldimethoxysilane and γ-aminopropyltriethoxysilane, vinylmethyldimethoxysilane and γ-glycidoxypropyltrimethoxysilane, vinylmethyldimethoxysilane and γ-glycidoxypropyltriethoxysilane, vinylmethyldimethoxysilane and γ-methacryloxypropyltrimethoxysilane, vinylmethyldimethoxysilane and γ-methacryloxypropyltriethoxysilane, vinylmethyldimethoxysilane and triethoxy(4-(trifluoromethyl)phenyl)silane, vinylmethyldimethoxysilane and dodecyltriethoxysilane, vinylmethyldimethoxysilane and 3,3,3-trifluoropropyltrimethoxysilane, vinylmethyldimethoxysilane and (triethoxysilyl)cyclohexane, vinylmethyldimethoxysilane and perfluorooctylethyltriethoxysilane, vinylmethyldimethoxysilane and triethoxyfluorosilane, vinylmethyldimethoxysilane and tridecafluoro-1,1,2,2-tetrahydrooctyltriethoxysilane, vinylmethyldimethoxysilane and pentafluorophenylpropyltrimethoxysilane, vinylmethyldimethoxysilane and 3-(heptafluoroisopropoxy)propyltriethoxysilane, vinylmethyldimethoxysilane and heptadecafluoro-1,1,2,2-tetrahydrodecyltriethoxysilane, vinylmethyldimethoxysilane and triethoxy-2-thienylsilane, and vinylmethyldimethoxysilane and 3-(triethoxysilyl)furan.

(13) γ-glycidoxypropylmethyldimethoxysilane and methyltrimethoxysilane, γ-glycidoxypropylmethyldimethoxysilane and methyltriethoxysilane, γ-glycidoxypropylmethyldimethoxysilane and ethyltrimethoxysilane, γ-glycidoxypropylmethyldimethoxysilane and ethyltriethoxysilane, γ-glycidoxypropylmethyldimethoxysilane and propyltrimethoxysilane, γ-glycidoxypropylmethyldimethoxysilane and propyltriethoxysilane, γ-glycidoxypropylmethyldimethoxysilane and butyltrimethoxysilane, γ-glycidoxypropylmethyldimethoxysilane and butyltriethoxysilane, γ-glycidoxypropylmethyldimethoxysilane and pentyltrimethoxysilane, γ-glycidoxypropylmethyldimethoxysilane and pentyltriethoxysilane, γ-glycidoxypropylmethyldimethoxysilane and heptyltrimethoxysilane, γ-glycidoxypropylmethyldimethoxysilane and heptyltriethoxysilane, γ-glycidoxypropylmethyldimethoxysilane and octyltrimethoxysilane, γ-glycidoxypropylmethyldimethoxysilane and octyltriethoxysilane, γ-glycidoxypropylmethyldimethoxysilane and dodecyltrimethoxysilane, γ-glycidoxypropylmethyldimethoxysilane and dodecyltriethoxysilane, γ-glycidoxypropylmethyldimethoxysilane and hexadecyltrimethoxysilane, γ-glycidoxypropylmethyldimethoxysilane and hexadecyltriethoxysilane, γ-glycidoxypropylmethyldimethoxysilane and octadecyltrimethoxysilane, γ-glycidoxypropylmethyldimethoxysilane and octadecyltriethoxysilane, γ-glycidoxypropylmethyldimethoxysilane and phenyltrimethoxysilane, γ-glycidoxypropylmethyldimethoxysilane and phenyltriethoxysilane, γ-glycidoxypropylmethyldimethoxysilane and vinyltrimethoxysilane, γ-glycidoxypropylmethyldimethoxysilane and vinyltriethoxysilane, γ-glycidoxypropylmethyldimethoxysilane and γ-aminopropyltrimethoxysilane, γ-glycidoxypropylmethyldimethoxysilane and γ-aminopropyltriethoxysilane, γ-glycidoxypropylmethyldimethoxysilane and γ-glycidoxypropyltrimethoxysilane, γ-glycidoxypropylmethyldimethoxysilane and γ-glycidoxypropyltriethoxysilane, γ-glycidoxypropylmethyldimethoxysilane and γ-methacryloxypropyltrimethoxysilane, γ-glycidoxypropylmethyldimethoxysilane and γ-methacryloxypropyltriethoxysilane, γ-glycidoxypropylmethyldimethoxysilane and triethoxy(4-(trifluoromethyl)phenyl)silane, γ-glycidoxypropylmethyidimethoxysilane and dodecyltriethoxysilane, γ-glycidoxypropylmethyldimethoxysilane and 3,3,3-trifluoropropyltrimethoxysilane, γ-glycidoxypropylmethyldimethoxysilane and (triethoxysilyl)cyclohexane, γ-glycidoxypropylmethyldimethoxysilane and perfluorooctylethyltriethoxysilane, γ-glycidoxypropylmethyldimethoxysilane and triethoxyfluorosilane, γ-glycidoxypropylmethyldimethoxysilane and tridecafluoro-1,1,2,2-tetrahydrooctyltriethoxysilane, γ-glycidoxypropylmethyldimethoxysilane and pentafluorophenylpropyltrimethoxysilane, γ-glycidoxypropylmethyldimethoxysilane and 3-(heptafluoroisopropoxy)propyltriethoxysilane, γ-glycidoxypropylmethyldimethoxysilane and heptadecafluoro-1,1,2,2-tetrahydrodecyltriethoxysilane, γ-glycidoxypropylmethyldimethoxysilane and triethoxy-2-thienylsilane, and γ-glycidoxypropylmethyldimethoxysilane and 3-(triethoxysilyl)furan.

(14) γ-glycidoxypropylmethyldiethoxysilane and methyltrimethoxysilane, γ-glycidoxypropylmethyldiethoxysilane and methyltriethoxysilane, γ-glycidoxypropylmethyldiethoxysilane and ethyltrimethoxysilane, γ-glycidoxypropylmethyldiethoxysilane and ethyltriethoxysilane, γ-glycidoxypropylmethyldiethoxysilane and propyltrimethoxysilane, γ-glycidoxypropylmethyldiethoxysilane and propyltriethoxysilane, γ-glycidoxypropylmethyldiethoxysilane and butyltrimethoxysilane, γ-glycidoxypropylmethyldiethoxysilane and butyltriethoxysilane, γ-glycidoxypropylmethyldiethoxysilane and pentyltrimethoxysilane, γ-glycidoxypropylmethyldiethoxysilane and pentyltriethoxysilane, γ-glycidoxypropylmethyldiethoxysilane and heptyltrimethoxysilane, γ-glycidoxypropylmethyldiethoxysilane and heptyltriethoxysilane, γ-glycidoxypropylmethyldiethoxysilane and octyltrimethoxysilane, γ-glycidoxypropylmethyldiethoxysilane and octyltriethoxysilane, γ-glycidoxypropylmethyldiethoxysilane and dodecyltrimethoxysilane, γ-glycidoxypropylmethyldiethoxysilane and dodecyltriethoxysilane, γ-glycidoxypropylmethyldiethoxysilane and hexadecyltrimethoxysilane, γ-glycidoxypropylmethyldiethoxysilane and hexadecyltriethoxysilane, γ-glycidoxypropylmethyldiethoxysilane and octadecyltrimethoxysilane, γ-glycidoxypropylmethyldiethoxysilane and octadecyltriethoxysilane, γ-glycidoxypropylmethyldiethoxysilane and phenyltrimethoxysilane, γ-glycidoxypropylmethyldiethoxysilane and phenyltriethoxysilane, γ-glycidoxypropylmethyldiethoxysilane and vinyltrimethoxysilane, γ-glycidoxypropylmethyldiethoxysilane and vinyltriethoxysilane, γ-glycidoxypropylmethyldiethoxysilane and γ-aminopropyltrimethoxysilane, γ-glycidoxypropylmethyldiethoxysilane and γ-aminopropyltriethoxysilane, γ-glycidoxypropylmethyldiethoxysilane and γ-glycidoxypropyltrimethoxysilane, γ-glycidoxypropylmethyldiethoxysilane and γ-glycidoxypropyltriethoxysilane, γ-glycidoxypropylmethyldiethoxysilane and γ-methacryloxypropyltrimethoxysilane, γ-glycidoxypropylmethyldiethoxysilane and γ-methacryloxypropyltriethoxysilane, γ-glycidoxypropylmethyldiethoxysilane and triethoxy(4-(trifluoromethyl)phenyl)silane, γ-glycidoxypropylmethyldiethoxysilane and dodecyltriethoxysilane, γ-glycidoxypropylmethyldiethoxysilane and 3,3,3-trifluoropropyltrimethoxysilane, γ-glycidoxypropylmethyldiethoxysilane and (triethoxysilyl)cyclohexane, γ-glycidoxypropylmethyldiethoxysilane and perfluorooctylethyltriethoxysilane, γ-glycidoxypropylmethyldiethoxysilane and triethoxyfluorosilane, γ-glycidoxypropylmethyldiethoxysilane and tridecafluoro-1,1,2,2-tetrahydrooctyltriethoxysilane, γ-glycidoxypropylmethyldiethoxysilane and pentafluorophenylpropyltrimethoxysilane, γ-glycidoxypropylmethyldiethoxysilane and 3-(heptafluoroisopropoxy)propyltriethoxysilane, γ-glycidoxypropylmethyldiethoxysilane and heptadecafluoro-1,1,2,2-tetrahydrodecyltriethoxysilane, γ-glycidoxypropylmethyldiethoxysilane and triethoxy-2-thienylsilane, and γ-glycidoxypropylmethyldiethoxysilane and 3-(triethoxysilyl)furan.

(15) β-(3,4-epoxycyclohexyl)ethylmethyldimethoxysilane and methyltrimethoxysilane, β-(3,4-epoxycyclohexyl)ethylmethyldimethoxysilane and methyltriethoxysilane, β-(3,4-epoxycyclohexyl)ethylmethyldimethoxysilane and ethyltrimethoxysilane, β-(3,4-epoxycyclohexyl)ethylmethyldimethoxysilane and ethyltriethoxysilane, β-(3,4-epoxycyclohexyl)ethylmethyldimethoxysilane and propyltrimethoxysilane, β-(3,4-epoxycyclohexyl)ethylmethyldimethoxysilane and propyltriethoxysilane, β-(3,4-epoxycyclohexyl)ethylmethyldimethoxysilane and butyltrimethoxysilane, β-(3,4-epoxycyclohexyl)ethylmethyldimethoxysilane and butyltriethoxysilane, β-(3,4-epoxycyclohexyl)ethylmethyldimethoxysilane and pentyltrimethoxysilane, β-(3,4-epoxycyclohexyl)ethylmethyldimethoxysilane and pentyltriethoxysilane, β-(3,4-epoxycyclohexyl)ethylmethyldimethoxysilane and heptyltrimethoxysilane, β-(3,4-epoxycyclohexyl)ethylmethyldimethoxysilane and heptyltriethoxysilane, β-(3,4-epoxycyclohexyl)ethylmethyldimethoxysilane and octyltrimethoxysilane, β-(3,4-epoxycyclohexyl)ethylmethyldimethoxysilane and octyltriethoxysilane, β-(3,4-epoxycyclohexyl)ethylmethyldimethoxysilane and dodecyltrimethoxysilane, β-(3,4-epoxycyclohexyl)ethylmethyldimethoxysilane and dodecyltriethoxysilane, β-(3,4-epoxycyclohexyl)ethylmethyldimethoxysilane and hexadecyltrimethoxysilane, β-(3,4-epoxycyclohexyl)ethylmethyldimethoxysilane and hexadecyltriethoxysilane, β-(3,4-epoxycyclohexyl)ethylmethyldimethoxysilane and octadecyltrimethoxysilane, β-(3,4-epoxycyclohexyl)ethylmethyldimethoxysilane and octadecyltriethoxysilane, β-(3,4-epoxycyclohexyl)ethylmethyldimethoxysilane and phenyltrimethoxysilane, β-(3,4-epoxycyclohexyl)ethylmethyldimethoxysilane and phenyltriethoxysilane, β-(3,4-epoxycyclohexyl)ethylmethyldimethoxysilane and vinyltrimethoxysilane, β-(3,4-epoxycyclohexyl)ethylmethyldimethoxysilane and vinyltriethoxysilane, β-(3,4-epoxycyclohexyl)ethylmethyldimethoxysilane and γ-aminopropyltrimethoxysilane, β-(3,4-epoxycyclohexyl)ethylmethyldimethoxysilane and γ-aminopropyltriethoxysilane, β-(3,4-epoxycyclohexyl)ethylmethyldimethoxysilane and γ-glycidoxypropyltrimethoxysilane, β-(3,4-epoxycyclohexyl)ethylmethyldimethoxysilane and γ-glycidoxypropyltriethoxysilane, β-(3,4-epoxycyclohexyl)ethylmethyldimethoxysilane and γ-methacryloxypropyltrimethoxysilane, β-(3,4-epoxycyclohexyl)ethylmethyldimethoxysilane and γ-methacryloxypropyltriethoxysilane, β-(3,4-epoxycyclohexyl)ethylmethyldimethoxysilane and triethoxy(4-(trifluoromethyl)phenyl)silane, β-(3,4-epoxycyclohexyl)ethylmethyldimethoxysilane and dodecyltriethoxysilane, β-(3,4-epoxycyclohexyl)ethylmethyldimethoxysilane and 3,3,3-trifluoropropyltrimethoxysilane, β-(3,4-epoxycyclohexyl)ethylmethyldimethoxysilane and (triethoxysilyl)cyclohexane, β-(3,4-epoxycyclohexyl)ethylmethyldimethoxysilane and perfluorooctylethyltriethoxysilane, β-(3,4-epoxycyclohexyl)ethylmethyldimethoxysilane and triethoxyfluorosilane, β-(3,4-epoxycyclohexyl)ethylmethyldimethoxysilane and tridecafluoro-1,1,2,2-tetrahydrooctyltriethoxysilane, β-(3,4-epoxycyclohexyl)ethylmethyldimethoxysilane and pentafluorophenylpropyltrimethoxysilane, β-(3,4-epoxycyclohexyl)ethylmethyldimethoxysilane and 3-(heptafluoroisopropoxy)propyltriethoxysilane, β-(3,4-epoxycyclohexyl)ethylmethyldimethoxysilane and heptadecafluoro-1,1,2,2-tetrahydrodecyltriethoxysilane, β-(3,4-epoxycyclohexyl)ethylmethyldimethoxysilane and triethoxy-2-thienylsilane, and β-(3,4-epoxycyclohexyl)ethylmethyldimethoxysilane and 3-(triethoxysilyl)furan.

(16) γ-methacryloxypropylmethyldimethoxysilane and methyltrimethoxysilane, γ-methacryloxypropylmethyldimethoxysilane and methyltriethoxysilane, γ-methacryloxypropylmethyldimethoxysilane and ethyltrimethoxysilane, γ-methacryloxypropylmethyldimethoxysilane and ethyltriethoxysilane, γ-methacryloxypropylmethyldimethoxysilane and propyltrimethoxysilane, γ-methacryloxypropylmethyldimethoxysilane and propyltriethoxysilane, γ-methacryloxypropylmethyldimethoxysilane and butyltrimethoxysilane, γ-methacryloxypropylmethyldimethoxysilane and butyltriethoxysilane, γ-methacryloxypropylmethyldimethoxysilane and pentyltrimethoxysilane, γ-methacryloxypropylmethyldimethoxysilane and pentyltriethoxysilane, γ-methacryloxypropylmethyldimethoxysilane and heptyltrimethoxysilane, γ-methacryloxypropylmethyldimethoxysilane and heptyltriethoxysilane, γ-methacryloxypropylmethyldimethoxysilane and octyltrimethoxysilane, γ-methacryloxypropylmethyldimethoxysilane and octyltriethoxysilane, γ-methacryloxypropylmethyldimethoxysilane and dodecyltrimethoxysilane, γ-methacryloxypropylmethyldimethoxysilane and dodecyltriethoxysilane, γ-methacryloxypropylmethyldimethoxysilane and hexadecyltrimethoxysilane, γ-methacryloxypropylmethyldimethoxysilane and hexadecyltriethoxysilane, γ-methacryloxypropylmethyldimethoxysilane and octadecyltrimethoxysilane, γ-methacryloxypropylmethyldimethoxysilane and octadecyltriethoxysilane, γ-methacryloxypropylmethyldimethoxysilane and phenyltrimethoxysilane, γ-methacryloxypropylmethyldimethoxysilane and phenyltriethoxysilane, γ-methacryloxypropylmethyldimethoxysilane and vinyltrimethoxysilane, γ-methacryloxypropylmethyldimethoxysilane and vinyltriethoxysilane, γ-methacryloxypropylmethyldimethoxysilane and γ-aminopropyltrimethoxysilane, γ-methacryloxypropylmethyldimethoxysilane and γ-aminopropyltriethoxysilane, γ-methacryloxypropylmethyldimethoxysilane and γ-glycidoxypropyltrimethoxysilane, γ-methacryloxypropylmethyldimethoxysilane and γ-glycidoxypropyltriethoxysilane, γ-methacryloxypropylmethyldimethoxysilane and γ-methacryloxypropyltrimethoxysilane, γ-methacryloxypropylmethyldimethoxysilane and γ-methacryloxypropyltriethoxysilane, γ-methacryloxypropylmethyldimethoxysilane and triethoxy(4-(trifluoromethyl)phenyl)silane, γ-methacryloxypropylmethyldimethoxysilane and dodecyltriethoxysilane, γ-methacryloxypropylmethyldimethoxysilane and 3,3,3-trifluoropropyltrimethoxysilane, γ-methacryloxypropylmethyldimethoxysilane and (triethoxysilyl)cyclohexane, γ-methacryloxypropylmethyldimethoxysilane and perfluorooctylethyltriethoxysilane, γ-methacryloxypropylmethyldimethoxysilane and triethoxyfluorosilane, γ-methacryloxypropylmethyldimethoxysilane and tridecafluoro-1,1,2,2-tetrahydrooctyltriethoxysilane, γ-methacryloxypropylmethyldimethoxysilane and pentafluorophenylpropyltrimethoxysilane, γ-methacryloxypropylmethyldimethoxysilane and 3-(heptafluoroisopropoxy)propyltriethoxysilane, γ-methacryloxypropylmethyldimethoxysilane and heptadecafluoro-1,1,2,2-tetrahydrodecyltriethoxysilane, γ-methacryloxypropylmethyldimethoxysilane and triethoxy-2-thienylsilane, and γ-methacryloxypropylmethyldimethoxysilane and 3-(triethoxysilyl)furan.

(17) γ-methacryloxypropylmethyldiethoxysilane and methyltrimethoxysilane, γ-methacryloxypropylmethyldiethoxysilane and methyltriethoxysilane, γ-methacryloxypropylmethyldiethoxysilane and ethyltrimethoxysilane, γ-methacryloxypropylmethyldiethoxysilane and ethyltriethoxysilane, γ-methacryloxypropylmethyldiethoxysilane and propyltrimethoxysilane, γ-methacryloxypropylmethyldiethoxysilane and propyltriethoxysilane, γ-methacryloxypropylmethyldiethoxysilane and butyltrimethoxysilane, γ-methacryloxypropylmethyldiethoxysilane and butyltriethoxysilane, γ-methacryloxypropylmethyldiethoxysilane and pentyltrimethoxysilane, γ-methacryloxypropylmethyldiethoxysilane and pentyltriethoxysilane, γ-methacryloxypropylmethyldiethoxysilane and heptyltrimethoxysilane, γ-methacryloxypropylmethyldiethoxysilane and heptyltriethoxysilane, γ-methacryloxypropylmethyldiethoxysilane and octyltrimethoxysilane, γ-methacryloxypropylmethyldiethoxysilane and octyltriethoxysilane, γ-methacryloxypropylmethyldiethoxysilane and dodecyltrimethoxysilane, γ-methacryloxypropylmethyldiethoxysilane and dodecyltriethoxysilane, γ-methacryloxypropylmethyldiethoxysilane and hexadecyltrimethoxysilane, γ-methacryloxypropylmethyldiethoxysilane and hexadecyltriethoxysilane, γ-methacryloxypropylmethyldiethoxysilane and octadecyltrimethoxysilane, γ-methacryloxypropylmethyldiethoxysilane and octadecyltriethoxysilane, γ-methacryloxypropylmethyldiethoxysilane and phenyltrimethoxysilane, γ-methacryloxypropylmethyldiethoxysilane and phenyltriethoxysilane, γ-methacryloxypropylmethyldiethoxysilane and vinyltrimethoxysilane, γ-methacryloxypropylmethyldiethoxysilane and vinyltriethoxysilane, γ-methacryloxypropylmethyldiethoxysilane and γ-aminopropyltrimethoxysilane, γ-methacryloxypropylmethyldiethoxysilane and γ-aminopropyltriethoxysilane, γ-methacryloxypropylmethyldiethoxysilane and γ-glycidoxypropyltrimethoxysilane, γ-methacryloxypropylmethyldiethoxysilane and γ-glycidoxypropyltriethoxysilane, γ-methacryloxypropylmethyldiethoxysilane and γ-methacryloxypropyltrimethoxysilane, γ-methacryloxypropylmethyldiethoxysilane and γ-methacryloxypropyltriethoxysilane, γ-methacryloxypropylmethyldiethoxysilane and triethoxy(4-(trifluoromethyl)phenyl)silane, γ-methacryloxypropylmethyldiethoxysilane and dodecyltriethoxysilane, γ-methacryloxypropylmethyldiethoxysilane and 3,3,3-trifluoropropyltrimethoxysilane, γ-methacryloxypropylmethyldiethoxysilane and (triethoxysilyl)cyclohexane, γ-methacryloxypropylmethyldiethoxysilane and perfluorooctylethyltriethoxysilane, γ-methacryloxypropylmethyldiethoxysilane and triethoxyfluorosilane, γ-methacryloxypropylmethyldiethoxysilane and tridecafluoro-1,1,2,2-tetrahydrooctyltriethoxysilane, γ-methacryloxypropylmethyldiethoxysilane and pentafluorophenylpropyltrimethoxysilane, γ-methacryloxypropylmethyldiethoxysilane and 3-(heptafluoroisopropoxy)propyltriethoxysilane, γ-methacryloxypropylmethyldiethoxysilane and heptadecafluoro-1,1,2,2-tetrahydrodecyltriethoxysilane, γ-methacryloxypropylmethyldiethoxysilane and triethoxy-2-thienylsilane, and γ-methacryloxypropylmethyldiethoxysilane and 3-(triethoxysilyl)furan.

(18) γ-mercaptopropylmethyldimethoxysilane and methyltrimethoxysilane, γ-mercaptopropylmethyldimethoxysilane and methyltriethoxysilane, γ-mercaptopropylmethyldimethoxysilane and ethyltrimethoxysilane, γ-mercaptopropylmethyldimethoxysilane and ethyltriethoxysilane, γ-mercaptopropylmethyldimethoxysilane and propyltrimethoxysilane, γ-mercaptopropylmethyldimethoxysilane and propyltriethoxysilane, γ-mercaptopropylmethyldimethoxysilane and butyltrimethoxysilane, γ-mercaptopropylmethyldimethoxysilane and butyltriethoxysilane, γ-mercaptopropylmethyldimethoxysilane and pentyltrimethoxysilane, γ-mercaptopropylmethyldimethoxysilane and pentyltriethoxysilane, γ-mercaptopropylmethyldimethoxysilane and heptyltrimethoxysilane, γ-mercaptopropylmethyldimethoxysilane and heptyltriethoxysilane, γ-mercaptopropylmethyldimethoxysilane and octyltrimethoxysilane, γ-mercaptopropylmethyldimethoxysilane and octyltriethoxysilane, γ-mercaptopropylmethyldimethoxysilane and dodecyltrimethoxysilane, γ-mercaptopropylmethyldimethoxysilane and dodecyltriethoxysilane, γ-mercaptopropylmethyldimethoxysilane and hexadecyltrimethoxysilane, γ-mercaptopropylmethyldimethoxysilane and hexadecyltriethoxysilane, γ-mercaptopropylmethyldimethoxysilane and octadecyltrimethoxysilane, γ-mercaptopropylmethyldimethoxysilane and octadecyltriethoxysilane, γ-mercaptopropylmethyldimethoxysilane and phenyltrimethoxysilane, γ-mercaptopropylmethyldimethoxysilane and phenyltriethoxysilane, γ-mercaptopropylmethyldimethoxysilane and vinyltrimethoxysilane, γ-mercaptopropylmethyldimethoxysilane and vinyltriethoxysilane, γ-mercaptopropylmethyldimethoxysilane and γ-aminopropyltrimethoxysilane, γ-mercaptopropylmethyldimethoxysilane and γ-aminopropyltriethoxysilane, γ-mercaptopropylmethyldimethoxysilane and γ-glycidoxypropyltrimethoxysilane, γ-mercaptopropylmethyldimethoxysilane and γ-glycidoxypropyltriethoxysilane, γ-mercaptopropylmethyldimethoxysilane and γ-methacryloxypropyltrimethoxysilane, γ-mercaptopropylmethyldimethoxysilane and γ-methacryloxypropyltriethoxysilane, γ-mercaptopropylmethyldimethoxysilane and triethoxy(4-(trifluoromethyl)phenyl)silane, γ-mercaptopropylmethyldimethoxysilane and dodecyltriethoxysilane, γ-mercaptopropylmethyldimethoxysilane 3,3,3-trifluoropropyltrimethoxysilane, γ-mercaptopropylmethyldimethoxysilane and (triethoxysilyl)cyclohexane, γ-mercaptopropylmethyldimethoxysilane and perfluorooctylethyltriethoxysilane, γ-mercaptopropylmethyldimethoxysilane and triethoxyfluorosilane, γ-mercaptopropylmethyldimethoxysilane and tridecafluoro-1,1,2,2-tetrahydrooctyltriethoxysilane, γ-mercaptopropylmethyldimethoxysilane and pentafluorophenylpropyltrimethoxysilane, γ-mercaptopropylmethyldimethoxysilane and 3-(heptafluoroisopropoxy)propyltriethoxysilane, γ-mercaptopropylmethyldimethoxysilane and heptadecafluoro-1,1,2,2-tetrahydrodecyltriethoxysilane, γ-mercaptopropylmethyldimethoxysilane and triethoxy-2-thienylsilane, and γ-mercaptopropylmethyldimethoxysilane and 3-(triethoxysilyl)furan.

(19) γ-aminopropylmethyldiethoxysilane and methyltrimethoxysilane, γ-aminopropylmethyldiethoxysilane and methyltriethoxysilane, γ-aminopropylmethyldiethoxysilane and ethyltrimethoxysilane, γ-aminopropylmethyldiethoxysilane and ethyltriethoxysilane, γ-aminopropylmethyldiethoxysilane and propyltrimethoxysilane, γ-aminopropylmethyldiethoxysilane and propyltriethoxysilane, γ-aminopropylmethyldiethoxysilane and butyltrimethoxysilane, γ-aminopropylmethyldiethoxysilane and butyltriethoxysilane, γ-aminopropylmethyldiethoxysilane and pentyltrimethoxysilane, γ-aminopropylmethyldiethoxysilane and pentyltriethoxysilane, γ-aminopropylmethyldiethoxysilane and heptyltrimethoxysilane, γ-aminopropylmethyldiethoxysilane and heptyltriethoxysilane, γ-aminopropylmethyldiethoxysilane and octyltrimethoxysilane, γ-aminopropylmethyldiethoxysilane and octyltriethoxysilane, γ-aminopropylmethyldiethoxysilane and dodecyltrimethoxysilane, γ-aminopropylmethyldiethoxysilane and dodecyltriethoxysilane, γ-aminopropylmethyldiethoxysilane and hexadecyltrimethoxysilane, γ-aminopropylmethyldiethoxysilane and hexadecyltriethoxysilane, γ-aminopropylmethyldiethoxysilane and octadecyltrimethoxysilane, γ-aminopropylmethyldiethoxysilane and octadecyltriethoxysilane, γ-aminopropylmethyldiethoxysilane and phenyltrimethoxysilane, γ-aminopropylmethyldiethoxysilane and phenyltriethoxysilane, γ-aminopropylmethyldiethoxysilane and vinyltrimethoxysilane, γ-aminopropylmethyldiethoxysilane and vinyltriethoxysilane, γ-aminopropylmethyldiethoxysilane and γ-aminopropyltrimethoxysilane, γ-aminopropylmethyldiethoxysilane and γ-aminopropyltriethoxysilane, γ-aminopropylmethyldiethoxysilane and γ-glycidoxypropyltrimethoxysilane, γ-aminopropylmethyldiethoxysilane and γ-glycidoxypropyltriethoxysilane, γ-aminopropylmethyldiethoxysilane and γ-methacryloxypropyltrimethoxysilane, γ-aminopropylmethyldiethoxysilane and γ-methacryloxypropyltriethoxysilane, γ-aminopropylmethyldiethoxysilane and triethoxy(4-(trifluoromethyl)phenyl)silane, γ-aminopropylmethyldiethoxysilane and dodecyltriethoxysilane, γ-aminopropylmethyldiethoxysilane and 3,3,3-trifluoropropyltrimethoxysilane, γ-aminopropylmethyldiethoxysilane and (triethoxysilyl)cyclohexane, γ-aminopropylmethyldiethoxysilane and perfluorooctylethyltriethoxysilane, γ-aminopropylmethyldiethoxysilane and triethoxyfluorosilane, γ-aminopropylmethyldiethoxysilane and tridecafluoro-1,1,2,2-tetrahydrooctyltriethoxysilane, γ-aminopropylmethyldiethoxysilane and pentafluorophenylpropyltrimethoxysilane, γ-aminopropylmethyldiethoxysilane and 3-(heptafluoroisopropoxy)propyltriethoxysilane, γ-aminopropylmethyldiethoxysilane and heptadecafluoro-1,1,2,2-tetrahydrodecyltriethoxysilane, γ-aminopropylmethyldiethoxysilane and triethoxy-2-thienylsilane, and γ-aminopropylmethyldiethoxysilane and 3-(triethoxysilyl)furan.

(20) N-(2-aminoethyl)aminopropylmethyldimethoxysilane and methyltrimethoxysilane, N-(2-aminoethyl)aminopropylmethyldimethoxysilane and methyltriethoxysilane, N-(2-aminoethyl)aminopropylmethyldimethoxysilane and ethyltrimethoxysilane, N-(2-aminoethyl)aminopropylmethyldimethoxysilane and ethyltriethoxysilane, N-(2-aminoethyl)aminopropylmethyldimethoxysilane and propyltrimethoxysilane, N-(2-aminoethyl)aminopropylmethyldimethoxysilane and propyltriethoxysilane, N-(2-aminoethyl)aminopropylmethyldimethoxysilane and butyltrimethoxysilane, N-(2-aminoethyl)aminopropylmethyldimethoxysilane and butyltriethoxysilane, N-(2-aminoethyl)aminopropylmethyldimethoxysilane and pentyltrimethoxysilane, N-(2-aminoethyl)aminopropylmethyldimethoxysilane and pentyltriethoxysilane, N-(2-aminoethyl)aminopropylmethyldimethoxysilane and heptyltrimethoxysilane, N-(2-aminoethyl)aminopropylmethyldimethoxysilane and heptyltriethoxysilane, N-(2-aminoethyl)aminopropylmethyldimethoxysilane and octyltrimethoxysilane, N-(2-aminoethyl)aminopropylmethyldimethoxysilane and octyltriethoxysilane, N-(2-aminoethyl)aminopropylmethyldimethoxysilane and dodecyltrimethoxysilane, N-(2-aminoethyl)aminopropylmethyldimethoxysilane and dodecyltriethoxysilane, N-(2-aminoethyl)aminopropylmethyldimethoxysilane and hexadecyltrimethoxysilane, N-(2-aminoethyl)aminopropylmethyldimethoxysilane and hexadecyltriethoxysilane, N-(2-aminoethyl)aminopropylmethyldimethoxysilane and octadecyltrimethoxysilane, N-(2-aminoethyl)aminopropylmethyldimethoxysilane and octadecyltriethoxysilane, N-(2-aminoethyl)aminopropylmethyldimethoxysilane and phenyltrimethoxysilane, N-(2-aminoethyl)aminopropylmethyldimethoxysilane and phenyltriethoxysilane, N-(2-aminoethyl)aminopropylmethyldimethoxysilane and vinyltrimethoxysilane, N-(2-aminoethyl)aminopropylmethyldimethoxysilane and vinyltriethoxysilane, N-(2-aminoethyl)aminopropylmethyldimethoxysilane and γ-aminopropyltrimethoxysilane, N-(2-aminoethyl)aminopropylmethyldimethoxysilane and γ-aminopropyltriethoxysilane, N-(2-aminoethyl)aminopropylmethyldimethoxysilane and γ-glycidoxypropyltrimethoxysilane, N-(2-aminoethyl)aminopropyltrimethoxyldimethoxysilane and γ-glycidoxypropyltriethoxysilane, N-(2-aminoethyl)aminopropylmethyldimethoxysilane and γ-methacryloxypropyltrimethoxysilane, N-(2-aminoethyl)aminopropylmethyldimethoxysilane and γ-methacryloxypropyltriethoxysilane, N-(2-aminoethyl)aminopropylmethyldimethoxysilane and triethoxy(4-(trifluoromethyl)phenyl)silane, N-(2-aminoethyl)aminopropylmethyldimethoxysilane and dodecyltriethoxysilane, N-(2-aminoethyl)aminopropylmethyldimethoxysilane and 3,3,3-trifluoropropyltrimethoxysilane, N-(2-aminoethyl)aminopropylmethyldimethoxysilane and (triethoxysilyl)cyclohexane, N-(2-aminoethyl)aminopropylmethyldimethoxysilane and perfluorooctylethyltriethoxysilane, N-(2-aminoethyl)aminopropylmethyldimethoxysilane and triethoxyfluorosilane, N-(2-aminoethyl)aminopropylmethyldimethoxysilane and tridecafluoro-1,1,2,2-tetrahydrooctyltriethoxysilane, N-(2-aminoethyl)aminopropylmethyldimethoxysilane and pentafluorophenylpropyltrimethoxysilane, N-(2-aminoethyl)aminopropylmethyldimethoxysilane and 3-(heptafluoroisopropoxy)propyltriethoxysilane, N-(2-aminoethyl)aminopropylmethyldimethoxysilane and heptadecafluoro- 1,1,2,2-tetrahydrodecyltriethoxysilane, N-(2-aminoethyl)aminopropylmethyldimethoxysilane and triethoxy-2-thienylsilane, and N-(2-aminoethyl)aminopropylmethyldimethoxysilane and 3-(triethoxysilyl)furan.

(21) 3,3,3-trifluoropropylmethyldimethoxysilane and methyltrimethoxysilane, 3,3,3-trifluoropropylmethyldimethoxysilane and methyltriethoxysilane, 3,3,3-trifluoropropylmethyldimethoxysilane and ethyltrimethoxysilane, 3,3,3-trifluoropropylmethyldimethoxysilane and ethyltriethoxysilane, 3,3,3-trifluoropropylmethyldimethoxysilane and propyltrimethoxysilane, 3,3,3-trifluoropropylmethyldimethoxysilane and propyltriethoxysilane, 3,3,3-trifluoropropylmethyldimethoxysilane and butyltrimethoxysilane, 3,3,3-trifluoropropylmethyldimethoxysilane and butyltriethoxysilane, 3,3,3-trifluoropropylmethyldimethoxysilane and pentyltrimethoxysilane, 3,3,3-trifluoropropylmethyldimethoxysilane and pentyltriethoxysilane, 3,3,3-trifluoropropylmethyldimethoxysilane and heptyltrimethoxysilane, 3,3,3-trifluoropropylmethyldimethoxysilane and heptyltriethoxysilane, 3,3,3-trifluoropropylmethyldimethoxysilane and octyltrimethoxysilane, 3,3,3-trifluoropropylmethyldimethoxysilane and octyltriethoxysilane, 3,3,3-trifluoropropylmethyldimethoxysilane and dodecyltrimethoxysilane, 3,3,3-trifluoropropylmethyldimethoxysilane and dodecyltriethoxysilane, 3,3,3-trifluoropropylmethyldimethoxysilane and hexadecyltrimethoxysilane, 3,3,3-trifluoropropylmethyldimethoxysilane and hexadecyltriethoxysilane, 3,3,3-trifluoropropylmethyldimethoxysilane and octadecyltrimethoxysilane, 3,3,3-trifluoropropylmethyldimethoxysilane and octadecyltriethoxysilane, 3,3,3-trifluoropropylmethyldimethoxysilane and phenyltrimethoxysilane, 3,3,3-trifluoropropylmethyldimethoxysilane and phenyltriethoxysilane, 3,3,3-trifluoropropylmethyldimethoxysilane and vinyltrimethoxysilane, 3,3,3-trifluoropropylmethyldimethoxysilane and vinyltriethoxysilane, 3,3,3-trifluoropropylmethyldimethoxysilane and γ-aminopropyltrimethoxysilane, 3,3,3-trifluoropropylmethyldimethoxysilane and γ-aminopropyltriethoxysilane, 3,3,3-trifluoropropylmethyldimethoxysilane and γ-glycidoxypropyltrimethoxysilane, 3,3,3-trifluoropropylmethyldimethoxysilane and γ-glycidoxypropyltriethoxysilane, 3,3,3-trifluoropropylmethyldimethoxysilane and γ-methacryloxypropyltrimethoxysilane, 3,3,3-trifluoropropylmethyldimethoxysilane and γ-methacryloxypropyltriethoxysilane, 3,3,3-trifluoropropylmethyldimethoxysilane and triethoxy(4-(trifluoromethyl)phenyl)silane, 3,3,3-trifluoropropylmethyldimethoxysilane and dodecyltriethoxysilane, 3,3,3-trifluoropropylmethyldimethoxysilane and 3,3,3-trifluoropropyltrimethoxysilane, 3,3,3-trifluoropropylmethyldimethoxysilane and (triethoxysilyl)cyclohexane, 3,3,3-trifluoropropylmethyldimethoxysilane and perfluorooctylethyltriethoxysilane, 3,3,3-trifluoropropylmethyldimethoxysilane and triethoxyfluorosilane, 3,3,3-trifluoropropylmethyldimethoxysilane and tridecafluoro-1,1,2,2-tetrahydrooctyltriethoxysilane, 3,3,3-trifluoropropylmethyldimethoxysilane and pentafluorophenylpropyltrimethoxysilane, 3,3,3-trifluoropropylmethyldimethoxysilane and 3-(heptafluoroisopropoxy)propyltriethoxysilane, 3,3,3-trifluoropropylmethyldimethoxysilane and heptadecafluoro-1,1,2,2-tetrahydrodecyltriethoxysilane, 3,3,3-trifluoropropylmethyldimethoxysilane and triethoxy-2-thienylsilane, and 3,3,3-trifluoropropylmethyldimethoxysilane and 3-(triethoxysilyl)furan.

Preferred combinations of at least one dialkoxysilane compound and at least one tetraalkoxysilane compound are listed below.

(1) Tetramethylsilane and methylhydrogendimethoxysilane, tetramethylsilane and methylhydrogendiethoxysilane, tetramethylsilane and dimethyldimethoxysilane, tetramethylsilane and dimethyldiethoxysilane, tetramethylsilane and methylethyldimethoxysilane, tetramethylsilane and diethyldimethoxysilan, tetramethylsilane and diethyldiethoxysilan, tetramethylsilane and methylpropyldimethoxysilane, tetramethylsilane and methylpropyldiethoxysilane, tetramethylsilane and diisopropyldimethoxysilane, tetramethylsilane and phenylmethyldimethoxysilane, tetramethylsilane and vinylmethyldimethoxysilane, tetramethylsilane and γ-glycidoxypropylmethyldimethoxysilane, tetramethylsilane and γ-glycidoxypropylmethyldiethoxysilane, tetramethylsilane and β-(3,4-epoxycyclohexyl)ethylmethyldimethoxysilane, tetramethylsilane and γ-methacryloxypropylmethyldimethoxysilane, tetramethylsilane and γ-methacryloxypropylmethyldiethoxysilane, tetramethylsilane and γ-mercaptopropylmethyldimethoxysilane, tetramethylsilane and γ-aminopropylmethyldiethoxysilan, tetramethylsilane and N-(2-aminoethyl)aminopropylmethyldimethoxysilane, and tetramethylsilane and 3,3,3-trifluoropropylmethyldimethoxysilane.

(2) Tetraethylsilane and methylhydrogendimethoxysilane, tetraethylsilane and methylhydrogendiethoxysilane, tetraethylsilane and dimethyldimethoxysilane, tetraethylsilane and dimethyldiethoxysilane, tetraethylsilane and methylethyldimethoxysilane, tetraethylsilane and diethyldimethoxysilan, tetraethylsilane and diethyldiethoxysilan, tetraethylsilane and methylpropyldimethoxysilane, tetraethylsilane and methylpropyldiethoxysilane, tetraethylsilane and diisopropyldimethoxysilane, tetraethylsilane and phenylmethyldimethoxysilane, tetraethylsilane and vinylmethyldimethoxysilane, tetraethylsilane and γ-glycidoxypropylmethyldimethoxysilane, tetraethylsilane and γ-glycidoxypropylmethyldiethoxysilane, tetraethylsilane and β-(3,4-epoxycyclohexyl)ethylmethyldimethoxysilane, tetraethylsilane and γ-methacryloxypropylmethyldimethoxysilane, tetraethylsilane and γ-methacryloxypropylmethyldiethoxysilane, tetraethylsilane and γ-mercaptopropylmethyldimethoxysilane, tetraethylsilane and γ-aminopropylmethyldimethoxysilan, tetraethylsilane and N-(2-aminoethyl)aminopropylmethyldimethoxysilane, and 3,3,3-trifluoropropylmethyldimethoxysilane.

(3) Tetrapropoxysilane and methylhydrogendimethoxysilane, tetrapropoxysilane and methylhydrogendiethoxysilane, tetrapropoxysilane and dimethyldimethoxysilane, tetrapropoxysilane and dimethyldiethoxysilane, tetrapropoxysilane and methylethyldimethoxysilane, tetrapropoxysilane and diethyldimethoxysilan, tetrapropoxysilane and diethyldiethoxysilan, tetrapropoxysilane and methylpropyldimethoxysilane, tetrapropoxysilane and methylpropyldiethoxysilane, tetrapropoxysilane and diisopropyldimethoxysilane, tetrapropoxysilane and phenylmethyldimethoxysilane, tetrapropoxysilane and vinylmethyldimethoxysilane, tetrapropoxysilane and γ-glycidoxypropylmethyldimethoxysilane, tetrapropoxysilane and γ-glycidoxypropylmethyldiethoxysilane, tetrapropoxysilane and β-(3,4-epoxycyclohexyl)ethylmethyldimethoxysilane, tetrapropoxysilane and γ-methacryloxypropylmethyldimethoxysilane, tetrapropoxysilane and γ-methacryloxypropylmethyldiethoxysilane, tetrapropoxysilane and γ-mercaptopropylmethyldimethoxysilane, tetrapropoxysilane and γ-aminopropylmethyldimethoxysilan, tetrapropoxysilane and N-(2-aminoethyl)aminopropylmethyldimethoxysilane, and tetrapropoxysilane and 3,3,3-trifluoropropylmethyldimethoxysilane.

Examples of the organic solvent used for the charge transport varnish include the following.

N,N-dimethylformamide (153° C.), N,N-dimethylacetamide (165° C.), N-methylpyrrolidone (202° C.), 1,3-dimethyl-2-imidazolidinone (225° C.), dimethylsulfoxide (189° C.), N-cyclohexyl-2-pyrrolidinone (284° C.), aromatic hydrocarbons [such as benzene (80° C.), toluene (111° C.), ethylbenzene (136° C.), p-xylene (138° C.), o-xylene (138° C.), and styrene (145° C.)], ketones [such as acetone (56° C.), methyl ethyl ketone (80° C.), methyl isopropyl ketone (94° C.), diethyl ketone (102° C.), methyl isobutyl ketone (117° C.), methyl normal butyl ketone (127° C.), cyclohexanone (155° C.), and ethyl normal amyl ketone (167° C.)], esters [such as ethyl acetate (77° C.), isopropyl acetate ketone (85° C.), normal propyl acetate (101° C.), isobutyl acetate (116° C.), normal butyl acetate (125° C.), normal amyl acetate (142° C.), methyl caproate (151° C.), 2-methylpentyl acetate (162° C.), and normal butyl lactate (186° C.)], glycol esters and glycol ethers [such as ethylene glycol dimethyl ether (85° C.), propylene glycol monomethyl ether (119° C.), ethylene glycol monomethyl ether (124° C.), propylene glycol monoethyl ether (132° C.), ethylene glycol monoethyl ether (136° C.), ethylene glycol monoisopropyl ether (144° C.), ethylene glycol methyl ether acetate (145° C.), propylene glycol monomethyl ether acetate (146° C.), ethylene glycol ethyl ether acetate (156° C.), diethylene glycol dimethyl ether (162° C.), propylene glycol monobutyl ether (170° C.), ethylene glycol monobutyl ether (171° C.), diethylene glycol diethyl ether (188° C.), dipropylene glycol monomethyl ether (189° C.), diethylene glycol monomethyl ether (194° C.), dipropylene glycol monoethyl ether (198° C.), diethylene glycol monoethyl ether (202° C.), triethylene glycol dimethyl ether (216° C.), diethylene glycol monoethyl ether acetate (217° C.), and diethylene glycol (244° C.)], alcohols [such as methanol (65° C.), ethanol (78° C.), isopropanol (82° C.), tert-butanol (83° C.), allyl alcohol (97° C.), normal propanol (97° C.), 2-methyl-2-butanol (102° C.), isobutanol (108° C.), normal butanol (117° C.), 2-methyl-1-butanol (130° C.), 1-pentanol (137° C.), 2-methyl-1-pentanol (148° C.), 2-ethyl hexanol (185° C.), 1-octanol (196° C.), ethylene glycol (197° C.), hexylene glycol (198° C.), trimethylene glycol (214° C.), 1-methoxy-2-butanol (135° C.), cyclohexanol (161° C.), diacetone alcohol (166° C.), furfryl alcohl (170° C.), tetrahydrofurfryl alcohol (178° C.), propylene glycol (187° C.), benzyl alcohol (205° C.), and 1,3-butanediol (208° C.)], phenols [such as anisole (154° C.), phenol (182° C.), and m-cresol (202° C.)], and ethers and carboxylic acids [such as isopropyl ether (68° C.), 1,4-dioxane (101° C.), acetic acid (117° C.), and γ-butyl lactone (204° C.)].

These organic solvents may be used alone or in combination with one another.

According to the present invention, it is possible to use a high-solvency solvent that readily dissolves the charge transport substance and charge accepting substance. Examples of such high-solvency solvents include water; methanol, N,N-dimethylformamide, N,N-dimethylacetamide, N-methylpyrrolidone, 1,3-dimethyl-2-imidazolidinone, dimethylsulfoxide, chloroform, and toluene. These solvents may be used alone or in combination with one another. The amount of these solvents may be 5 to 100 wt % for the amount of all the solvents used for the varnish.

Incidentally, the charge transport vanish should preferably be completely dissolved or uniformly dispersed in the foregoing solvents.

Also, the charge transport varnish of the present invention should preferably contain at least one species of high-viscosity organic solvents having a viscosity of 10 to 200 mPa·s, particularly 50 to 150 mPa·s, at 20° C. and a boiling point of 50 to 300° C., particularly 150 to 250° C., at normal pressure.

The high-viscosity organic solvents include, for example, cyclohexanol, ethylene glycol, ethylene glycol diglycidyl ether, 1,3-octylene glycol, diethylene glycol, dipropylene glycol, triethylene glycol, tripropylene glycol, 1,3-butanediol, 2,3-butanediol, 1,4-butaneidol, propylene glycol, and hexylene glycol.

The additive ratio of the high-viscosity organic solvent to all the solvents used for the varnish of the present invention should be in such a range that no solids separate out. Preferred additive ratios are 5 to 80 wt % so long as no solids separate out.

Moreover, additional solvents capable of imparting flatness to the film at the time of baking may be added in a ratio of 1 to 90 wt %, preferably 1 to 50 wt %, for all the solvents used for the varnish, in order to improve the ability to wet substrates and control the surface tension, polarity, and boiling point of the solvent.

Examples of such solvents include butyl cellosolve, diethylene glycol diethyl ether, dipropylene glycol monomethyl ether, ethylcarbitol, diacetone alcohol, γ-butyrolactone, and ethyl lactate.

The amount of solids in the charge transfer varnish should preferably be 0.001 to 50 wt %, more preferably 0.01 to 20 wt %, in consideration of the workability of the varnish at the time of application.

In the case where the charge transport varnish of the present invention contains the above-mentioned silane compounds, the stability of the varnish may improve if the silane compounds are present in the form of oligomer or polymer than silane monomer. Therefore, the charge transport varnish of the present invention may contain water that hydrolyzes and condenses the silane compounds.

In this case, the amount of water to be used should preferably be 0.0001 to 10 wt %, more preferably 0.001 to 5 wt %, for the total amount of all the organic solvents in the varnish.

The charge transport varnish mentioned above is made into a charge transport thin film on a substrate as it is applied to a substrate and its solvent is evaporated.

The method for varnish application is not specifically restricted, and it includes dipping, spin coating, transfer printing, roll coating, brushing, ink jet, and spraying.

Solvent evaporation may be accomplished in any manner by, for example, heating with a hot plate or oven in an adequate atmosphere of air or inert gas like nitrogen, or in a vacuum. In this way a thin film with a uniform surface can be obtained.

The baking temperature is not specifically restricted so long as it is high enough to evaporate the solvents; it should preferably be 40 to 250° C. Baking may be accomplished in two or more stages at different temperatures so as to form the thin film more uniformly or cause reactions to take place on the substrate.

The charge transport thin film is not specifically restricted in thickness. If it is used as the charge injection layer in the organic EL device, its preferred thickness is 5 to 200 nm. The thickness may be changed by adjusting the concentration of solids in the varnish or the amount of the solution on the substrate at the time of application.

For production of OLED devices, the charge transport varnish of the present invention is used in conjunction with various materials by various methods as shown below without restrictions.

The electrode substrate to be used should preferably be cleaned beforehand by washing with a liquid such as detergent, alcohol, and pure water. The anode substrate should preferably undergo surface treatment with ozone or oxygen in plasma state immediately before its use. This surface treatment may be omitted if the anode material is composed mainly of organic materials.

The following method may be employed to use the hole transport varnish for the OLED device.

The hole transport varnish is applied to the anode substrate. This step is followed by solvent evaporation and baking in the way mentioned above. Thus there is formed the hole transport thin film on the electrode. The electrode is placed in a vacuum evaporation apparatus for sequential deposition thereon with a hole transport layer, light-emitting layer, electron transport layer, electron injection layer, and cathode metal layer. In this way there is obtained the OLED device as desired. A carrier block layer may optionally be interposed between any layers to control the light-emitting region.

The anode material may be formed from a transparent electrode material such as indium tin oxide (ITO) and indium zinc oxide (IZO). It should preferably be planarized. It is also possible to use a polythiophene derivative or polyaniline derivative highly capable of charge transport.

The hole transport layer may be formed from any of the following materials. Triarylamines, such as (triphenylamine) dimer derivative (TPD), ($\alpha$-naphthyldiphenylamine)dimer ($\alpha$-NPD), and [(triphenylamine)dimer]spirodimer (Spiro-TAD); star-burst amines, such as 4,4',4"-tris(3-methylphenyl (phenyl)amino)triphenylamine (m-MTDATA), 4,4',4"-tris[1-naphthyl(phenyl)amino]triphenylamine (1-TNATA), and oligothiophenes, such as 5,5"-bis-{4-[bis(4-methylphenyl) amino]phenyl}-2,2':5',2"-terthiophene (BMA-3T).

The light-emitting layer may be formed from any of tris(8-quinolinolate)aluminum (III) ($Alq_3$), bis(8-quinolinolate) zinc (II) ($Znq_2$), bis(2-methyl-8-quinolinolate)(p-phenylphenolate)aluminum (III) (BAlq), and 4,4'-bis(2,2-diphenylvinyl)biphenyl (DPVBi). The light-emitting layer may be formed by vapor deposition of an electron or hole transport material together with a light-emitting dopant.

The electron transport material includes $Alq_a$, BAlq, DPVBi, (2-(4-biphenyl)-5-(4-t-butylphenyl)-1,3,4-oxadiazole) (PBD), triazole derivatives (TAZ), bathocuproin (BCP), and silole derivatives.

The light-emitting dopant includes quinacridone, ruburene, coumarin 540, 4-(dicyanomethylene)-2-methyl-6-(p-dimethylaminostylyl)-4H-pyran (DCM), tris(2-phenylpyridine)iridium (III) ($Ir(ppy)_3$), (1,10-phenanthroline)-tris(4,4, 4-trifluoro-1-(2-thienyl)-butane-1,3-dionate)europium (III) ($Eu(TTA)_3phen$), and the like.

The carrier block layer may be formed from any of PBD, TAZ, BCP, and the like.

The electron injection layer may be formed from any of lithium oxide ($Li_2O$), magnesium oxide (MgO), alumina ($Al_2O_3$), lithium fluoride (LiF), magnesium fluoride ($MgF_2$), strontium fluoride ($SrF_2$), Liq, Li(acac), lithium acetate, lithium benzoate, and the like.

The cathode may be formed from any of aluminum, magnesium-silver alloy, aluminum-lithium alloy, lithium, sodium, potassium, cesium, and the like.

For production of OLED devices, the electron transport varnish is used by various methods as shown below.

The electron transport varnish is applied to the cathode substrate, so that the electron transport thin film is formed. This is placed in a vacuum deposition apparatus, and vapor deposition is performed to form the electron transport layer, light-emitting layer, hole transport layer, and hole injection layer from the same materials as mentioned above. Then sputtering is performed for the anode material to complete the OLED device.

For production of the PLED device, the charge transport varnish of the present invention is used by the following method, which is not limitative.

The OLED device containing the charge transport thin film, which is formed from the charge transport varnish of the present invention, can be produced by forming the light-emitting charge transport polymer layer instead of performing vacuum deposition to form the hole transport layer, light-emitting layer, electron transport layer, and electron injection layer in production of the OLED device mentioned above.

To be specific, the PLED device is produced by coating the anode substrate with the charge transport varnish (hole transport varnish), thereby forming the hole transport thin film as mentioned above, and covering it with the light-emitting charge transport polymer layer and forming the cathode electrode by vapor deposition.

Alternatively, the PLED device is produced by coating the cathode substrate with the charge transport varnish (electron transport varnish), thereby forming the electron transport thin film as mentioned above, and covering it with the light-emitting charge transport polymer layer and forming the anode electrode by sputtering, vapor deposition, spin coating, or the like.

The cathode and anode can be formed from the same material as used for the OLED device mentioned above. They undergo cleaning and surface treatment in the same way as mentioned above.

The light-emitting charge transport polymer layer may be formed by dissolving or uniformly dispersing the light-emitting charge transport polymer material (alone or together with a light-emitting dopant) in a solvent, applying the resulting solution or dispersion onto the electrode substrate on which the hole injection layer has been formed, and finally evaporating the solvent.

The light-emitting charge transport polymer material includes, for example, polyfluorene derivatives such as poly (9,9-dialkylfluorene) (PDAF), polyphenylenevinylene derivatives such as poly(2-methoxy-5-(2'-ethylhexoxy)-1,4-phenylenevinylene) (MEH-PPV), polythiophene derivatives such as poly(3-alkylthiophene) (PAT), and polyvinylcarbazole (PVCz).

The solvent includes toluene, xylene, chloroform, and the like. Dissolution or uniform dispersion may be accomplished by stirring with or without heating or by ultrasonic dispersion.

The method for application is not specifically restricted; it includes ink jet, spraying, dipping, spin coating, transfer printing, roll coating, and brushing. Application should preferably be carried out under an inert gas such as nitrogen and argon.

Solvent evaporation may be accomplished by heating with an oven or hot plate under an inert gas or in a vacuum.

EXAMPLES

The present invention will be described in more detail with reference to the following Examples and Comparative Examples, which are not intended to restrict the scope thereof. The following apparatus were used in the Examples.

[MS Spectrum]
Apparatus (MALDI-TOF): made by Applied Biosystems Inc., Voyager-DE™ PRO
[NMR Spectrum]
ECP300 made by Nippon Denshi Co., Ltd.

[1] Synthesis of Oligoaniline Compound

Comparative Example 1

Phenyltetraaniline (PTA for short hereinafter) represented below was synthesized from p-hydroxydiphenylamine and p-phenylenediamine according to the method disclosed in Bulletin of Chemical Society of Japan, 1994, vol. 67, pp. 1749-1752. (Pale bluish solids, Yields: 85%)

[Chemical Formula 9]

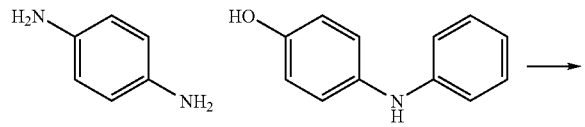

The thus obtained PTA in an amount of 20 g (0.0452 mmol) was placed in a 1 L three-neck round-bottom flask under a nitrogen atmosphere, together with 2 g (10 wt % of PTA) of activated carbon and 500 g of dehydrated 1,4-dioxane which had been ultrasonically deaerated. Next, the content of the flask was stirred at 90° C. with constant heating in an oil bath for one hour, so that the PTA was completely dissolved. To remove the activated carbon, the resulting solution underwent hot filtration through Kiriyama Glass S-60 kept at 90° C. by a water circulator equipped with a temperature controller. The filer medium is Kiriyama filter paper 3C and Celite 545 as stationary phase. The resulting filtrate was allowed to stand for cooling down to 20° C. There was obtained a pale violet solution containing PTA precipitates. The reaction vessel holding the solution was placed in a glove box. Nitrogen was passed through the glove box until the relative humidity therein decreased to 5%. PTA was filtered off by suction in the glove box, with the relative humidity therein kept at 5%. The PTA on the Büchner funnel was washed sequentially with 200 mL of 1,4-dioxane, 200 mL of dehydrated toluene, and 200 mL of diethyl ether. The PTA was transferred to a 100-mL round-bottom flask by using a microspatula of fluorocarbon resin in the glove box. The flask was evacuated through a three-way stopcock and then supplied with nitrogen for air purging. The PTA was dried under reduced pressure for 24 hours in a vacuum drier kept at 120° C. Thus there was obtained 19.34 g of PTA in the form of white solids (Yields: 96%).

Incidentally, the dehydrated 1,4-dioxane is a product of Kanto Chemical Co., Inc., the hydrazine monohydrate is a product of Wako Pure Chemical Industries, Ltd., the activated carbon is a product of Junsei Chemical Co., Ltd., and the Celite 545 is a product of Junsei Chemical Co., Ltd.

1H-NMR; δ 6.6-7.2 (Ar, 22H, m), 7.6-7.8 (—NH, 4H) ppm
Molecular weight; 442.55
MALDI-TOF; 442.43[M]$^+$ Example 1

[1-1] Synthesis of Dibromophenyltetraaniline

[Chemical Formula 10]

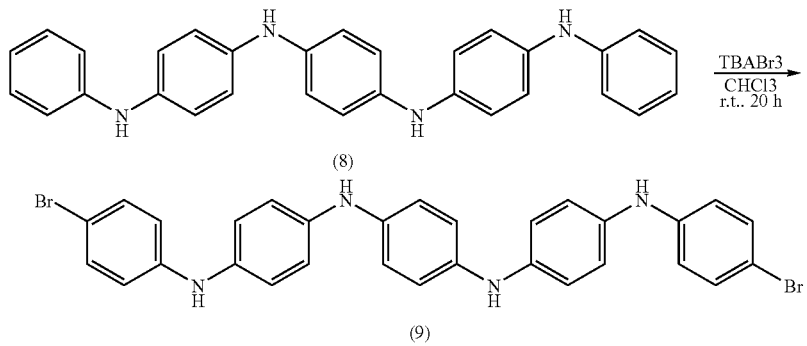

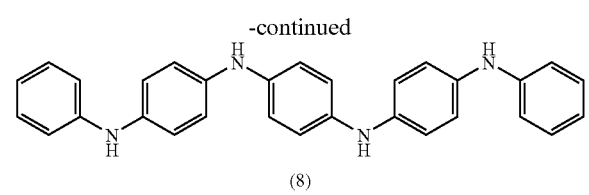

In a 500-mL Erlenmeyer flask were placed 20 g (41.19 mmol) of PTA and 300 mL of chloroform. The content was stirred by means of an ellipsoidal stirring chip. (PTA did not dissolve in chloroform but remained suspending.) In a 200-mL beaker was placed 39.72 g (82.38 mmol) of tetrabutylammonium tribromide (TBABr$_3$), which was dissolved in 50 mL of chloroform added later. The resulting solution was added dropwise to the chloroform-PTA solution, and the mixture was stirred for 20 hours at room temperature in the air. Then, the chloroform-PTA solution was transferred to a 1000-mL separatory funnel and washed five times with 100 mL of saturated aqueous solution of sodium thiosulfate. After separation, the chloroform layer was transferred to a 500-mL Erlenmeyer flask and then dehydrated with 20 g of anhydrous magnesium sulfate. With the anhydrous magnesium sulfate removed by filtration, the chloroform solution was transferred to a 500-mL eggplant-shaped flask and freed of chloroform by means of an evaporator. The resulting crude product was purified by treatment with activated carbon and recrystallization according to the method employed in Comparative Example 1 (Yields: 85%).

1H-NMR; δ 6.8-7.2 (Ar, 20H, m), 7.6-7.8 (—NH, 4H) ppm

[1-2] Introduction of BOC

[Chemical Formula 11]

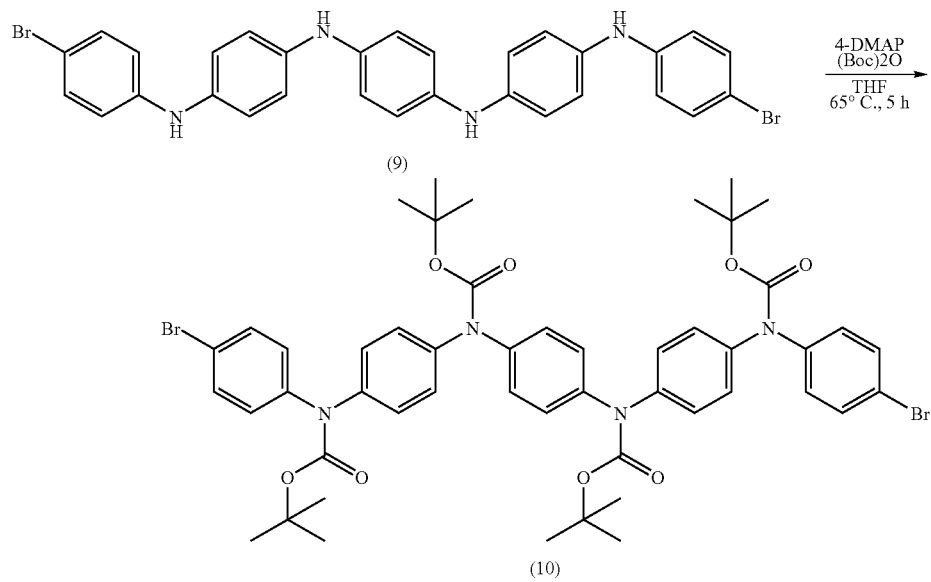

In a 500-mL eggplant-shaped flask were placed 10 g (16.65 mmol) of the compound (9) obtained by the step [1-1], 0.2 g (1.66 mmol) of 4-dimethylaminopyridine, 15.26 g (69.95 mmol) of di-t-butyl dicarbonate, and 400 mL of tetrahydrofuran (THF). They underwent reaction at 65° C. for five hours. After reaction was complete, THF was removed by means of an evaporator. To the residue was added 400 mL of methanol. After stirring at room temperature for 20 minutes, precipitates were recovered by filtration through a Buchner funnel. After drying at 50° C. in a vacuum, there was obtained the desired product (Yields: 80%).

1H-NMR; δ 1.36 ($CH_3$, 36H, s), 7.1-7.6 (Ar, 20H, m) ppm

[1-3] Coupling Reaction

[Chemical Formula 12]

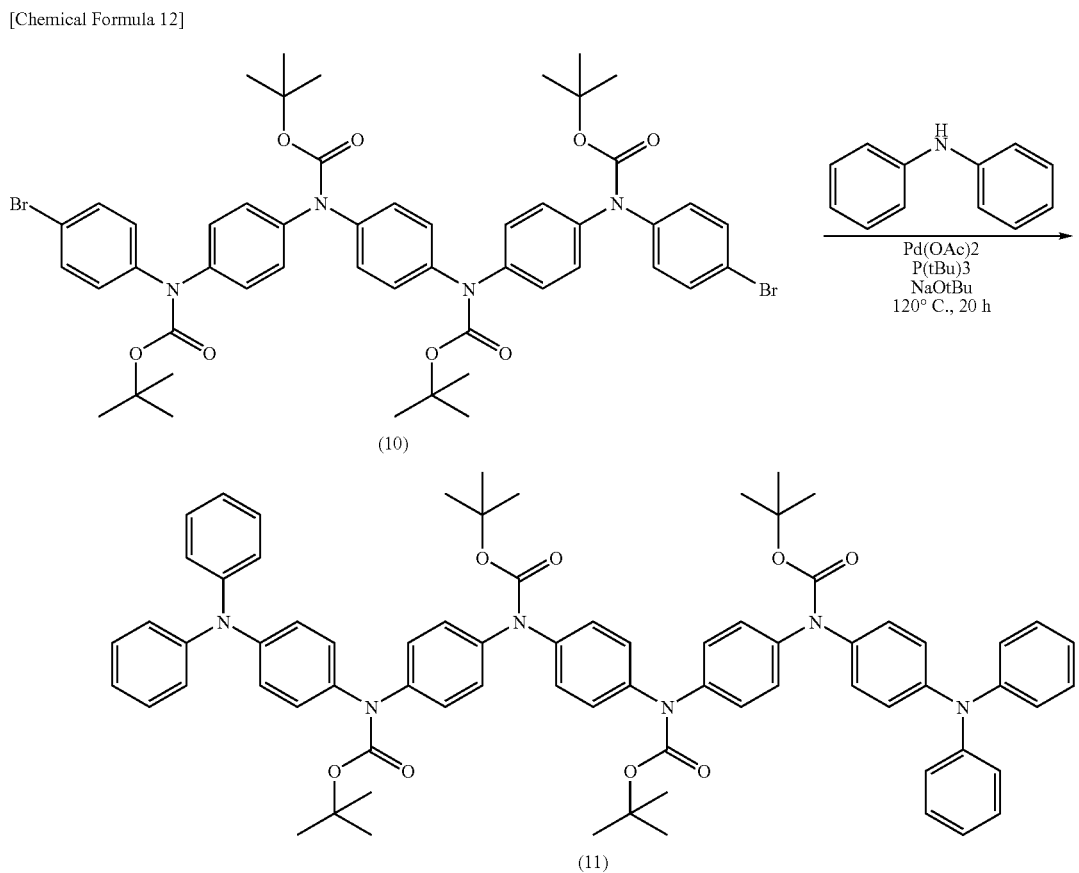

In a 300-mL three-neck flask were placed 200 mL of toluene, 67.2 mg (0.3 mmol) of palladium acetate, and an ellipsoidal stirring chip. The two outer necks were closed with septum caps and the center neck was provided with a reflux coiled condenser. To the top of the condenser was attached a three-way stopcock, to which is attached a balloon filled with nitrogen gas. The atmosphere in the flask was replaced three times by nitrogen gas supplied from the balloon with the help of a vacuum pump. Into the flask was injected 1.2 g (6 mmol) of tris-t-butylphosphine by means of a syringe, followed by stirring for 5-10 minutes at room temperature. The flask was further charged with 10 g (9.99 mmol) of the compound (10) obtained in the step [1-2], 3.38 g (20 mmol) of diphenylamine, and 2 g (20.98 mmol) of sodium t-butoxide. With the flask placed on an oil bath, the solution therein was gradually heated to 120° C. with stirring. After 20 hours, the flask was dismounted from the oil bath so as to terminate reaction, and the solution was allowed to cool to room temperature in an atmosphere of nitrogen.

The reaction solution was transferred to a separatory funnel and was given 70 mL of diethyl ether. It was washed several times with 100 mL of saturated aqueous solution of sodium chloride. The organic layer was separated and dried with anhydrous magnesium sulfate. With the anhydrous magnesium sulfate filtered out, the organic layer was freed of the solvent by means of an evaporator. Thus there was obtained a crude product in a yield of 75%. This crude product was used as such for the ensuing reactions because it involved difficulties in isolation and purification.

[1-4] Removal of BOC

[Chemical Formula 13]

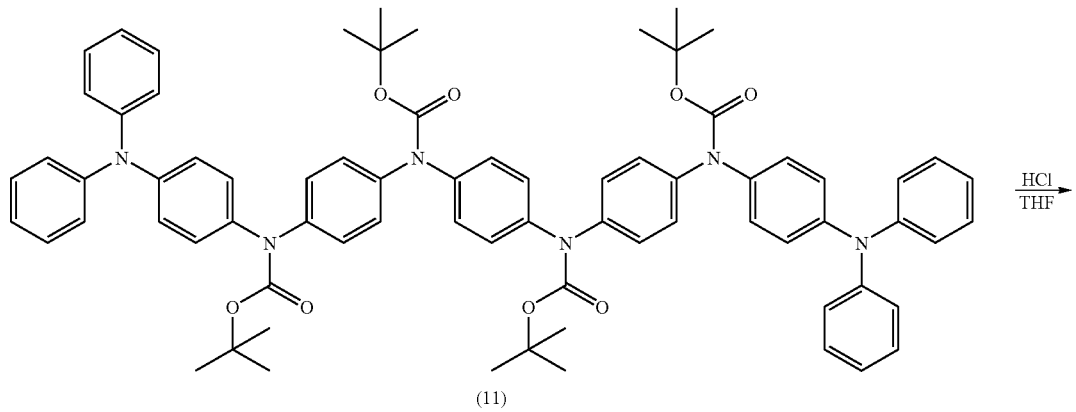

(11)

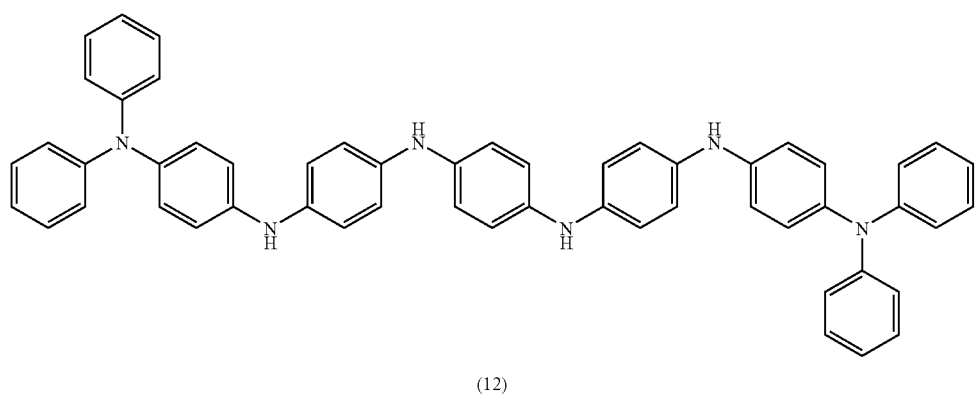

(12)

In a 500-mL eggplant-shaped flask were placed 10 g (8.49 mmol) of the compound (II) obtained in the step [1-3], 200 mL of tetrahydrofuran, 50 mL of aqueous solution of 4N hydrochloric acid, and an ellipsoidal stirring chip. With the flask equipped with a reflux coiled condenser, reaction was carried out at 65° C. for five hours in the air, and the reaction vessel was allowed to cool to terminate reaction. The reaction solution was transferred to a separatory funnel and washed therein several times with 50 mL of saturated aqueous solution of sodium hydroxide and further several times with water. The organic layer was dehydrated with anhydrous magnesium sulfate, which was discarded later by filtration. The filtrate was freed of solvent by means of an evaporator. Thus there was obtained a crude product in a yield of 70%. This crude product was treated with activated carbon and recrystallized according to the process used in Comparative Example 1 (Yields: 90%).

1H-NMR; δ 6.8-7.3 (Ar, 40H, m), 7.55-7.85 (—NH, 4H) ppm

Molecular weight; 776.97

MALDI-TOF; 775.87[M]$^+$

Example 2

[2-1] Synthesis of N,N-di-(4-biphenylyl)-benzylamine

[Chemical Formula 14]

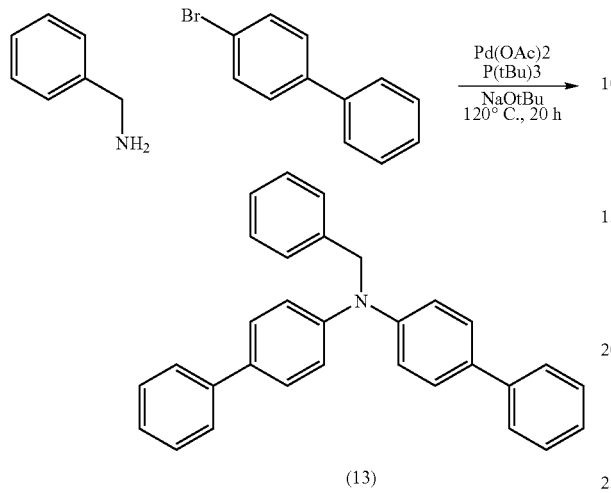

(13)

In a 100-mL three-neck flask were placed 80 mL of toluene, 42.0 mg (0.187 mmol) of palladium acetate, and an ellipsoidal stirring chip. The two outer necks were closed with septum caps and the center neck was provided with a reflux coiled condenser. To the top of the condenser was attached a three-way stopcock, to which is attached a balloon filled with nitrogen gas. The atmosphere in the flask was replaced three times by nitrogen gas supplied from the balloon with the help of a vacuum pump. Into the flask was injected 0.6 g (3 mmol) of tris-t-butylphosphine by means of a syringe, followed by stirring for five to ten minutes at room temperature. The flask was further charged with 2.04 mL (18.7 mmol) of benzylamine, 10.0 g (42.9 mmol) of 4-dibromophenyl, and 4.3 g (44.9 mmol) of sodium t-butoxide. With the flask placed on an oil bath, the solution therein was gradually heated to 120° C. with stirring. After 20 hours, the flask was dismounted from the oil bath so as to terminate reaction, and the solution was allowed to cool to room temperature in an atmosphere of nitrogen. The reaction solution was transferred to a separatory funnel and was given 10 mL of diethyl ether. It was washed several times with 50 mL of saturated aqueous solution of sodium chloride. The organic layer was separated and dried with anhydrous magnesium sulfate. With the anhydrous magnesium sulfate filtered out, the organic layer was freed of the solvent by means of an evaporator. Thus there was obtained a crude product, which was subsequently purified by washing several times with 50 mL of toluene (Yields: 90%).

1H-NMR; δ 5.07 ($CH_2$, 2H, s), 7.0-7.7 (Ar, 23H, m) ppm

[2-2] Removal of Benzyl

[Chemical Formula 15]

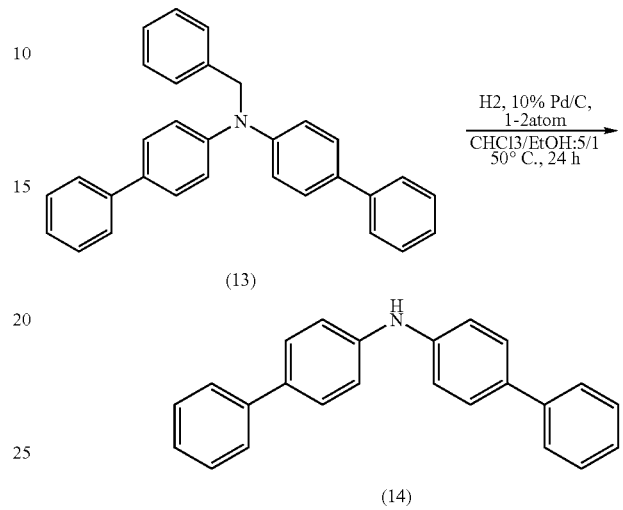

In a 300-mL eggplant-shaped flask were placed 1.35 g (3.28 mmol) of the compound (13) obtained by the step [2-1] and 135 mg (10 wt %) of palladium-activated carbon (containing 10 wt % of palladium). The flask was further charged with 100 mL of chloroform and 20 mL of ethanol to dissolve the compound (13). With an ellipsoidal stirring chip placed therein, the flask was provided with a three-way stopcock to which is attached a balloon filled with hydrogen gas. The atmosphere in the flask was replaced three times by hydrogen gas with the help of a vacuum pump. The balloon was replenished with hydrogen gas, and reaction was carried out at 50° C. for 24 hours. After reaction was complete, the reaction solution was given 100 mL of dichloromethane and the catalyst was filtered off. The resulting filtrate was transferred to a separatory funnel. After washing with 50 mL of saturated aqueous solution of sodium hydrogen carbonate, the organic layer was separated and dehydrated with anhydrous magnesium sulfate. After filtration, the filtrate was freed of solvent by means of an evaporator. The resulting crude product was purified by recrystallization from 50 mL of toluene (Yields: 90%).

1H-NMR; δ 5.83 (1H, s), 7.0-7.8 (18H, m) ppm

[2-3] Coupling Reaction

[Chemical Formula 16]

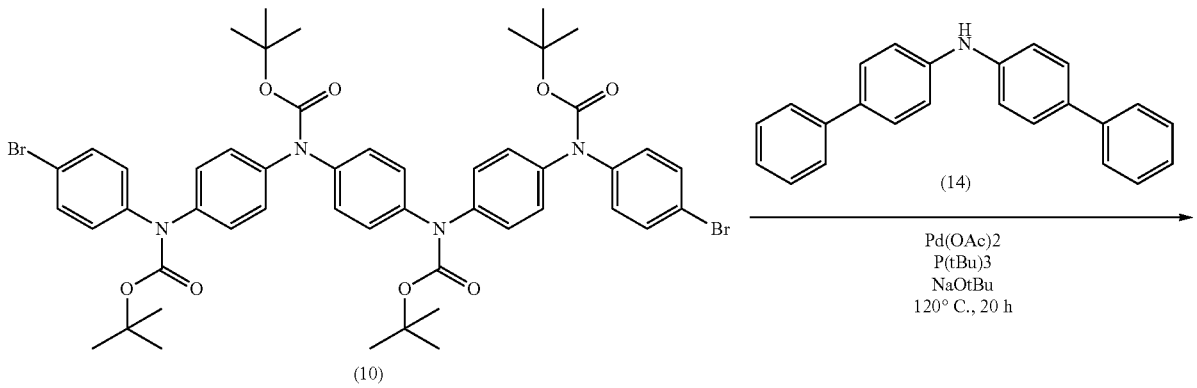

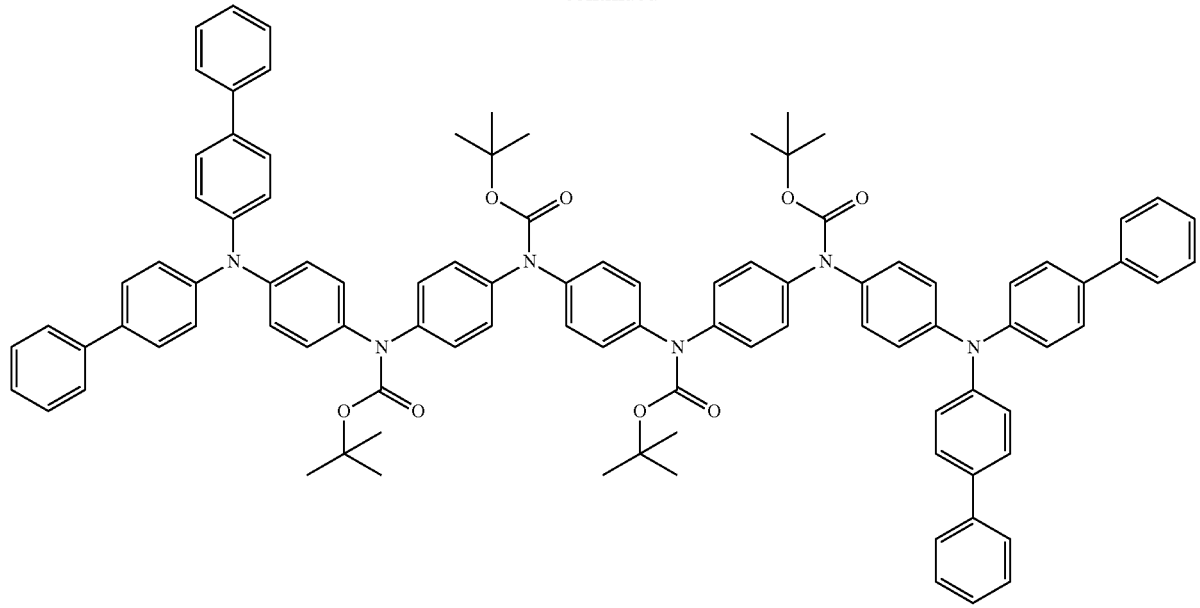

(15)

In a 300-mL three-neck flask were placed 200 mL of toluene, 67.2 mg (0.3 mmol) of palladium acetate, and an ellipsoidal stirring chip. The two outer necks were closed with septum caps and the center neck was provided with a reflux coiled condenser. To the top of the condenser was attached a three-way stopcock, to which is attached a balloon filled with nitrogen gas. The atmosphere in the flask was replaced three times by nitrogen gas supplied from the balloon with the help of a vacuum pump. Into the flask was injected 1.2 g (6 mmol) of tris-t-butylphosphine by means of a syringe, followed by stirring for five to ten minutes at room temperature. The flask was further charged with 10 g (9.99 mmol) of the compound (10) obtained in the step [1-2], 6.42 g (20 mmol) of the compound (14) obtained in the step [2-2], and 2.1 g (22 mmol) of sodium t-butoxide. With the flask placed on an oil bath, the solution therein was gradually heated to 120° C. with stirring. After 20 hours, the flask was dismounted from the oil bath so as to terminate reaction, and the solution was allowed to cool to room temperature in an atmosphere of nitrogen. The reaction solution was transferred to a separatory funnel and was given 70 mL of diethyl ether. It was washed several times with 100 mL of saturated aqueous solution of sodium chloride. The organic layer was separated and dried with anhydrous magnesium sulfate. With the anhydrous magnesium sulfate filtered out, the organic layer was freed of the solvent by means of an evaporator. Thus there was obtained a crude product in a yield of 85%. This crude product was used as such for the ensuing reactions because it involved difficulties in isolation and purification.

[2-4] Removal of BOC

[Chemical Formula 17]

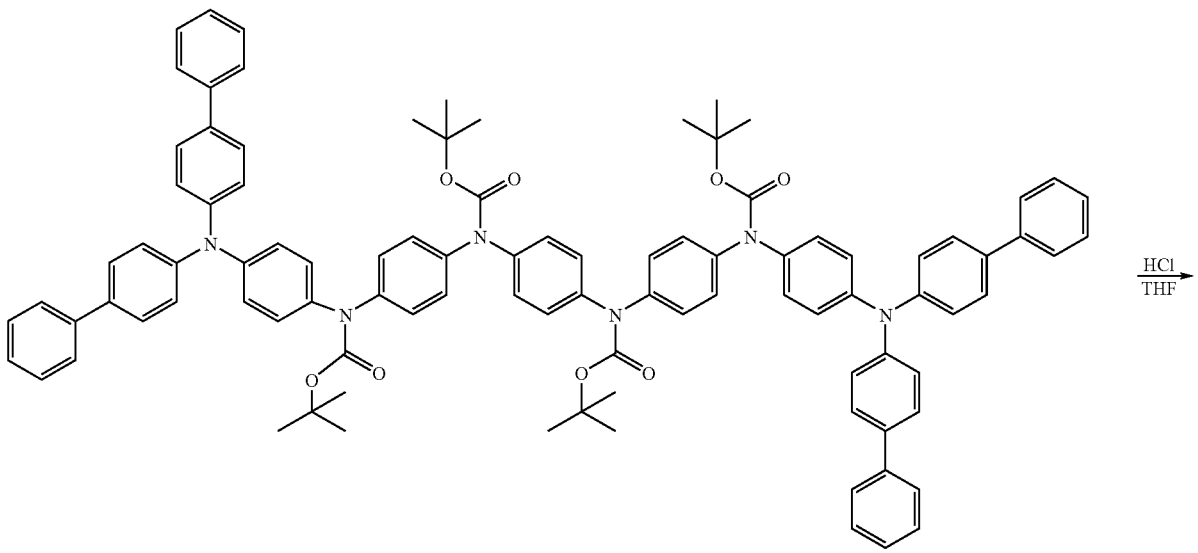

(15)

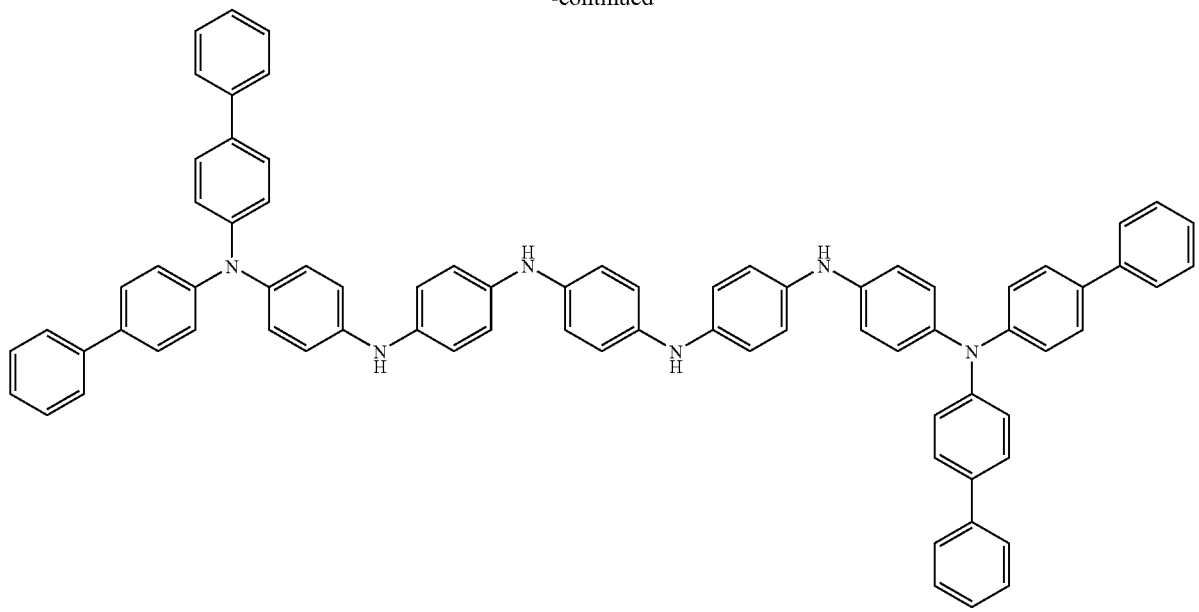

(16)

In a 500-mL eggplant-shaped flask were placed 10 g (6.75 mmol) of the compound (15) obtained in the step [2-3], 200 mL of tetrahydrofuran, 50 mL of aqueous solution of 4N hydrochloric acid, and an ellipsoidal stirring chip. With the flask equipped with a reflux coiled condenser, reaction was carried out at 65° C. for five hours in the air. The flask was allowed to cool to terminate reaction. The reaction solution was transferred to a separatory funnel and washed therein several times with 50 mL of saturated aqueous solution of sodium hydroxide and further several times with water. The organic layer was dehydrated with anhydrous magnesium sulfate, which was discarded later by filtration. The filtrate was freed of solvent by means of an evaporator. Thus there was obtained a crude product in a yield of 80%. This crude product was treated with activated carbon and recrystallized according to the process used in Comparative Example 1 (Yields: 95%).

1H-NMR; δ 6.9-7.5 (Ar, 56H, m), 7.55-7.65 (—NH, 4H) ppm

Molecular weight; 1081.35

MALDI-TOF; 1079.69[M]+

Example 3

[3-1] Synthesis of 4-Bromodiphenylamine

[Chemical Formula 18]

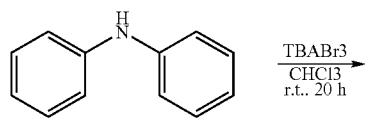

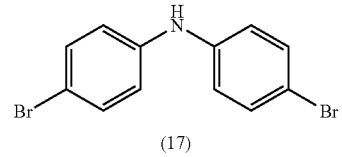

(17)

In a 1000-mL Erlenmeyer flask were placed 20 g (118.1 mmol) of diphenylamine, 500 mL of chloroform, and an ellipsoidal stirring chip. In a 500-mL beaker was placed 113.8 g (236.2 mmol) of tetrabutylammoniumtribromide (TBABr₃), which was dissolved in 200 mL of chloroform added later. The resulting solution was added dropwise to the chloroform-diphenylamine solution, and the mixture was stirred for 20 hours at room temperature in the air. Then, the chloroform-diphenylamine solution was transferred to a 1000-mL separatory funnel and washed seven times with 100 mL of saturated aqueous solution of sodium thiosulfate. The organic layer was transferred to a 1000-mL Erlenmeyer flask and then dehydrated with 100 g of anhydrous magnesium sulfate. With the anhydrous magnesium sulfate removed by filtration, the chloroform solution was transferred to a 1000-mL eggplant-shaped flask and freed of chloroform by means of an evaporator. The resulting crude product was purified by means of a silica gel column (hexane:chloroform=1:1) (Yields: 70%).

1H-NMR; δ 5.8 (—NH, 1H, s), 7.0-7.6 (Ar, 8H, d) ppm

[3-2] Introduction of BOC

[Chemical Formula 19]

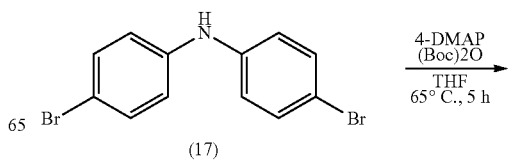

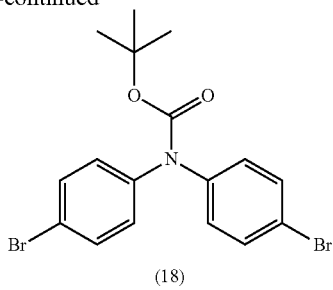

(18)

In a 500-mL eggplant-shaped flask were placed 10 g (30.58 mmol) of the compound (17) obtained by the step [3-1], 0.74 g (6.1 mmol) of 4-dimethylaminopyridine, 8.0 g (36.7 mmol) of di-t-butyl dicarbonate, and 400 mL of THF. They underwent reaction at 65° C. for five hours. After reaction was complete, THF was removed by means of an evaporator. The resulting crude produce was purified by means of a silica gel column (hexane:chloroform:ethyl acetate=10:10:1) (Yields: 80%).

1H-NMR; δ 1.38 ($CH_3$, 9H, s), 7.0-7.6 (Ar, 8H, d) ppm

[3-3] Coupling Reaction

[Chemical Formula 20]

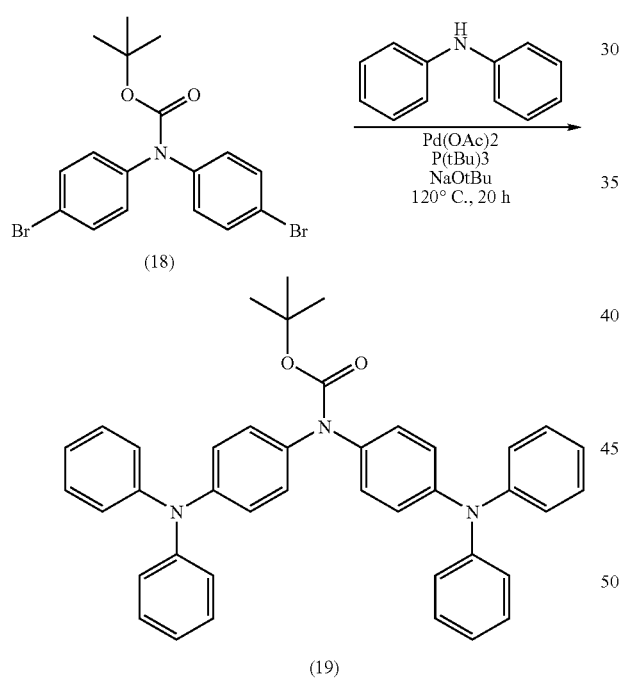

In a 300-mL three-neck flask were placed 200 mL of toluene, 157.3 mg (0.702 mmol) of palladium acetate, and an ellipsoidal stirring chip. The two outer necks were closed with septum caps and the center neck was provided with a reflux coiled condenser. To the top of the condenser was attached a three-way stopcock, to which is attached a balloon filled with nitrogen gas. The atmosphere in the flask was replaced three times by nitrogen gas supplied from the balloon with the help of a vacuum pump. Into the flask was injected 2.84 g (14 mmol) of tris-t-butylphosphine by means of a syringe, followed by stirring for five to ten minutes at room temperature. The flask was further charged with 10 g (23.41 mmol) of the compound (18) obtained in the step [3-2], 7.92 g (46.82 mmol) of diphenylamine, and 4.6 g (48 mmol) of sodium t-butoxide. With the flask placed on an oil bath, the solution therein was gradually heated to 120° C. with stirring. After 20 hours, the flask was dismounted from the oil bath so as to terminate reaction, and the solution was allowed to cool to room temperature in an atmosphere of nitrogen. The reaction solution was transferred to a separatory funnel and was given 70 mL of diethyl ether. It was washed several times with 100 mL of saturated aqueous solution of sodium chloride. The organic layer was separated and dried with anhydrous magnesium sulfate. With the anhydrous magnesium sulfate filtered out, the organic layer was freed of the solvent by means of an evaporator. Thus there was obtained a crude product (Yields: 90%).

1H-NMR; δ 1.38 ($CH_3$, 9H, s), 6.9-7.8 (Ar, 28H, m) ppm

[3-4] Removal of BOC

[Chemical Formula 21]

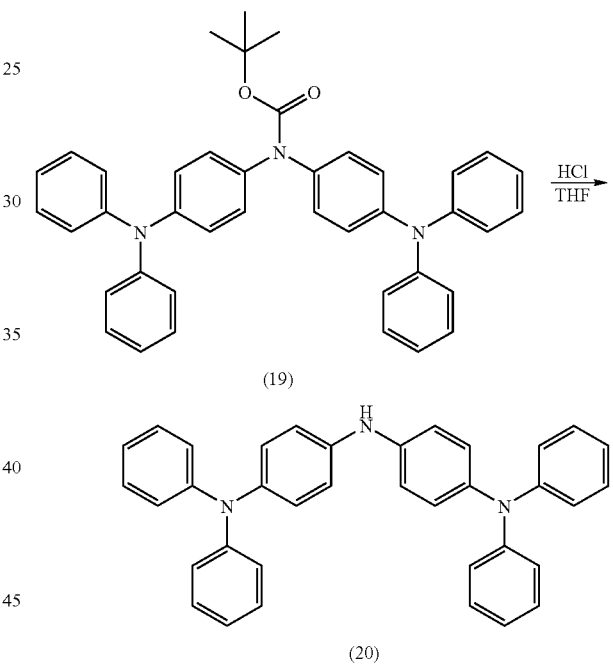

In a 500-mL eggplant-shaped flask were placed 10 g (16.56 mmol) of the compound (19) obtained in the step [3-3], 200 mL of tetrahydrofuran, 20 mL of aqueous solution of 4N hydrochloric acid, and an ellipsoidal stirring chip. With the flask equipped with a reflux coiled condenser, reaction was carried out at 65° C. for five hours in the air. The flask was allowed to cool to terminate reaction. The reaction solution was transferred to a separatory funnel and washed therein several times with 50 mL of saturated aqueous solution of sodium hydroxide and further several times with water. The organic layer was dehydrated with anhydrous magnesium sulfate, which was discarded later by filtration. The filtrate was freed of solvent by means of an evaporator. Thus there was obtained a crude product, which was subsequently purified by means of a silica gal column (hexane:chloroform=1:1) (Yields: 80%).

1H-NMR; δ 6.9-7.8 (Ar, 28H, m) ppm

[3-5] Coupling Reaction

[Chemical Formula 22]

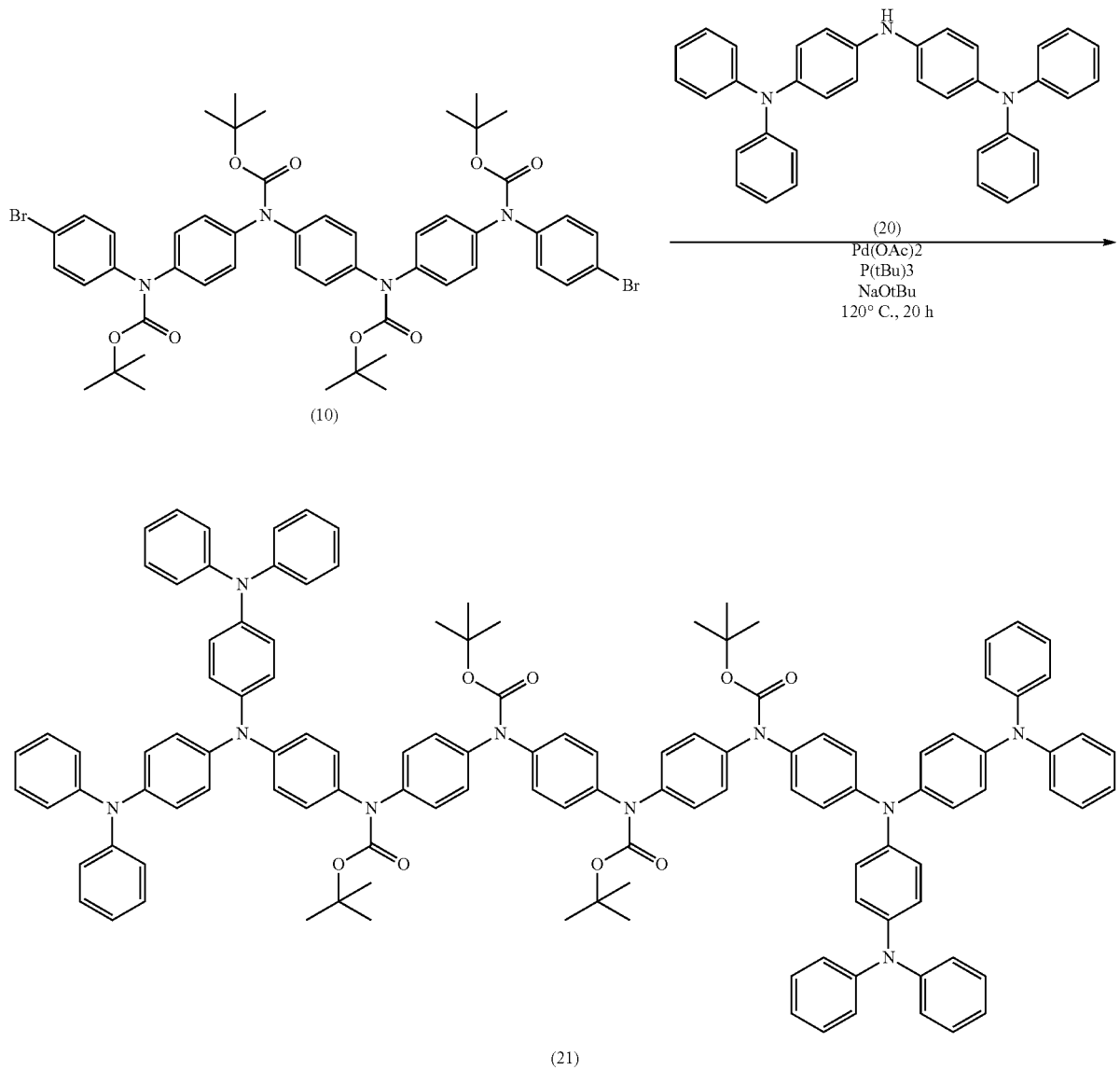

In a 300-mL three-neck flask were placed 200 mL of toluene, 0.67 g (0.3 mmol) of palladium acetate, and an ellipsoidal stirring chip. The two outer necks were closed with septum caps and the center neck was provided with a reflux coiled condenser. To the top of the condenser was attached a three-way stopcock, to which is attached a balloon filled with nitrogen gas. The atmosphere in the flask was replaced three times by nitrogen gas supplied from the balloon with the help of a vacuum pump. Into the flask was injected 1.2 g (6 mmol) of tris-t-butylphosphine by means of a syringe, followed by stirring for five to ten minutes at room temperature. The flask was further charged with 10 g (9.99 mmol) of the compound (10) obtained in the step [1-2], 10.07 g (20 mmol) of the compound (20) obtained in the step [3-4], and 2 g (20.98 mmol) of sodium t-butoxide. With the flask placed on an oil bath, the solution therein was gradually heated to 120° C. with stirring. After 20 hours, the flask was dismounted from the oil bath so as to terminate reaction, and the solution was allowed to cool to room temperature in an atmosphere of nitrogen. The reaction solution was transferred to a separatory funnel and was given 70 mL of diethyl ether. It was washed several times with 100 mL of saturated aqueous solution of sodium chloride. The organic layer was separated and dried with anhydrous magnesium sulfate. With the anhydrous magnesium sulfate filtered out, the organic layer was freed of solvent by means of an evaporator. Thus there was obtained a crude product in a yield of 85%. This crude product was used as such for the ensuing reactions because it involved difficulties in isolation and purification.

[3-6] Removal of ROC

[Chemical Formula 23]

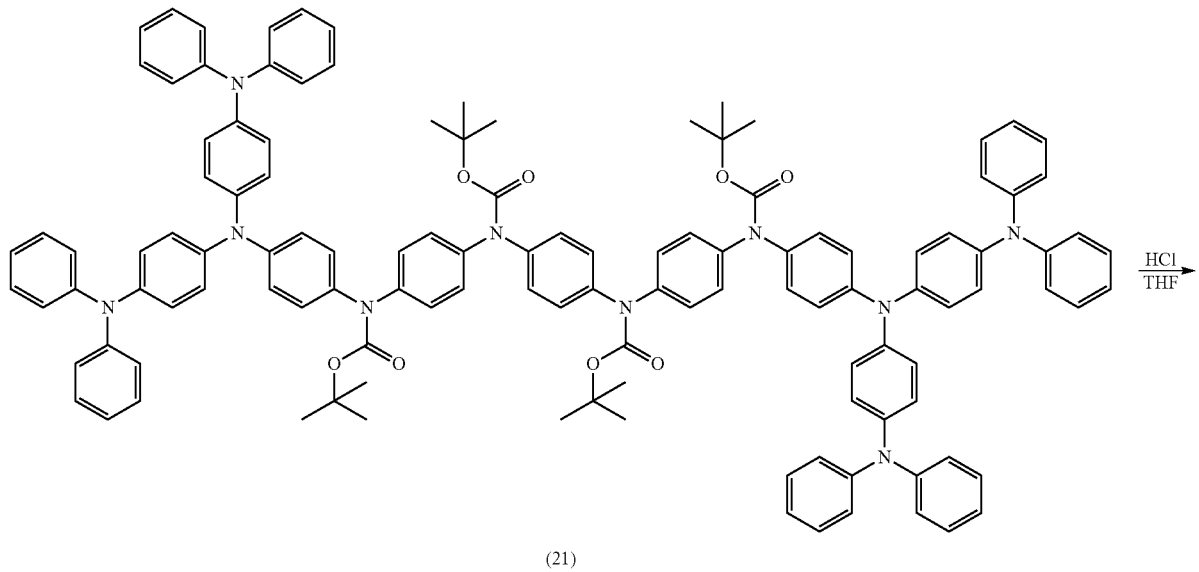

(21)

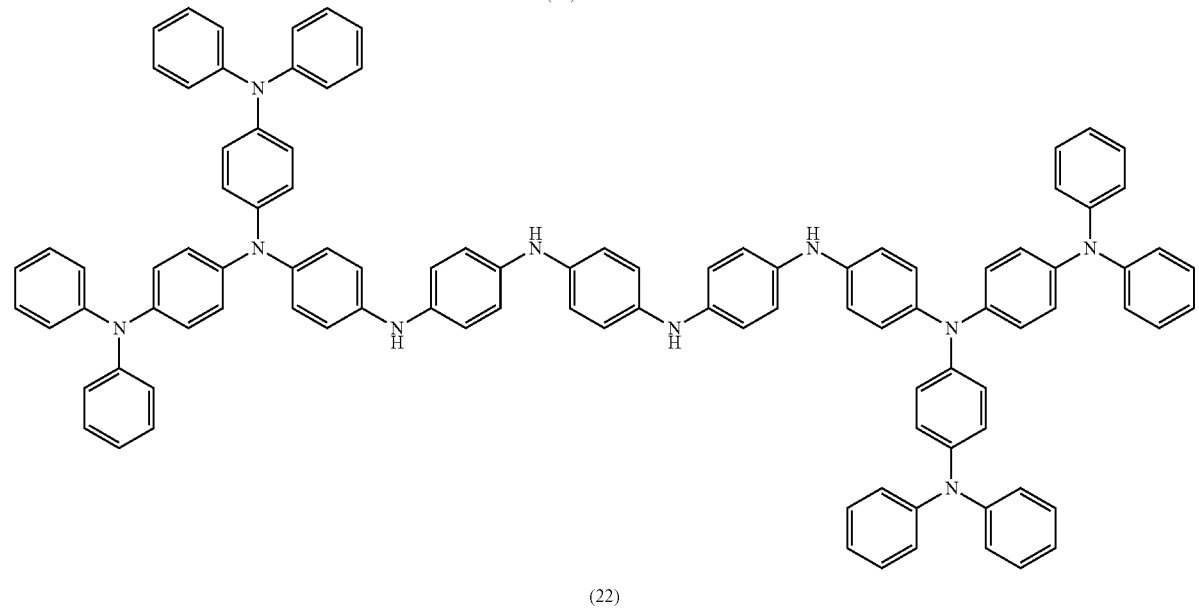

(22)

In a 500-mL eggplant-shaped flask were placed 10 g (5.41 mmol) of the compound (21) obtained in the step [3-5], 200 mL of tetrahydrofuran, 50 mL of aqueous solution of 4N hydrochloric acid, and an ellipsoidal stirring chip. With the flask equipped with a reflux coiled condenser, reaction was carried out at 65° C. for five hours in the air. The flask was allowed to cool to terminate reaction. The reaction solution was transferred to a separatory funnel and washed therein several times with 50 mL of saturated aqueous solution of sodium hydroxide and further several times with water. The organic layer was dehydrated with anhydrous magnesium sulfate, which was discarded later by filtration. The filtrate was freed of solvent by means of an evaporator. Thus there was obtained a crude product in a yield of 80%. This crude product was treated with activated carbon and recrystallized according to the process used in Comparative Example 1 (Yields: 95%).

1H-NMR; δ 6.9-7.3 (Ar, 72H, m) ppm
Molecular weight; 1445.79
MALDI-TOF; 1443.53[M]$^+$ Example 4

[4-1] Synthesis of 3,4-difluorophenylphenylamine

[Chemical Formula 24]

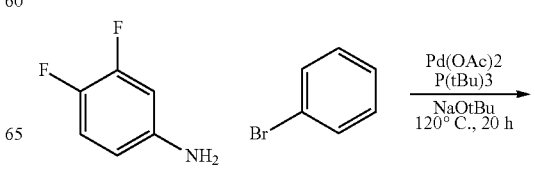

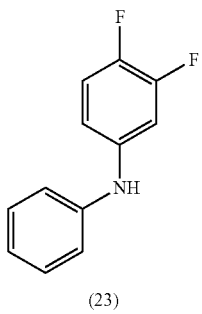

(23)

In a 300-mL three-neck flask were placed 200 mL of toluene, 0.21 g (0.96 mmol) of palladium acetate, and an ellipsoidal stirring chip. The two outer necks were closed with septum caps and the center neck was provided with a reflux coiled condenser. To the top of the condenser was attached a three-way stopcock, to which is attached a balloon filled with nitrogen gas. The atmosphere in the flask was replaced three times by nitrogen gas supplied from the balloon with the help of a vacuum pump. Into the flask was injected 3.8 g (18.9 mmol) of tris-t-butylphosphine by means of a syringe, followed by stirring for five to ten minutes at room temperature. The flask was further charged with 10 g (63.7 mmol) of 4-bromobenzene, 4.11 g (31.8 mmol) of 3,4-difluoroaniline, and 6.1 g (63.7 mmol) of sodium t-butoxide. With the flask placed on an oil bath, the solution therein was gradually heated to 120° C. with stirring. After 20 hours, the flask was dismounted from the oil bath so as to terminate reaction, and the solution was allowed to cool to room temperature in an atmosphere of nitrogen. The reaction solution was transferred to a separatory funnel and was given 70 mL of diethyl ether. It was washed several times with 100 mL of saturated aqueous solution of sodium chloride. The organic layer was separated and dried with anhydrous magnesium sulfate. With the anhydrous magnesium sulfate filtered out, the organic layer was freed of solvent by means of an evaporator. Thus there was obtained a crude product, which was subsequently purified by means of a silica gel column (hexane:chloroform=2:1) (Yields: 92%).

1H-NMR; δ 5.8 (—NH, 1H, s), 6.9-7.8 (Ar, 8H, m) ppm

[4-2] Coupling Reaction

[Chemical Formula 25]

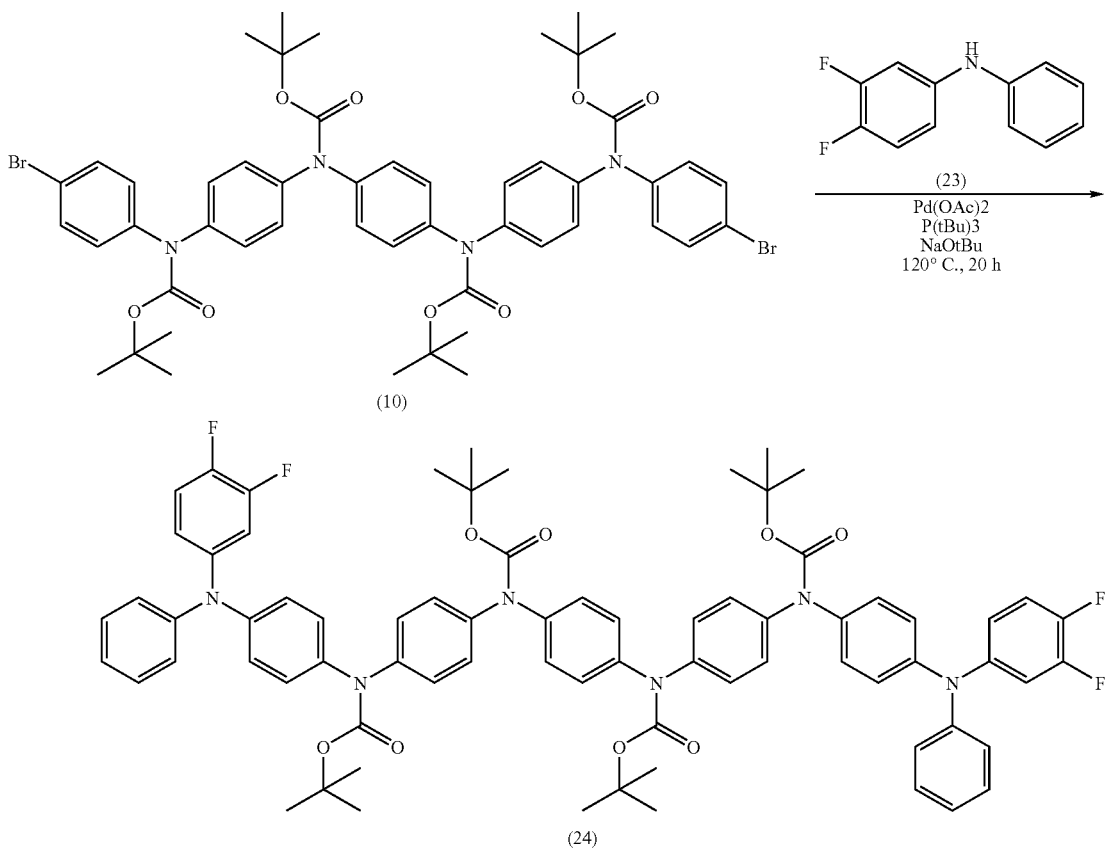

(10) obtained in the step [1-2], 4.1 g (20 mmol) of the compound (23) obtained in the step [4-1], and 2 g (20.98 mmol) of sodium t-butoxide. With the flask placed on an oil bath, the solution therein was gradually heated to 120° C. with stirring. After 20 hours, the flask was dismounted from the oil bath so as to terminate reaction, and the solution was allowed to cool to room temperature in an atmosphere of nitrogen. The reaction solution was transferred to a separatory funnel and was given 70 mL of diethyl ether. It was washed several times with 100 mL of saturated aqueous solution of sodium chloride. The organic layer was separated and dried with anhydrous magnesium sulfate. With the anhydrous magnesium sulfate filtered out, the organic layer was freed of solvent by means of an evaporator. Thus there was obtained a crude product in a yield of 72%. This crude product was used as such for the ensuing reactions because it involved difficulties in isolation and purification.

[4-3] Removal of BOC

[Chemical Formula 26]

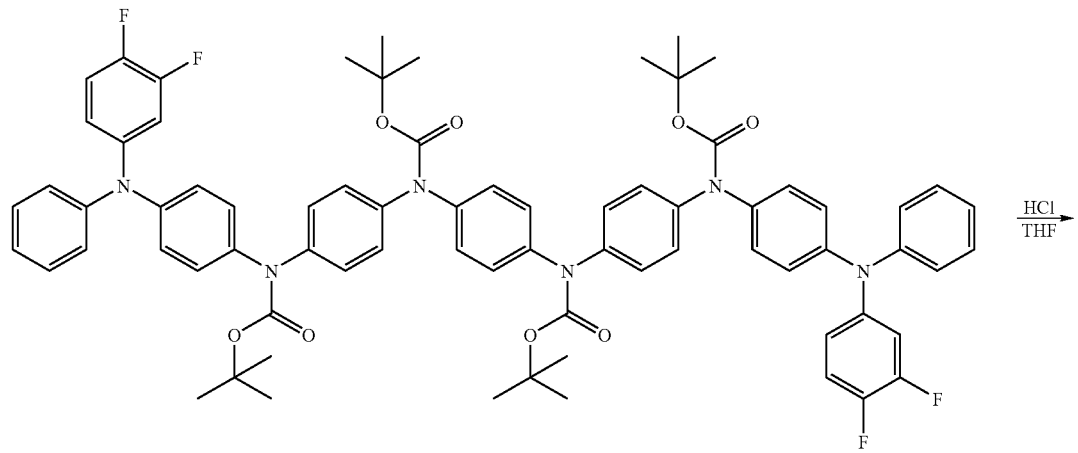

(24)

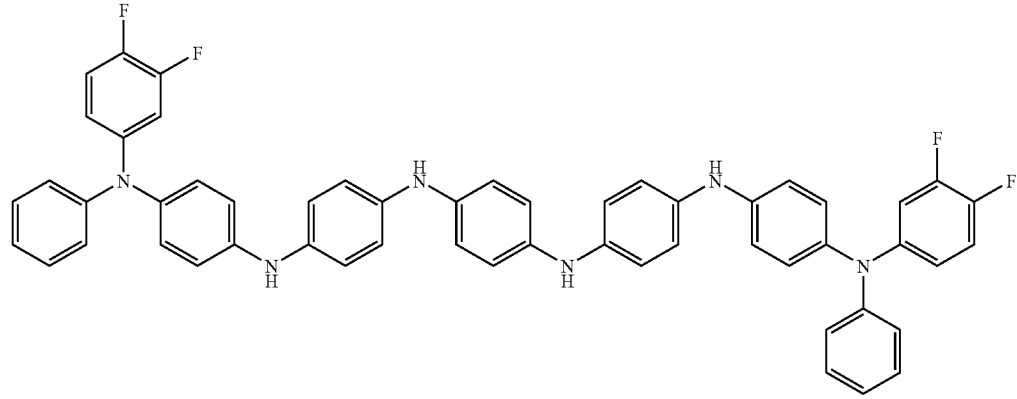

(25)

In a 500-mL eggplant-shaped flask were placed 10 g (8.0 mmol) of the compound (24) obtained in the step [4-3], 200 mL of tetrahydrofuran, 50 mL of aqueous solution of 4N hydrochloric acid, and an ellipsoidal stirring chip. With the flask equipped with a reflux coiled condenser, reaction was carried out at 65° C. for five hours in the air. The flask was allowed to cool to terminate reaction. The reaction solution was transferred to a separatory funnel and washed therein several times with 50 mL of saturated aqueous solution of sodium hydroxide and further several times with water. The organic layer was dehydrated with anhydrous magnesium sulfate, which was discarded later by filtration. The filtrate was freed of solvent by means of an evaporator. Thus there was obtained a crude product in a yield of 80%. This crude product was treated with activated carbon and recrystallized according to the process used in Comparative Example 1 (Yields: 95%).

1H-NMR; δ 6.8-7.3 (Ar, 36H, m), 7.55-7.85 (—NH, 4H) ppm

Molecular weight; 848.93

MALDI-TOF; 848.01[M]$^+$

[2] Preparation of Charge Transport Varnish and Charge Transport Thin Film

Comparative Example 2

One mole of PTA (obtained in Comparative Example 1) and 12 moles of 5-sulfosalicylic acid (both in equivalence) were dissolved in a solvent composed of 1,3-dimethyl-2-imidazolidinon (DMI) and cyclohexanol in a ratio of 2:4 by weight, such that the resulting solution contained 15 wt % of solids. This solution (as a varnish) was made into a thin film on an ITO glass substrate by spin coating.

Example 5

One mole of the compound (12) (obtained in Example 1) and 12 moles of 5-sulfosalicylic acid (both in equivalence)

were dissolved in a solvent composed of 1,3-dimethyl-2-imidazolidinon (DMI) and cyclohexanol in a ratio of 2:4 by weight, such that the resulting solution contained 15 wt % of solids. This solution (as a varnish) was made into a thin film on an ITO glass substrate by spin coating.

Example 6

The same procedure as in Example 5 was repeated to prepare a varnish and a thin film except that the compound (16) obtained in Example 2 was used.

Example 7

The same procedure as in Example 5 was repeated to prepare a varnish and a thin film except that the compound (22) obtained in Example 3 was used.

Example 8

The same procedure as in Example 5 was repeated to prepare a varnish and a thin film except that the compound (25) obtained in Example 4 was used.

Samples of the thin film prepared in Comparative Example 2 and Examples 5 to 8 mentioned above were examined for thickness and conductivity. The results are shown in Table 1.

Incidentally, thickness was measured by means of Surface State Measuring Apparatus DEKTAK3ST, made by Nippon Shinkuu Gijutu Inc., and conductivity was measured by means of Semiconductor Parameter Analyzer 4156C, made by Agilent Inc.

TABLE 1

|  | 5-SSA (equivalent) | Film thickness (nm) | Conductivity (S/cm) |
| --- | --- | --- | --- |
| Comparative Example 2 | 12 | 154.6 | $4.11 \times 10^{-7}$ |
| Example 5 | 12 | 126.5 | $2.80 \times 10^{-6}$ |
| Example 6 | 12 | 147.3 | $6.10 \times 10^{-6}$ |
| Example 7 | 12 | 110.4 | $2.74 \times 10^{-5}$ |
| Example 8 | 12 | 121.4 | $3.70 \times 10^{-6}$ |

It is noted from Table 1 that the thin film in Examples 5 to 8 has a larger value of conductivity than that in Comparative Example 2. This suggests that the oligoaniline having the triphenylamine structure (obtained in Examples 1 to 4) excels PTA in conductivity.

[3] Preparation of Polymeric EL Device

Example 9

One mole of the compound (12) obtained in Example 1 and 2.5 moles of naphthalenedisulfonic acid oligomer (NSO-2) represented by the formula (26) above (both in equivalence) were dissolved in a solvent composed of 1,3-dimethyl-2-imidazolidinon (DMI) and cyclohexanol in a ratio of 2:4 by weight, such that the resulting solution contained 3 wt % of solids. This solution (as a varnish) was made into a thin film (about 50 nm thick) on an ITO glass substrate by spin coating. Then, a polymeric blue light emitting material (SPB-02T made by Merck Inc.) was dissolved in xylene such that the resulting solution contained about 1.5 wt % of solids. This solution (as a varnish) was made into a thin film (about 70 nm thick) by spin coating on the thin film which had been formed previously. The coated glass substrate was placed in a vacuum vapor deposition apparatus for deposition with barium (0.1 nm) and silver (100 nm) which serve as the cathode. This vapor deposition was carried out at a pressure equal to or lower than $8 \times 10^{-4}$ Pa with a deposition rate of 0.5 nm/s. Thus there was obtained a polymeric EL device.

Incidentally, NSO-2 was synthesized (in a yield of 81%) according to the procedure disclosed in WO 2006/025342 pamphlet.

Example 10

The same procedure as in Example 9 was repeated to prepare a polymeric EL device except that the compound (12) was replaced by the compound (16) obtained in Example 2.

Example 11

The same procedure as in Example 9 was repeated to prepare a polymeric EL device except that the compound (12) was replaced by the compound (25) obtained in Example 4.

The polymeric EL devices obtained in Examples 9 to 11 were tested for characteristic properties. The results are shown in Table 2.

This test was carried out by means of an apparatus for measuring the light-emitting efficiency of organic EL devices, EL1003 made by Precise Gauges Co., Ltd. (The same shall apply hereinafter.)

TABLE 2

|  | Emission start (V) | @ 8 V | | |
| --- | --- | --- | --- | --- |
|  |  | mA/cm² | cd/m² | cd/A |
| Example 9 | 12 | 331.8 | 7972 | 2.4 |
| Example 10 | 12 | 353.6 | 8320 | 2.4 |
| Example 11 | 12 | 319.6 | 9694 | 3.0 |

It is noted from Table 2 that the compounds obtained in Examples 1, 2, and 4 function as the hole transport material.

[4] Preparation of Oligomeric EL Device

Comparative Example 3

One mole of the compound (8) obtained in Comparative Example 1 and 1.0 mole of NSO-2 (both in equivalence) were dissolved in a solvent composed of 1,3-dimethyl-2-imidazolidinon (DMI) and cyclohexanol in a ratio of 2:4 by weight, such that the resulting solution contained 3 wt % of solids. This solution (as a varnish) was made into a thin film (about 30 nm thick) on an ITO glass substrate by spin coating. The coated substrate was placed in a vacuum vapor deposition apparatus and subjected to sequential vapor deposition with α-NPD, Alg₃, LiF, and Al, whose film thickness was 40 nm, 45 nm, 0.5 nm, and 100 nm, respectively. Vapor deposition was carried out at a pressure lower than $8 \times 10^{-4}$ Pa, and the rate of vapor deposition was 0.02 to 0.04 nm/s for LiF and 0.3 to 0.4 nm/s for others. During vapor deposition, the substrate was transferred from one position to another in a vacuum. Thus there was obtained an OLED device.

Example 12

One mole of the compound (12) obtained in Example 1 and 2.0 moles of NSO-2 (both in equivalence) were dissolved in a solvent composed of 1,3-dimethyl-2-imidazolidinone (DMI) and cyclohexanol in a ratio of 2:4 by weight, such that the resulting solution contained 3 wt % of solids. This solution (as a varnish) was made into a thin film (about 30 nm thick) on an ITO glass substrate by spin coating. The coated substrate underwent vacuum vapor deposition in the same way as in Comparative Example 3. Thus there was obtained an OLED device.

Example 13

One mole of the compound (16) obtained in Example 2 and 2.5 moles of NSO-2 (both in equivalence) were dissolved in a solvent composed of 1,3-dimethyl-2-imidazolidinone (DMI) and cyclohexanol in a ratio of 2:4 by weight, such that the resulting solution contained 3 wt % of solids. This solution (as a varnish) was made into a thin film (about 30 nm thick) on an ITO glass substrate by spin coating. The coated substrate underwent vacuum vapor deposition in the same way as in Comparative Example 3. Thus there was obtained an OLED device.

Example 14

One mole of the compound (22) obtained in Example 3 and 3.0 moles of NSO-2 (both in equivalence) were dissolved in a solvent composed of 1,3-dimethyl-2-imidazolidinone (DMI) and cyclohexanol in a ratio of 2:4 by weight, such that the resulting solution contained 3 wt % of solids. This solution (as a varnish) was made into a thin film (about 30 nm thick) on an ITO glass substrate by spin coating. The coated substrate underwent vacuum vapor deposition in the same way as in Comparative Example 3. Thus there was obtained an OLED device.

Samples of the OLED device obtained in Examples 12 to 14 and Comparative Example 3 were examined for characteristic properties. The results are shown in Table 3.

Incidentally, this test was carried out by means of an apparatus for measuring the light-emitting efficiency of organic EL devices, EL1003 made by Precise Gauges Co., Ltd.

TABLE 3

| | Emission start | @ 8 V | | |
|---|---|---|---|---|
| | (V) | mA/cm$^2$ | cd/m$^2$ | cd/A |
| Comparative Example 3 | 2.75 | 14.4 | 592 | 4.1 |
| Example 12 | 2.75 | 36.6 | 1656 | 4.5 |
| Example 13 | 2.50 | 23.2 | 939 | 4.1 |
| Example 14 | 2.75 | 23.4 | 974 | 4.2 |

It is noted from Table 3 that the OLED devices obtained in Examples 12 to 14 are superior to that obtained in Comparative Example 3 in current density and luminance characteristics at a prescribed voltage.

[5] Comparison Between Oligoaniline Compound and Dopant (NSO-2)

Example 15

The same procedure as in Example 9 was repeated to prepare a polymeric EL device except that the amount of NSO-2 was changed to 2.0 moles for one mole of the compound (12), both in equivalence.

Example 16

The same procedure as in Example 9 was repeated to prepare a polymeric EL device except that the amount of NSO-2 was changed to 3.0 moles for one mole of the compound (12), both in equivalence.

Samples of the polymeric EL device obtained in Examples 15 and 16 were examined for characteristic properties. The results are shown in Table 4. The results of Example 9 are also shown in Table 4.

TABLE 4

| | Emission start | @ 8 V | | |
|---|---|---|---|---|
| | (V) | mA/cm$^2$ | cd/m$^2$ | cd/A |
| Example 9 | 12 | 331.8 | 7972 | 2.4 |
| Example 15 | 12 | 364.9 | 8784 | 2.4 |
| Example 16 | 12 | 324.9 | 7432 | 2.3 |

[6] Incorporation with Silane Compound

Comparative Example 4

One mole of the compound (12) and 1.5 moles of NSO-2 (both in equivalence) were dissolved in a solvent composed of 1,3-dimethyl-2-imidazolidinone (DMI) and cyclohexanol in a ratio of 2:4 by weight, such that the resulting solution contained 3 wt % of solids. This solution (as a varnish) was made into a uniform thin film (about 50 nm thick) on an ITO glass substrate by spin coating.

Then, a polymeric blue light emitting material (SPB-02T made by Merck) was dissolved in xylene such that the resulting solution contained about 1.5 wt % of solids. This solution (as a varnish) was made into a thin film (about 70 nm thick) by spin coating on the thin film which had been formed previously. The coated glass substrate was placed in a vacuum vapor deposition apparatus for deposition with barium (0.1 nm) and silver (100 nm) which serve as the cathode. This vapor deposition was carried out at a pressure lower than $8 \times 10^{-4}$ Pa with a deposition rate of 0.5 nm/s.

Comparative Example 5

One mole of the compound (12) and 2.5 moles of NSO-2 (both in equivalence) were dissolved in a solvent composed of 1,3-dimethyl-2-imidazolidinone (DMI) and cyclohexanol in a ratio of 2:4 by weight, such that the resulting solution contained 3 wt % of solids. This solution (as a varnish) was used to prepare a polymeric EL device in the same way as in Comparative Example 4.

Example 17

One mole of the compound (12) and 1.5 moles of NSO-2 (both in equivalence) were dissolved in a solvent composed of 1,3-dimethyl-2-imidazolidinone (DMI) and cyclohexanol in a ratio of 2:4 by weight, such that the resulting solution contained 3 wt % of solids. This solution was incorporated with trifluoropropyltrimethoxysilane (a product of Shin-Etsu Silicones) in an amount of 4 wt % for 3 wt % of solids. The resulting solution (as a varnish) was used to prepare a polymeric EL device in the same way as in Comparative Example 4.

Example 18

One mole of the compound (12) and 2.5 moles of NSO-2 (both in equivalence) were dissolved in a solvent composed of 1,3-dimethyl-2-imidazolidinone (DMI) and cyclohexanol in a ratio of 2:4 by weight, such that the resulting solution contained 3 wt % of solids. This solution was incorporated with methyltriethoxysilane (a product of Shin-Etsu Silicones)

in an amount of 4 wt % for 3 wt % of solids. The resulting solution (as a varnish) was used to prepare a polymeric EL device in the same way as in Comparative Example 4.

Example 19

One mole of the compound (12) and 2.5 moles of NSO-2 (both in equivalence) were dissolved in a solvent composed of 1,3-dimethyl-2-imidazolidinone (DMI) and cyclohexanol in a ratio of 2:4 by weight, such that the resulting solution contained 3 wt % of solids. This solution was incorporated with ethyltriethoxysilane (a product of Shin-Etsu Silicones) in an amount of 4 wt % for 3 wt % of solids. The resulting solution (as a varnish) was used to prepare a polymeric EL device in the same way as in Comparative Example 4.

Example 20

One mole of the compound (12) and 2.5 moles of NSO-2 (both in equivalence) were dissolved in a solvent composed of 1,3-dimethyl-2-imidazolidinone (DMI) and cyclohexanol in a ratio of 2:4 by weight, such that the resulting solution contained 3 wt % of solids. This solution was incorporated with vinyltrimethoxysilane (a product of Shin-Etsu Silicones) in an amount of 4 wt % for 3 wt % of solids. The resulting solution (as a varnish) was used to prepare a polymeric EL device in the same way as in Comparative Example 4.

Example 21

One mole of the compound (12) and 2.5 moles of NSO-2 (both in equivalence) were dissolved in a solvent composed of 1,3-dimethyl-2-imidazolidinone (DMI) and cyclohexanol in a ratio of 2:4 by weight, such that the resulting solution contained 3 wt % of solids. This solution was incorporated with trifluoropropyltrimethoxysilane (a product of Shin-Etsu Silicones) in an amount of 4 wt % for 3 wt % of solids. The resulting solution (as a varnish) was used to prepare a polymeric EL device in the same way as in Comparative Example 4.

Example 22

One mole of the compound (12) and 2.5 moles of NSO-2 (both in equivalence) were dissolved in a solvent composed of 1,3-dimethyl-2-imidazolidinone (DMI) and cyclohexanol in a ratio of 2:4 by weight, such that the resulting solution contained 3 wt % of solids. This solution was incorporated with phenyltrimethoxysilane (a product of Shin-Etsu Silicones) in an amount of 4 wt % for 3 wt % of solids. The resulting solution (as a varnish) was used to prepare a polymeric EL device in the same way as in Comparative Example 4

Example 23

One mole of the compound (12) and 2.5 moles of NSO-2 (both in equivalence) were dissolved in a solvent composed of 1,3-dimethyl-2-imidazolidinone (DMI) and cyclohexanol in a ratio of 2:4 by weight, such that the resulting solution contained 3 wt % of solids. This solution was incorporated with propyltriethoxysilane (a product of Shin-Etsu Silicones) in an amount of 4 wt % for 3 wt % of solids. The resulting solution (as a varnish) was used to prepare a polymeric EL device in the same way as in Comparative Example 4.

Example 24

One mole of the compound (12) and 1.5 moles of NSO-2 (both in equivalence) were dissolved in a solvent composed of 1,3-dimethyl-2-imidazolidinone (DMI) and cyclohexanol in a ratio of 2:4 by weight, such that the resulting solution contained 3 wt % of solids. This solution was incorporated with trifluoropropyltrimethoxysilane and phenyltrimethoxysilane (products of Shin-Etsu Silicones) in a ratio of 2:5 by weight, in a total amount of 4 wt % for 3 wt % of solids. The resulting solution (as a varnish) was used to prepare a polymeric EL device in the same way as in Comparative Example 4.

Example 25

One mole of the compound (12) and 2.5 moles of NSO-2 (both in equivalence) were dissolved in a solvent composed of 1,3-dimethyl-2-imidazolidinone (DMI) and cyclohexanol in a ratio of 2:4 by weight, such that the resulting solution contained 3 wt % of solids. This solution was incorporated with trifluoropropyltrimethoxysilane and phenyltrimethoxysilane (products of Shin-Etsu Silicones) in a ratio of 2:5 by weight in a total amount of 4 wt % for 3 wt % of solids. The resulting solution (as a varnish) was used to prepare a polymeric EL device in the same way as in Comparative Example 4.

Table 5 shows the characteristic properties of the EL devices prepared in Examples 17 to 25 and Comparative Examples 4 and 5 mentioned above.

TABLE 5

| | Emission | 100 mA/cm$^2$ | | |
| --- | --- | --- | --- | --- |
| | start (V) | Voltage (V) | Luminance (cd/m$^2$) | Efficiency (cd/A) |
| Example 17 | 2.5 | 6 | 2305 | 2.2 |
| Example 18 | 2.5 | 5.5 | 3180 | 2.97 |
| Example 19 | 2.5 | 5.5 | 2761 | 2.75 |
| Example 20 | 2.5 | 5.5 | 2717 | 2.51 |
| Example 21 | 2.5 | 5.5 | 2828 | 2.75 |
| Example 22 | 2.5 | 5.5 | 2850 | 2.73 |
| Example 23 | 2.5 | 5.5 | 3479 | 3.19 |
| Example 24 | 2.5 | 5.75 | 1923 | 2.0 |
| Example 25 | 2.5 | 5.5 | 3441 | 3.3 |
| Comparative Example 4 | 2.5 | 6.25 | 1413 | 1.31 |
| Comparative Example 5 | 2.5 | 5.75 | 2525 | 2.35 |

The EL devices prepared in Comparative Examples 4 and 5 and Examples 24 and 25 were examined for life, with the initial luminance of 1000 cd/m$^2$ (measured with constant current). The life is expressed in terms of half-life required for the luminance to decrease to 500 cd/m$^2$. The results are shown in Table 6.

TABLE 6

| | Half-life (h) |
| --- | --- |
| Example 24 | 27 |
| Example 25 | 30 |
| Comparative Example 4 | 10 |
| Comparative Example 5 | 22 |

It is noted from Table 6 that the devices extend their life in the case where the charge transport varnish is incorporated with silane compounds.

Comparative Example 6

One mole of the compound (12) and 1.5 moles of NSO-2 (both in equivalence) were dissolved in a solvent composed of dimethylacetamide, cyclohexanol, and 2,3-butanediol in a ratio of 2:3:1 by weight, such that the resulting solution contained 3.5 wt % of solids. This solution (as a varnish) was made into a uniform thin film (about 50 nm thick) on an ITO glass substrate by spin coating. This varnish was used to prepare the polymeric EL element in the same way as in Comparative Example 4.

Example 26

One mole of the compound (12) and 1.5 moles of NSO-2 (both in equivalence) were dissolved in a solvent composed of dimethylacetamide, cyclohexanol, and 2,3-butanediol in a ratio of 2:3:1 by weight, such that the resulting solution contained 3.5 wt % of solids. This solution was incorporated with 10 wt % of ethyltrimethoxysilane (made by Shin-Etsu Silicones) for the total amount of solids in the varnish. The resulting varnish was used to prepare the polymeric EL element in the same way as in Comparative Example 4.

Example 27

One mole of the compound (12) and 1.5 moles of NSO-2 (both in equivalence) were dissolved in a solvent composed of dimethylacetamide, cyclohexanol, and 2,3-butanediol in a ratio of 2:3:1 by weight, such that the resulting solution contained 3.5 wt % of solids. This solution was incorporated with 10 wt % of 3-acryloxypropyltrimethoxysilane (made by Shin-Etsu Silicones) for the total amount of solids in the varnish. The resulting varnish was used to prepare the polymeric EL element in the same way as in Comparative Example 4.

Example 28

One mole of the compound (12) and 1.5 moles of NSO-2 (both in equivalence) were dissolved in a solvent composed of dimethylacetamide, cyclohexanol, and 2,3-butanediol in a ratio of 2:3:1 by weight, such that the resulting solution contained 3.5 wt % of solids. This solution was incorporated with 10 wt % of methyltrimethoxysilane (made by Shin-Etsu Silicones) for the total amount of solids in the varnish. The resulting varnish was used to prepare the polymeric EL element in the same way as in Comparative Example 4.

Example 29

One mole of the compound (12) and 1.5 moles of NSO-2 (both in equivalence) were dissolved in a solvent composed of dimethylacetamide, cyclohexanol, and 2,3-butanediol in a ratio of 2:3:1 by weight, such that the resulting solution contained 3.5 wt % of solids. This solution was incorporated with 10 wt % of phenyltrimethoxysilane (made by Shin-Etsu Silicones) for the total amount of solids in the varnish. The resulting varnish was used to prepare the polymeric EL element in the same way as in Comparative Example 4.

Example 30

One mole of the compound (12) and 1.5 moles of NSO-2 (both in equivalence) were dissolved in a solvent composed of dimethylacetamide, cyclohexanol, and 2,3-butanediol in a ratio of 2:3:1 by weight, such that the resulting solution contained 3.5 wt % of solids. This solution was incorporated with 10 wt % of 3-aminopropyltriethoxysilane (made by Shin-Etsu Silicones) for the total amount of solids in the varnish. The resulting varnish was used to prepare the polymeric EL element in the same way as in Comparative Example 4.

Example 31

One mole of the compound (12) and 1.5 moles of NSO-2 (both in equivalence) were dissolved in a solvent composed of dimethylacetamide, cyclohexanol, and 2,3-butanediol in a ratio of 2:3:1 by weight, such that the resulting solution contained 3.5 wt % of solids. This solution was incorporated with 10 wt % of 3-glycidoxypropyltrimethoxysilane (made by Shin-Etsu Silicones) for the total amount of solids in the varnish. The resulting varnish was used to prepare the polymeric EL element in the same way as in Comparative Example 4.

Example 32

One mole of the compound (12) and 1.5 moles of NSO-2 (both in equivalence) were dissolved in a solvent composed of dimethylacetamide, cyclohexanol, and 2,3-butanediol in a ratio of 2:3:1 by weight, such that the resulting solution contained 3.5 wt % of solids. This solution was incorporated with 10 wt % of tetramethoxysilane (made by Junsei Chemical Co., Ltd.) for the total amount of solids in the varnish. The resulting varnish was used to prepare the polymeric EL element in the same way as in Comparative Example 4.

Example 33

One mole of the compound (12) and 1.5 moles of NSO-2 (both in equivalence) were dissolved in a solvent composed of dimethylacetamide, cyclohexanol, and 2,3-butanediol in a ratio of 2:3:1 by weight, such that the resulting solution contained 3.5 wt % of solids. This solution was incorporated with 10 wt % of 3,3,3-trifluoropropyltrimethoxysilane (made by Shin-Etsu Silicones) for the total amount of solids in the varnish. The resulting varnish was used to prepare the polymeric EL element in the same way as in Comparative Example 4.

Example 34

One mole of the compound (12) and 1.5 moles of NSO-2 (both in equivalence) were dissolved in a solvent composed of dimethylacetamide, cyclohexanol, and 2,3-butanediol in a ratio of 2:3:1 by weight, such that the resulting solution contained 3.5 wt % of solids. This solution was incorporated with 10 wt % of 3-mercaptopropyltrimethoxysilane (made by Shin-Etsu Silicones) for the total amount of solids in the varnish. The resulting varnish was used to prepare the polymeric EL element in the same way as in Comparative Example 4.

Example 35

One mole of the compound (12) and 1.5 moles of NSO-2 (both in equivalence) were dissolved in a solvent composed of dimethylacetamide, cyclohexanol, and 2,3-butanediol in a ratio of 2:3:1 by weight, such that the resulting solution contained 3.5 wt % of solids. This solution was incorporated with 10 wt % of triethoxy(4-(trifluoromethyl)phenyl)silane (made by Aldrich) for the total amount of solids in the varnish.

The resulting varnish was used to prepare the polymeric EL element in the same way as in Comparative Example 4.

Example 36

One mole of the compound (12) and 1.5 moles of NSO-2 (both in equivalence) were dissolved in a solvent composed of dimethylacetamide, cyclohexanol, and 2,3-butanediol in a ratio of 2:3:1 by weight, such that the resulting solution contained 3.5 wt % of solids. This solution was incorporated with 10 wt % of dodecyltriethoxysilane (made by Shin-Etsu Silicones) for the total amount of solids in the varnish. The resulting varnish was used to prepare the polymeric EL element in the same way as in Comparative Example 4.

Example 37

One mole of the compound (12) and 1.5 moles of NSO-2 (both in equivalence) were dissolved in a solvent composed of dimethylacetamide, cyclohexanol, and 2,3-butanediol in a ratio of 2:3:1 by weight, such that the resulting solution contained 3.5 wt % of solids. This solution was incorporated with 10 wt % of dimethoxymethyl(3,3,3-trifluoropropyl)silane (made by Lancaster) for the total amount of solids in the varnish. The resulting varnish was used to prepare the polymeric EL element in the same way as in Comparative Example 4.

Example 38

One mole of the compound (12) and 1.5 moles of NSO-2 (both in equivalence) were dissolved in a solvent composed of dimethylacetamide, cyclohexanol, and 2,3-butanediol in a ratio of 2:3:1 by weight, such that the resulting solution contained 3.5 wt % of solids. This solution was incorporated with 10 wt % of diethoxydimethylsilane (made by Shin-Etsu Silicones) for the total amount of solids in the varnish. The resulting varnish was used to prepare the polymeric EL element in the same way as in Comparative Example 4.

Example 39

One mole of the compound (12) and 1.5 moles of NSO-2 (both in equivalence) were dissolved in a solvent composed of dimethylacetamide, cyclohexanol, and 2,3-butanediol in a ratio of 2:3:1 by weight, such that the resulting solution contained 3.5 wt % of solids. This solution was incorporated with 10 wt % of (triethoxysilyl)cyclohexane (made by Aldrich) for the total amount of solids in the varnish. The resulting varnish was used to prepare the polymeric EL element in the same way as in Comparative Example 4.

Example 40

One mole of the compound (12) and 1.5 moles of NSO-2 (both in equivalence) were dissolved in a solvent composed of dimethylacetamide, cyclohexanol, and 2,3-butanediol in a ratio of 2:3:1 by weight, such that the resulting solution contained 3.5 wt % of solids. This solution was incorporated with 10 wt % of triethoxy-2-thienylsilane (made by Aldrich) for the total amount of solids in the varnish. The resulting varnish was used to prepare the polymeric EL element in the same way as in Comparative Example 4.

Example 41

One mole of the compound (12) and 1.5 moles of NSO-2 (both in equivalence) were dissolved in a solvent composed of dimethylacetamide, cyclohexanol, and 2,3-butanediol in a ratio of 2:3:1 by weight, such that the resulting solution contained 3.5 wt % of solids. This solution was incorporated with 10 wt % of vinyltrimethoxysilane (made by Aldrich) for the total amount of solids in the varnish. The resulting varnish was used to prepare the polymeric EL element in the same way as in Comparative Example 4.

Example 42

One mole of the compound (12) and 1.5 moles of NSO-2 (both in equivalence) were dissolved in a solvent composed of dimethylacetamide, cyclohexanol, and 2,3-butanediol in a ratio of 2:3:1 by weight, such that the resulting solution contained 3.5 wt % of solids. This solution was incorporated with 10 wt % of tetramethoxysilane and metheyltrimethoxysilane (in a ratio of 2:1 by weight) for the total amount of solids in the varnish. The resulting varnish was used to prepare the polymeric EL element in the same way as in Comparative Example 4.

Example 43

One mole of the compound (12) and 1.5 moles of NSO-2 (both in equivalence) were dissolved in a solvent composed of dimethylacetamide, cyclohexanol, and 2,3-butanediol in a ratio of 2:3:1 by weight, such that the resulting solution contained 3.5 wt % of solids. This solution was incorporated with 10 wt % of phenyltrimethoxysilane and 3,3,3-trifluoropropyltrimethoxysilane (in a ratio of 2:1 by weight) for the total amount of solids in the varnish. The resulting varnish was used to prepare the polymeric EL element in the same way as in Comparative Example 4.

Example 44

One mole of the compound (12) and 1.5 moles of NSO-2 (both in equivalence) were dissolved in a solvent composed of dimethylacetamide, cyclohexanol, and 2,3-butanediol in a ratio of 2:3:1 by weight, such that the resulting solution contained 3.5 wt % of solids. This solution was incorporated with 10 wt % of tetramethoxysilane and 3,3,3-trifluoropropyltrimethoxysilane (in a ratio of 2:1 by weight) for the total amount of solids in the varnish. The resulting varnish was used to prepare the polymeric EL element in the same way as in Comparative Example 4.

Samples of the polymeric EL device prepared in Examples 26 to 44 and Comparative Example 6 were examined for luminance at 4V. The results in terms of ratio are shown in Table 7, with the value in Comparative Example 6 being one.

TABLE 7

|  | Luminance |
|---|---|
| Comparative Example 6 | 1 |
| Example 26 | 2 |
| Example 27 | 1 |
| Example 28 | 2 |
| Example 29 | 2 |
| Example 30 | 1 |
| Example 31 | 1 |
| Example 32 | 2 |
| Example 33 | 4 |
| Example 34 | 1 |
| Example 35 | 5 |
| Example 36 | 1 |
| Example 37 | 1 |
| Example 38 | 1 |

TABLE 7-continued

|  | Luminance |
|---|---|
| Example 39 | 2 |
| Example 40 | 2 |
| Example 41 | 1 |
| Example 42 | 4 |
| Example 43 | 4 |
| Example 44 | 3 |

It is noted from the foregoing that incorporation of silane compounds into the charge transport varnish improves the characteristic properties of the EL device.

The invention claimed is:

1. A compound selected from the group consisting of an oligoaniline compound of formula 1 and an oxidized form of an oligoaniline compound of formula 1, wherein formula (1) is as follows:

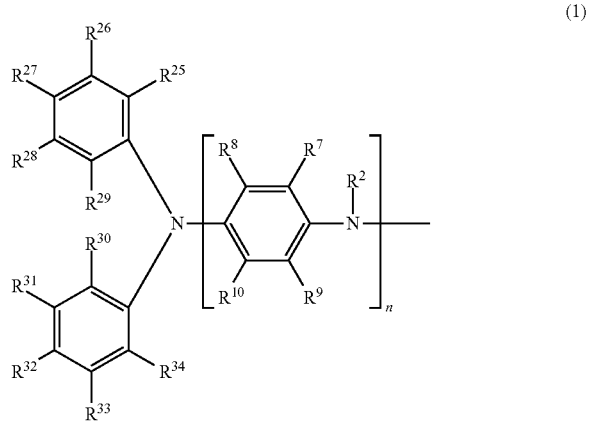

(1)

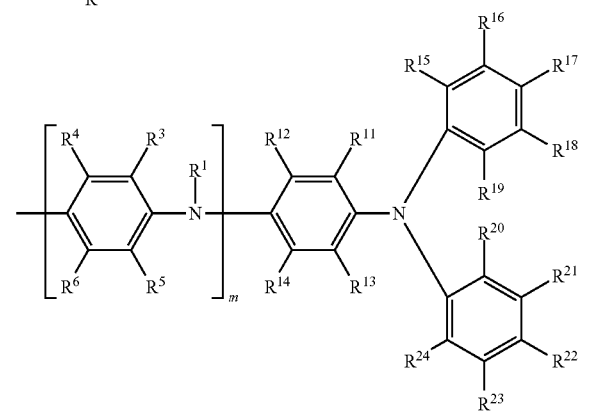

wherein $R^1$ and $R^2$ each independently denote a hydrogen atom, substituted or unsubstituted alkyl group, cycloalkyl group, bicycloalkyl group or alkenyl group, t-butoxycarbonyl group, or benzyloxycarbonyl group; $R^3$-$R^{34}$ each independently denote a hydrogen atom, hydroxyl group, silanol group, thiol group, carboxyl group, phosphoric acid group, phosphoric ester group, ester group, thioester group, amido group, nitro group, substituted or unsubstituted monovalent hydrocarbon group, organooxy group, organoamino group, organosilyl group, organothio group, acyl group, sulfonic group, or halogen atom; and m and n each denote an integer no smaller than 1 such that m+n≦20.

2. The compound as defined in claim 1, wherein $R^1$ and $R^2$ each independently denote a hydrogen atom or t-butoxycarbonyl group; $R^3$-$R^{34}$ each independently denote a hydrogen atom, substituted or unsubstituted monovalent hydrocarbon group, organooxy group, or halogen atom; and m and n each denote an integer no smaller than 1 such that m+n≦10.

3. The compound as defined in claim 2, wherein $R^3$-$R^{34}$ each independently denote a hydrogen atom, substituted or unsubstituted monovalent hydrocarbon group, or halogen atom; and m and n each denote an integer no smaller than 1 such that m+n≦5.

4. The compound as defined in claim 2, wherein the monovalent hydrocarbon group denoted by any of $R^3$-$R^{34}$ is a phenyl group, biphenyl group, or naphthyl group.

5. The compound as defined in claim 2, wherein the halogen atom is a fluorine atom.

6. A charge transport varnish which contains either the oligoaniline compound or the oxidized oligoaniline compound as defined in claim 1.

7. The charge transport varnish as defined in claim 6 which further contains an electron accepting dopant substance or a hole accepting dopant substance.

8. The charge transport varnish as defined in claim 7, wherein said charge accepting dopant substance is an arylsulfonic acid derivative represented by the formula (2).

[Chemical Formula 2]

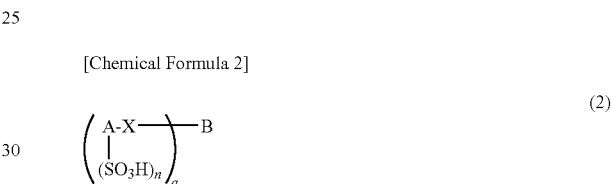

(2)

[where X denotes O, S, or NH; A denotes a naphthalene ring or anthracene ring which may have a substituent group other than X and $SO_3H$ groups as many as n; and B denotes a substituted or unsubstituted hydrocarbon group, 1,3,5-triazine group, or substituted or unsubstituted group represented by the formula (3) or (4)

[Chemical Formula 3]

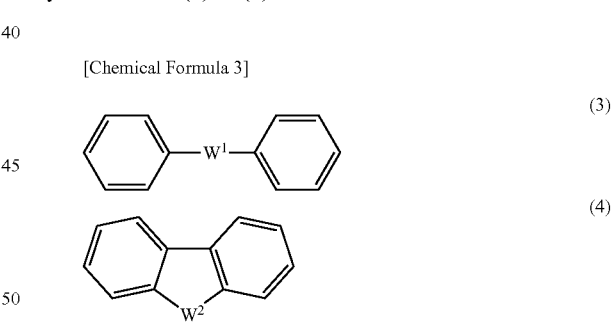

(3)

(4)

(where $W^1$ and $W^2$ each independently denote any of O, S, S(O) group, and $S(O_2)$ group, or any of substituted or unsubstituted N, Si, P, and P(O) group); n denotes the number of sulfonic acid groups connecting to A, which is an integer such that 1≦n≦4; and q denotes the number of B connecting to X, which is an integer that satisfies 1≦q).

9. The charge transport varnish as defined in claim 6, which further contains at least one species of silane compounds.

10. The charge transport varnish as defined in claim 9, which is dissolved in an organic solvent.

11. The charge transport varnish as defined in claim 10, whose organic solvent contains 0.0001 to 10 wt % of water.

12. The charge transport varnish as defined in claim 9, in which the amount of said silane compound contained therein is 1 to 50 wt % for the total amount of solids thereof.

13. The charge transport varnish as defined in claim 9, in which said silane compound is at least one species selected from dialkoxysilane compounds, trialkoxysilane compounds, tetraalkoxysilane compounds, and silicone compounds.

14. The charge transport varnish as defined in claim 13, in which said silane compound is a trialkoxysilane compound.

15. The charge transport varnish as defined in claim 14, in which said trialkoxysilane is one represented by the formula (27).

$$Y^1Si(OY^2)_3 \tag{27}$$

(where $Y^1$ denotes a halogen atom, hydrogen atom, or any of $C_{1-12}$ alkyl group, $C_{2-12}$ alkenyl group, $C_{2-12}$ alkynyl group, aryl group, or heteroaryl group which may be substituted with Z and $Y^2$ denotes a $C_{1-12}$ alkyl group, with Z denoting a halogen atom, hydrogen atom, $C_{1-12}$ haloalkyl group, $C_{1-12}$ alkyl group, hydroxyl group, mercapto group, amino group, $C_{1-12}$ haloalkoxyl group, $C_{1-12}$ alkoxyl group, $C_{2-12}$ alkenyl group, $C_{2-12}$ haloalkenyl group, $C_{2-12}$ alkynyl group, $C_{2-12}$ haloalkynyl group, $C_{1-12}$ alkylthio group, $C_{1-12}$ monoalkylamino group, $C_{1-12}$ dialkylamino group, glycidoxy group, $C_{1-12}$ alkylcarbonyl group, $C_{2-12}$ alkenylcarbonyl group, $C_{2-12}$ alkynylcarbonyl group, $C_{1-12}$ alkylcarbonyloxy group, $C_{2-12}$ alkenylcarbonyloxy group, $C_{2-12}$ alkynylcarbonyloxy group, aryl group, halogenated aryl group, heteroaryl group, or halogenated heteroaryl group).

16. The charge transport varnish as defined in claim 15, in which said Z denotes a halogen atom, hydrogen atom, $C_{1-12}$ haloalkyl group, $C_{1-12}$ alkyl group, $C_{2-12}$ alkenyl group, $C_{2-12}$ haloalkenyl group, $C_{2-12}$ alkynyl group, $C_{2-12}$ haloalkynyl group, aryl group, halogenated aryl group, heteroaryl group, or halogenated heteroaryl group.

17. The charge transport varnish as defined in claim 15, in which said $Y^1$ denotes a fluorine atom, hydrogen atom, or any of $C_{1-12}$ alkyl group, $C_{2-12}$ alkenyl group, $C_{2-12}$ alkynyl group, aryl group, and heteroaryl group which may be substituted with Z; and said Z denotes a halogen atom, hydrogen atom, $C_{1-12}$ haloalkyl group, $C_{1-12}$ alkyl group, $C_{2-12}$ alkenyl group, $C_{2-12}$ haloalkenyl group, $C_{2-12}$ alkynyl group, $C_{2-12}$ haloalkynyl group, aryl group, halogenated aryl group, heteroaryl group, or halogenated heteroaryl group.

18. The charge transport varnish as defined in claim 13, in which said silane compound is a dialkoxysilane compound.

19. The charge transport varnish as defined in claim 18, in which said dialkoxysilane compound is one represented by the formula (28)

$$Y^3Y^4Si(OY^5)_2 \tag{28}$$

(where $Y^3$ and $Y^4$ each independently denote a halogen atom or any of $C_{1-12}$ alkyl group, $C_{2-12}$ alkenyl group, $C_{2-12}$ alkynyl group, aryl group, and heteroaryl group which may be substituted with Z and $Y^5$ denotes $C_{1-12}$ alkyl group, with Z denoting a halogen atom, hydrogen atom, $C_{1-12}$ haloalkyl group, $C_{1-12}$ alkyl group, hydroxyl group, mercapto group, amino group, $C_{1-12}$ haloalkoxyl group, $C_{1-12}$ alkoxyl group, $C_{2-12}$ alkenyl group, $C_{2-12}$ haloalkenyl group, $C_{2-12}$ alkynyl group, $C_{2-12}$ haloalkynyl group, $C_{1-12}$ alkylthio group, $C_{1-12}$ monoalkylamino group, $C_{1-12}$ dialkylamino group, glycidoxy group, $C_{1-12}$ alkylcarbonyl group, $C_{2-12}$ alkenylcarbonyl group, $C_{2-12}$ alkynylcarbonyl group, $C_{1-12}$ alkylcarbonyloxy group, $C_{2-12}$ alkenylcarbonyloxy group, $C_{2-12}$ alkynylcarbonyloxy group, aryl group, halogenated aryl group, heteroaryl group, or halogenated heteroaryl group).

20. The charge transport varnish as defined in claim 19, in which said Z denotes a halogen atom, hydrogen atom, $C_{1-12}$ haloalkyl group, $C_{1-12}$ alkyl group, $C_{2-12}$ alkenyl group, $C_{2-12}$ haloalkenyl group, $C_{2-12}$ alkynyl group, $C_{2-12}$ haloalkynyl group, aryl group, halogenated aryl group, heteroaryl group, or halogenated heteroaryl group.

21. The charge transport varnish as defined in claim 19, in which said $Y^3$ and $Y^4$ each independently denote a fluorine atom, hydrogen atom, or any of $C_{1-12}$ alkyl group, $C_{2-12}$ alkenyl group, $C_{2-12}$ alkynyl group, aryl group, and heteroaryl group which may be substituted with Z which denotes a halogen atom, hydrogen atom, $C_{1-12}$ haloalkyl group, $C_{1-12}$ alkyl group, $C_{2-12}$ alkenyl group, $C_{2-12}$ haloalkenyl group, $C_{2-12}$ alkynyl group, $C_{2-12}$ haloalkynyl group, aryl group, halogenated aryl group, heteroaryl group, or halogenated heteroaryl group.

22. The charge transport varnish as defined in claim 13, in which said silane compound is a tetraalkoxysilane compound.

23. The charge transport varnish as defined in claim 22, in which said tetraalkoxysilane compound is one represented by the formula (29)

$$Si(OY^6)_4 \tag{29}$$

(where $Y^6$ denotes a $C_{1-12}$ alkyl group).

24. The charge transport varnish as defined in claim 23, in which said $Y^6$ denotes a methyl group, ethyl group, or propyl group.

25. The charge transport varnish as defined in claim 9, in which said silane compound is a combination of at least two species selected from dialkoxysilane compounds, trialkoxysilane compounds, tetraalkoxysilane compounds, and silicone compounds.

26. The charge transport varnish as defined in claim 9, in which said silane compound is a combination of at least two species selected from trialkoxysilane compounds, tetraalkoxysilane compounds, and dialkoxysilane compounds.

27. The charge transport varnish as defined in claim 9, in which said silane compound is a combination of at least two species selected from trialkoxysilane compounds.

28. The charge transport varnish as defined in claim 9, in which said silane compound is a combination of at least two species selected from tetraalkoxysilane compounds.

29. The charge transport varnish as defined in claim 9, in which said silane compound is a combination of at least two species selected from dialkoxysilane compounds.

30. The charge transport varnish as defined in claim 9, in which said silane compound is a combination of one or more species selected from trialkoxysilane compounds and one or more species selected from tetraalkoxysilane compounds.

31. The charge transport varnish as defined in claim 9, in which said silane compound is a combination of one or more species selected from trialkoxysilane compounds and one or more species selected from dialkoxysilane compounds.

32. The charge transport varnish as defined in claim 9, in which said silane compound is a combination of one or more species selected from trialkoxysilane compounds and one or more species selected from silicone compounds.

33. The charge transport varnish as defined in claim 9, in which said silane compound is a combination of one or more species selected from tetraalkoxysilane compounds and one or more species selected from dialkoxysilane compounds.

34. The charge transport varnish as defined in claim 9, in which said silane compound is a combination of one or more species selected from tetraalkoxysilane compounds and one or more species selected from silicone compounds.

35. The charge transport varnish as defined in claim 9, in which said silane compound is a combination of one or more species selected from dialkoxysilane compounds and one or more species selected from silicone compounds.

36. A charge transport thin film which is formed from the charge transport varnish as defined in claim 6.

37. A quinonediimine compound wherein the quinonediimine compound is the oxidized form of an oligoaniline compound represented by the formula (1)

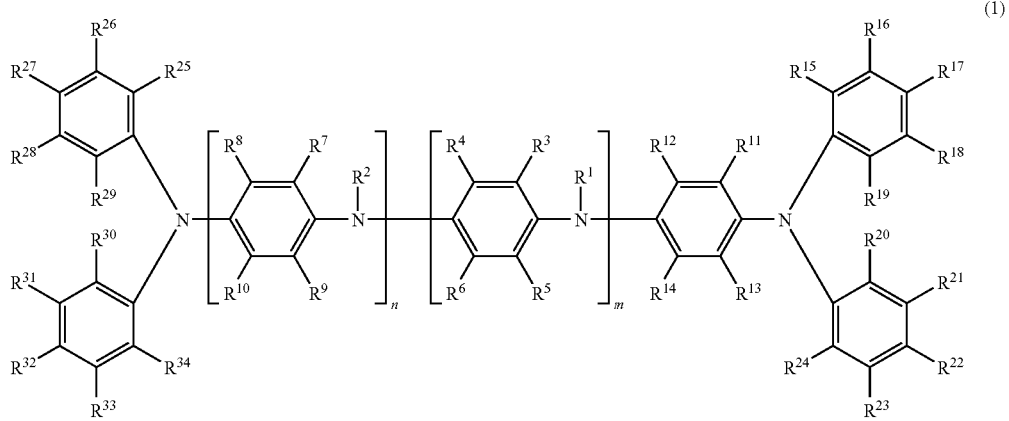

(1)

wherein $R^1$ and $R^2$ each independently denote a hydrogen atom, substituted or unsubstituted alkyl group, cycloalkyl group, bicycloalkyl group or alkenyl group, t-butoxycarbonyl group, or benzyloxycarbonyl group; $R^3$-$R^{34}$ each independently denote a hydrogen atom, hydroxyl group, silanol group, thiol group, carboxyl group, phosphoric acid group, phosphoric ester group, ester group, thioester group, amido group, nitro group, substituted or unsubstituted monovalent hydrocarbon group, organooxy group, organoamino group, organosilyl group, organothio group, acyl group, sulfonic group, or halogen atom; and m and n each denote an integer no smaller than 1 such that m+n≦20.

38. A charge transport thin film which contains the compound as defined in claim 1 or the quinonediimine compound as defined in claim 37.

39. An organic electroluminescence device having the charge transport thin film as defined in claim 38.

\* \* \* \* \*